US012776420B2

(12) United States Patent
Eltoukhy et al.

(10) Patent No.: US 12,776,420 B2
(45) **Date of Patent: *Oct. 27, 2026**

(54) DATABASE FOR THERAPEUTIC INTERVENTIONS

(71) Applicant: GUARDANT HEALTH, INC., Palo Alto, CA (US)

(72) Inventors: Helmy Eltoukhy, Atherton, CA (US); AmirAli Talasaz, Atherton, CA (US); Bahram Ghaffarzadeh Kermani, Los Altos, CA (US); Nnamdi Ihuegbu, San Francisco, CA (US)

(73) Assignee: Guardant Health, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/822,058

(22) Filed: Aug. 24, 2022

(65) Prior Publication Data

US 2024/0071628 A1 Feb. 29, 2024

Related U.S. Application Data

(63) Continuation of application No. 17/818,944, filed on Aug. 10, 2022, which is a continuation of application
(Continued)

(51) Int. Cl.
*G16H 70/20* (2018.01)
*G16B 20/20* (2019.01)
(Continued)

(52) U.S. Cl.
CPC ............. *G16H 70/20* (2018.01); *G16B 20/20* (2019.02); *G16B 30/10* (2019.02); *G16B 50/30* (2019.02); *G16H 70/60* (2018.01)

(58) Field of Classification Search
CPC ........ G16B 20/20; G16B 50/30; G16B 30/10; G16H 70/00; G16H 70/20; G16H 70/60
(Continued)

(56) References Cited

U.S. PATENT DOCUMENTS

| | | | |
|---|---|---|---|
| 5,648,245 | A | 7/1997 | Fire et al. |
| 5,952,170 | A | 9/1999 | Stroun et al. |

(Continued)

FOREIGN PATENT DOCUMENTS

| | | | |
|---|---|---|---|
| EP | 1647600 | A2 | 6/2006 |
| EP | 3371309 | A1 | 9/2018 |

(Continued)

OTHER PUBLICATIONS

Osama M. Zaytoun et al. ; When serial prostate biopsy is recommended: most cancers detected are clinically insignificant; BJU International / vol. 110, Issue 7 / p. 987-992; : Mar. 15, 2012 https://doi.org/10.1111/j.1464-410X.2012.10958.x (Year: 2012).*

(Continued)

*Primary Examiner* — Hiep V Nguyen
(74) *Attorney, Agent, or Firm* — Stephen W. Chen; Timothy Hott

(57) ABSTRACT

This disclosure provides, among other things, methods for compiling and using a database for identifying one or more therapeutic interventions for a cancer and/or the efficacy of a therapeutic intervention for subjects with a tumor genomic profile. The database may include, for each of a plurality of subjects having cancer: (i) tumor genomic testing data, including somatic alterations, collected at two or more time intervals per subject via serial biopsy of cell-free DNA, (ii) one or more therapeutic interventions administered to each of the subjects at one or more times; and (iii) efficacy of the therapeutic interventions.

20 Claims, 39 Drawing Sheets

Related U.S. Application Data

No. 17/699,968, filed on Mar. 21, 2022, which is a continuation of application No. 17/462,906, filed on Aug. 31, 2021, which is a continuation of application No. 17/000,010, filed on Aug. 21, 2020, which is a continuation of application No. 15/431,395, filed on Feb. 13, 2017, which is a continuation of application No. PCT/US2015/067717, filed on Dec. 28, 2015.

(60) Provisional application No. 62/155,763, filed on May 1, 2015, provisional application No. 62/098,426, filed on Dec. 31, 2014.

(51) Int. Cl.

| | |
|---|---|
| ***G16B 30/10*** | (2019.01) |
| ***G16B 50/30*** | (2019.01) |
| ***G16H 70/60*** | (2018.01) |

(58) Field of Classification Search

USPC ..................................................... 705/2

See application file for complete search history.

(56) References Cited

U.S. PATENT DOCUMENTS

| | | | | |
|---|---|---|---|---|
| 6,492,121 | B2 | 12/2002 | Kurane et al. | |
| 7,163,789 | B2 | 1/2007 | Chen et al. | |
| 7,824,889 | B2 | 11/2010 | Vogelstein et al. | |
| 7,915,015 | B2 | 3/2011 | Vogelstein et al. | |
| 7,937,225 | B2 | 5/2011 | Mishra et al. | |
| 8,583,380 | B2 | 11/2013 | Stephan et al. | |
| 8,603,749 | B2 | 12/2013 | Gillevet | |
| 8,685,678 | B2 | 4/2014 | Casbon et al. | |
| 9,018,365 | B2 | 4/2015 | Brenner | |
| 9,404,156 | B2 | 8/2016 | Hicks et al. | |
| 9,752,188 | B2 | 9/2017 | Schmitt et al. | |
| 9,792,403 | B2 | 10/2017 | Sun et al. | |
| 9,834,822 | B2 | 12/2017 | Talasaz | |
| D810,111 | S | 2/2018 | Garcia et al. | |
| 10,604,804 | B2 | 3/2020 | Salk et al. | |
| 11,279,767 | B2 | 3/2022 | Bourgon et al. | |
| 11,300,570 | B2 | 4/2022 | Fabrizio et al. | |
| D1,049,146 | S | 10/2024 | Shah et al. | |
| D1,050,165 | S | 11/2024 | Shah et al. | |
| 2002/0072058 | A1 | 6/2002 | Voelker et al. | |
| 2005/0122325 | A1 | 6/2005 | Twait | |
| 2006/0073506 | A1 | 4/2006 | Christians et al. | |
| 2006/0199189 | A1 | 9/2006 | Bradford | |
| 2007/0065823 | A1 | 3/2007 | Dressman et al. | |
| 2009/0105959 | A1 | 4/2009 | Braverman et al. | |
| 2009/0156906 | A1 | 6/2009 | Liebman et al. | |
| 2010/0069250 | A1 | 3/2010 | White et al. | |
| 2010/0323348 | A1 | 12/2010 | Hamady et al. | |
| 2011/0201507 | A1 | 8/2011 | Rava et al. | |
| 2012/0136583 | A1 | 5/2012 | Lazar et al. | |
| 2012/0316074 | A1 | 12/2012 | Saxonov | |
| 2013/0005585 | A1 | 1/2013 | Anderson et al. | |
| 2013/0022977 | A1 | 1/2013 | Lapidus et al. | |
| 2013/0077837 | A1 | 3/2013 | Gobinet et al. | |
| 2013/0136799 | A1* | 5/2013 | Faham ................. | C12Q 1/6886 424/577 |
| 2013/0210643 | A1 | 8/2013 | Casbon et al. | |
| 2013/0224743 | A1 | 8/2013 | Casbon et al. | |
| 2013/0237458 | A1 | 9/2013 | Casbon et al. | |
| 2013/0267424 | A1 | 10/2013 | Casbon et al. | |
| 2013/0294676 | A1 | 11/2013 | Parvin et al. | |
| 2014/0227705 | A1 | 8/2014 | Vogelstein et al. | |
| 2014/0287937 | A1* | 9/2014 | So ........................ | C12Q 1/6855 435/6.12 |
| 2016/0326597 | A1 | 11/2016 | Chan et al. | |
| 2017/0240973 | A1 | 8/2017 | Eltoukhy et al. | |
| 2017/0260590 | A1 | 9/2017 | Eltoukhy et al. | |
| 2017/0267760 | A1 | 9/2017 | Diaz et al. | |
| 2018/0251848 | A1 | 9/2018 | Diehn et al. | |
| 2018/0282417 | A1 | 10/2018 | Higgs et al. | |
| 2018/0300456 | A1 | 10/2018 | Eltoukhy et al. | |
| 2018/0305738 | A1 | 10/2018 | Kennedy et al. | |
| 2018/0363066 | A1 | 12/2018 | Chalmers et al. | |
| 2019/0025308 | A1 | 1/2019 | Cummings et al. | |
| 2019/0085403 | A1 | 3/2019 | Frampton et al. | |
| 2019/0169685 | A1 | 6/2019 | Georgiadis et al. | |
| 2020/0032323 | A1 | 1/2020 | Talasaz et al. | |
| 2020/0308656 | A1* | 10/2020 | Lewin .................. | C12Q 1/6886 |
| 2021/0040565 | A1 | 2/2021 | Eltoukhy et al. | |
| 2021/0057046 | A1* | 2/2021 | Liu ........................ | G16B 40/20 |
| 2021/0395837 | A1 | 12/2021 | Eltoukhy et al. | |
| 2024/0052419 | A1 | 2/2024 | Eltoukhy et al. | |
| 2024/0071628 | A1 | 2/2024 | Eltoukhy et al. | |
| 2024/0153593 | A1 | 5/2024 | Eltoukhy et al. | |

FOREIGN PATENT DOCUMENTS

| | | | | | |
|---|---|---|---|---|---|
| WO | 2000058516 | A2 | 10/2000 | | |
| WO | 2012014877 | A1 | 2/2012 | | |
| WO | 2012024543 | A1 | 2/2012 | | |
| WO | 2012028746 | A1 | 3/2012 | | |
| WO | 2012112804 | A1 | 8/2012 | | |
| WO | 2013019075 | A2 | 2/2013 | | |
| WO | 2013142389 | A1 | 9/2013 | | |
| WO | 2013190441 | A2 | 12/2013 | | |
| WO | 2014039556 | A1 | 3/2014 | | |
| WO | 2014043763 | A1 | 3/2014 | | |
| WO | 2014055635 | A1 | 4/2014 | | |
| WO | 2014149134 | A2 | 9/2014 | | |
| WO | WO-2014151117 | A1 * | 9/2014 | ............. | G16B 30/10 |
| WO | 2014165549 | A1 | 10/2014 | | |
| WO | 2014191938 | A1 | 12/2014 | | |
| WO | WO-2015069827 | A2 * | 5/2015 | ............. | G06F 18/24 |
| WO | 2015100427 | A1 | 7/2015 | | |
| WO | 2016100638 | A1 | 6/2016 | | |
| WO | 2016081947 | A3 | 7/2016 | | |
| WO | WO-2018213498 | A1 * | 11/2018 | ............. | G16B 20/20 |
| WO | 2019211418 | A1 | 11/2019 | | |

OTHER PUBLICATIONS

Farhana Haseen; A randomised controlled trial to evaluate the efficacy of a 6 month dietary and physical activity intervention for prostate cancer patients receiving androgen deprivation therapy; Trials 2010, 11:86 http://www.trialsjournal.com/content/11/1/86 (Year: 2010).*

Alkan, et al. Personalized copy No. and segmental duplication maps using next-generation sequencing. Nat Genet. Oct. 2009;41(10):1061-7. doi: 10.1038/ng.437. Epub Aug. 30, 2009.

Atanur, et al. The genome sequence of the spontaneously hypertensive rat: Analysis and functional significance. Genome Res. Jun. 2010;20(6):791-803. doi: 10.1101/gr.103499.109. Epub Apr. 29, 2010.

Bailey, et al. Implementation of Biomarker-Driven Cancer Therapy: Existing Tools and Remaining Gaps. Discov Med. Feb. 2014; 17(92): 101-114.

Bonaldo, et al. Normalization and subtraction: two approaches to facilitate gene discovery. Genome Res. Sep. 1996;6(9):791-806.

Bozic, et al. Evolutionary dynamics of cancer in response to targeted combination therapy. Elife. Jun. 25, 2013;2:e00747. doi: 10.7554/elife.00747.

Canadian Office Action for Application No. 2972433, dated Jan. 6, 2022.

Carr, et al. Inferring relative proportions of DNA variants from sequencing electropherograms. Bioinformatics. Dec. 15, 2009;25(24):3244-50. doi: 10.1093/bioinformatics/btp583. Epub Oct. 9, 2009.

Castle, et al. DNA copy number, including telomeres and mitochondria, assayed using next-generation sequencing. BMC Genomics. Apr. 16, 2010;11:244. doi: 10.1186/1471-2164-11-244.

Chalmers, Z.R. et al. "Analysis of 100,000 human cancer genomes reveals the landscape of tumor mutational burden" Genome Med (2017) 9:34.

(56) References Cited

OTHER PUBLICATIONS

Champiat, S. et al. "Exomics and Immunogenics: Bridging mutational load and immune checkpoints efficacy" OncoImmunology (2014) 3:327817 (6 pages).
Chang, et al. Detection of allelic imbalance in ascitic supernatant by digital single nucleotide polymorphism analysis. Clin Cancer Res. Aug. 2002;8(8):2580-5.
Costello, et al. Discovery and characterization of artifactual mutations in deep coverage targeted capture sequencing data due to oxidative DNA damage during sample preparation. Nucleic Acids Res. Apr. 1, 2013;41(6):e67. doi: 10.1093/nar/gks1443. Epub Jan. 8, 2013.
Daines, et al. High-throughput multiplex sequencing to discover copy number variants in *Drosophila*. Genetics. Aug. 2009;182(4):935-41. doi: 10.1534/genetics.109.103218. Epub Jun. 15, 2009.
Dillon et al. "DNA Instability at Chromosomal Fragile Sites in Cancer" Cure Genomics (Aug. 2010) 11(5):326-337.
Ding, L. et al. "Clonal evolution in relapsed acute myeloid leukemia revealed by whole-genome sequencing" Nature (2012) 481(7382):506-510.
Extended European search report and opinion dated Oct. 19, 2018 for EP Application No. 15876120.5.
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Fan, et al. Non-invasive prenatal measurement of the fetal genome. Nature. Jul. 19, 2012;487(7407):320-4. doi: 10.1038/nature 11251.
Final Office Action for U.S. Appl. No. 15/431,395, dated Jul. 23, 2020.
Final Office Action for U.S. Appl. No. 15/431,395, dated oct. 12, 2021.
Final Office Action in U.S. Appl. No. 17/462,906 dated Jun. 3, 2022.
Forshew, T. et al. "Noninvasive Identification and Monitoring of Cancer Mutations by Targeted Deep Sequencing of Plasma DNA" Sci Transl Med (2012) 4(136) ra68.
Gerlinger, M. et al. "Intratumor heterogeneity and Branched Evolution Revealed by Multiregion Sequencing" New England J Medicine (2012) 366(10):883-892.
Grant, et al. SNP genotyping on a genome-wide amplified DOP-PCR template. Nucleic Acids Res. Nov. 15, 2002;30(22):e25.
*Guardant Health Inc*. vs. *Foundation Medicine GmbH* Docket No. 7 O 1084/21 regarding EP3240911B1, Statement of Defense dated Nov. 8, 2021.
Gundry, et al. "Direct mutation analysis by high-throughput sequencing: from gremlin to low-abundant, somatic variants" Mutat Res Jan. 3, 2012; 729(1-2): 1-15. doi: 10.1016/mrfmmm.2011.10.001. Pub Oct. 12, 2011.
Gundry, et al. Direct, genome-wide assessment of DNA mutations in single cells. Nucleic Acids Res. Mar. 2012;40(5):2032-40. doi: 10.1093/nar/gkr949. Epub Nov. 15, 2011.
Hamady, et al. Error-correcting barcoded primers for pyrosequencing hundreds of samples in multiplex. Nat Methods. Mar. 2008;5(3):235-7. doi: 10.1038/nmeth. 1184. Epub Feb. 10, 2008.
Hellmann, M.D. et al. "Genomic Features of Response to Combination Immunotherapy in Patients with Advanced Non-Small-Cell Lung Cancer" Cancer Cell (2018) 33:843-852.
Hensel, et al. Simultaneous identification of bacterial virulence genes by negative selection. Science. Jul. 21, 1995;269(5222):400-3.
Hiatt, et al. Single molecule molecular inversion probes for targeted, high-accuracy detection of low-frequency variation. Genome Res. May 2013;23(5):843-54. doi: 10.1101/gr.147686.112. Epub Feb. 4, 2013.
International search report and written opinion dated Apr. 11, 2016 for PCT/US2015/067717.
International search report and written opinion dated May 7, 2012 for PCT/IB2011/003160.
IPR2019-00652, Final Written Decision of U.S. Pat. No. 9,834,822, dated Aug. 18, 2020.
Japanese Office Action for Application No. 2020-073957, dated Dec. 14, 2021.
Lizardi, et al. Mutation detection and single-molecule counting using isothermal rolling-circle amplification. Nat Genet. Jul. 1998;19(3):225-32.
Makrigiorgos, et al., A PCR-Based amplification method retaining quantative difference between two complex genomes. Nature Biotech, vol. 20, No. 9, pp. 936-939 (Sep. 2002).
Mattos-Arruda, L. et al. "Circulating Tumour Cells and Cell-Free DNA as Tools for Managing Breast Cancer" Nat Rev Clin Oncol (2013) 10:377-389.
Mcgranahan, N. et al. "Clonal neoantigens elicit T cell immunoreactivity and sensitivity to immune checkpoint plockade" Science (2016) 351(6280):1463-1469.
Medvedev, et al. Detecting copy number variation with mated short reads. Genome Res. Nov. 2010;20(11):1613-22. doi: 10.1101/gr. 106344.110. Epub Aug. 30, 2010.
Mei, et al. Identification of recurrent regions of Copy-Number Variants across multiple individuals. BMC Bioinformatics. Mar. 22, 2010;11:147. doi: 10.1186/1471-2105-11-147.
Notice of allowance dated Mar. 21, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Oct. 3, 2013 for U.S. Appl. No. 12/969,581.
Office Action for U.S. Appl. No. 15/431,395, dated Feb. 24, 2020.
Office Action for U.S. Appl. No. 15/431,395, dated Jun. 17, 2021.
Office Action for U.S. Appl. No. 17/462,906 dated Feb. 18, 2022.
Office Action for U.S. Appl. No. 17/699,968 dated May 5, 2022.
Ogino, et al. Quantification of PCR bias caused by a single nucleotide polymorphism in SMN gene dosage analysis. J Mol Diagn. Nov. 2002;4(4):185-90.
Park, et al. Discovery of common Asian copy number variants using integrated high-resolution array CGH and massively parallel DNA sequencing. Nat Genet. May 2010;42(5):400-5. doi: 10.1038/ng. 555. Epub Apr. 4, 2010.
Pleasance, et al. A small-cell lung cancer genome with complex signatures of tobacco exposure. Nature. Jan. 14, 2010;463(7278):184-90. doi: 10.1038/nature08629. Epub Dec. 16, 2009.
Rizvi, H. et al. "Molecular Determinants of Response to Anti-Programmed Cell Death (PD)-1 and Anti-Programmed Death-Ligand 1 (PD-L1) Blockade in Patients With Non-Small-Cell Lung Cancer Profiled With Targeted Next-Generation Sequencing" J. Clin Oncology (2018) 36(7):633-641 and Appendix.
Rizvi, N.A. et al. "Mutational landscape determines sensitivity to PD-1 blockade in non-small cell lung cancer" Science (2015) 348:124-128.
Rosenberg, J.E. et al. "Atezolizumab in patients with locally advanced and metastatic urothelial carcinoma who have progressed following treatment with platinum-based chemotherapy: a single-arm, multicentre, phase 2 trial" Lancet (2016) 387(10031):1909-1920.
Schmitt, et al. Detection of ultra-rare mutations by next-generation sequencing. Proc Natl Acad Sci U S A. Sep. 4, 2012;109(36):14508-13. doi: 10.1073/pnas.1208715109. Epub Aug. 1, 2012.
Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.
Snyder, A. et al. "Genetic Basis for Clinical Response to CTLA-4 Blockade in Melanoma" NEJM (2014) 371 (23):2189-2199.
Stephens, K.E. et al. "Epigenetic Regulation and Measurement of Epigenetic Changes" Biol Res Nurs (2013) 15(4):373-381.
Tan, et al. Genome-wide comparison of DNA hydroxymethylation in mouse embryonic stem cells and neural progenitor cells by a new comparative hMeDIP-seq method. Nucleic Acids Res. Apr. 2013;41(7):e84. doi: 10.1093/nar/gkt091. Epub Feb. 13, 2013.
Taudien, et al. Haplotyping and copy number estimation of the highly polymorphic human beta-defensin locus on 8p23 by 454 amplicon sequencing. BMC Genomics. Apr. 19, 2010;11:252. doi: 10.1186/1471-2164-11-252.

(56) References Cited

OTHER PUBLICATIONS

The Cancer Genome Atlas Research Network, et al. "The Cancer Genome Atlas Pan-Cancer analysis project" Nature Genetics (2013) 45(10):1113-1120.
Tomaz, et al. Differential methylation as a cause of allele dropout at the imprinted GNAS locus. Genet Test Mol Biomarkers. Aug. 2010;14(4):455-60. doi: 10.1089/gtmb.2010.0029.
U.S. Appl. No. 61/384,001, filed Sep. 17, 2010.
U.S. Appl. No. 61/432,119, filed Jan. 12, 2011.
Walker, et al. Isothermal in vitro amplification of DNA by a restriction enzyme/DNA polymerase system. Proc Natl Acad Sci U S A. Jan. 1, 1992;89(1):392-6.
Walsh, et al. Detection of inherited mutations for breast and ovarian cancer using genomic capture and massively parallel sequencing. Proc Natl Acad Sci U S A. Jul. 13, 2010;107(28):12629-33. doi: 10.1073/pnas.1007983107. Epub Jun. 28, 2010.
Watson, S. et al. "Researchers explore blood test to detect early breast cancer" Harvard Women's Health Watch (2013) at https://www.health.harvard.edu/blog/researchers-explore-blood-test-to-detect-early-breast-cancer-201210035359 5/10 medicine.
Weber, et al. A real-time polymerase chain reaction assay for quantification of allele ratios and correction of amplification bias. Anal Biochem. Sep. 15, 2003;320(2):252-8.
Wojdacs, et al. Primer design versus PCR bias in methylation independent PCR amplifications. Epigenetics. May 16, 2009;4(4):231-4. Epub May 14, 2009.
Wood, et al. Using next-generation sequencing for high resolution multiplex analysis of copy No. variation from nanogram quantities of DNA from formalin-fixed paraffin-embedded specimens. Nucleic Acids Res. Aug. 2010;38(14):e151. doi: 10.1093/nar/gkq510. Epub Jun. 4, 2010.
Yandell, et al. A probabilistic disease-gene finder for personal genomes. Genome Res. Sep. 2011;21(9):1529-42. doi: 10.1101/gr.123158.111. Epub Jun. 23, 2011.
Yoon, et al. Sensitive and accurate detection of copy number variants using read depth of coverage. Genome Res. Sep. 2009;19(9):1586-92. doi: 10.1101/gr.092981.109. Epub Aug. 5, 2009.
Zhang, et al. The impact of next-generation sequencing on genomics. J Genet Genomics. Mar. 20, 2011;38(3):95-109. doi: 10.1016/j.jgg.2011.02.003. Epub Mar. 15, 2011.
Zhang, F. et al. "Breast cancer subtyping from plasma proteins" BMC Medical Genomics (2013) 6(Suppl 1):56.
Zmetakova, I. et al. "Evaluation of protein expression and DNA methylation profiles detected by pyrosequencing in invasive breast cancer" Neoplasma (2013) 60(6):635-646.
Final Office Action in U.S. Appl. No. 15/431,395, dated Apr. 28, 2023.
Chan, K.C.A. et al. "Noninvasive detection of cancer-associated genome-wide hypomethylation and copy number aberrations by plasma DNA bisulfite sequencing" PNAS (2013) 110(47):18761-18768.
European Office Action for EP Application No. 22176398.0, dated Aug. 30, 2023.
Non-final Office Action for U.S. Appl. No. 17/462,906, dated Aug. 16, 2023.
Non-Final Office Action for U.S. Appl. No. 17/699,968 dated Sep. 8, 2023.
Dingli, D. et al. "(A)Symmetric Stem Cell Replication and Cancer" PLoS Comp Biology (2007) 3(3):e53 482-487.
Ekundayo, B. et al. "Origins of DNA replication" PLoS Genetics (2019) 15(9):e108320, 1-20.
Office Action for U.S. Appl. No. 17/818,944 dated Dec. 7, 2023.
Pinkel, et al. High resolution analysis of DNA copy number variation using comparative genomic hybridization to microarrays. Nat Genet. Oct. 1998;20(2):207-11.
"Guardant Complete", posted date unavailable [online], [retrieved May 28, 2024]. Retrieved from internet, https://www.guardantcomplete.com/why-guardant/product-portfolio-testing-evidence (Year: 2024).
Dileep, V. et al. "Single-cell replication profiling to measure stochastic variation in mammalian replication timing" Nature Com (2018) 9:427.
Final Office Action for U.S. Appl. No. 17/462,906, dated Mar. 13, 2024.
Final Office Action for U.S. Appl. No. 17/818,944 dated Sep. 25, 2024.
Liu, B. et al. "Computational methods for detecting copy number variations in cancer genome using next generation sequencing: principles and challenges" Oncotarget (2013) 4(11):1868-1881.
Luo, H. et al. "Genome-wide estimation of firing efficiencies of origins of DNA replication from time-course copy number variation data" BMC Bioinformatics (2010) 11:247 (15 pages).
Office Action for U.S. Appl. No. 15/431,395 mailed Jul. 19, 2024.
Australian Initial Office Action for Australian Patent Application No. 2023206196 dated Jun. 23, 2025.
Brocks, D. et al. "Intratumor DNA methylation heterogeneity reflects clonal evolution in aggressive prostate cancer" Cell Rep. Aug. 7, 2014;8(3):798-806.doi: 10.1016/j.celrep.2014.06.053. Epub Jul. 24, 2014.
European Search Report for European Patent Application No. 25155747.6 dated Jun. 17, 2025.
Final Office Action for U.S. Appl. No. 17/699,968, dated Dec. 7, 2022.
Final Office Action for U.S. Appl. No. 15/431,395, dated Apr. 18, 2025.
Final Office Action for U.S. Appl. No. 17/462,906, dated Oct. 22, 2025.
Final Office Action for U.S. Appl. No. 17/699,968, dated Oct. 22, 2025.
Final Office Action for U.S. Appl. No. 17/818,944 dated Oct. 1, 2025.
Hoey, T. "Drug Resistance, Epigenetics, and Tumor Cell Heterogeneity" Sci Translational Med (2010) 2(28).
Kivioja, T., et al. Counting absolute numbers of molecules using unique molecular identifiers. Nat Methods. Nov. 20, 2011;9(1):72-4. doi: 10.1038/nmeth.1778.
Kivioja, T., et al. Counting absolute numbers of molecules using unique molecular identifiers. Nat Methods. Nov. 20, 2011;9(1):72-4. doi: 10.1038/nmeth.1778. Supplementary Material.
Non-final Office Action for U.S. Appl. No. 17/818,944, mailed Apr. 10, 2025.
Office Action for U.S. Appl. No. c17/699,968, dated May 12, 2025.
Pan, H. et al. "Epigenomic evolution in diffuse large B-cell lymphomas" Blood (2013) 122(21):634.
Sharma, S.V. et al. "A chromatin-mediated reversible drug-tolerant state in cancer cell subpopulations" Cell (2010) 141(1):69-80.
Stefansson, O.A. et al. "Epigenetic Modifications in Breast Cancer and Their Role in Personalized Medicine" Am J Pathology (2013) 183(4):1052-1063.
Chan, K.C.A. et al. "Cancer Genome Scanning in Plasma: Detection of Tumor-Associated Copy Number Aberrations, Single-Nucleotide Variants, and Tumoral Heterogeneity by Massively Parallel Sequencing" Clin Chem (2013) 59(1):211-224.
Dawson, S-J. et al. "Analysis of Circulating Tumor DNA to Monitor Metastatic Breast Cancer" New Engl. J. Med. (2013) 368:1199-1209.
Janku, "Tumor heterogeneity in the clinic: is it a real problem?" Ther Adv Med Oncol (2014) vol. 6(2)43-51.
Misale, "Emergence of KRAS mutations and acquired resistance to anti-EGFR therapy in colorectal cancer" Nature (2012) 486(7404):532-6.
Murtaza, M. et al. "Non-invasive analysis of acquired resistance to cancer therapy by sequencing of plasma DNA" Nature (May 2013) 497(7447):108-112.
Notice of Opposition for European Patent Application 22176398.0 dated Nov. 17, 2025.
Office action for U.S. Appl. No. 15/431,395 dated Jan. 28, 2026.
Final Office Action for U.S. Appl. No. 17/000,010, dated Feb. 5, 2026.

* cited by examiner

Complete Exon Sequencing

| Point Mutations (SNVs) (70 Genes) | | | | | | Amplifications (CNVs) (16 Genes) | | Fusions (6 Genes) | Indels (3 Genes) |
|---|---|---|---|---|---|---|---|---|---|
| *AKT1* | *ALK* | *APC* | *AR* | *ARAF* | *ARID1A* | *AR* | *BRAF* | *ALK* | *EGFR** |
| *ATM* | *BRAF* | *BRCA1* | *BRCA2* | *CCND1* | *CCND2* | *CCNE1* | *CDK4* | *FGFR2* | *ERBB2** |
| *CCNE1* | *CDH1* | *CDK4* | *CDK6* | *CDKN2A* | *CDKN2B* | *CDK6* | *EGFR* | *FGFR3* | *MET*** |
| *CTNNB1* | *EGFR* | *ERBB2* | *ESR1* | *EZH2* | *FBXW7* | *ERBB2* | *FGFR1* | *NTRK1* | |
| *FGFR1* | *FGFR2* | *FGFR3* | *GATA3* | *GNA11* | *GNAQ* | *FGFR2* | *KIT* | *RET* | |
| *GNAS* | *HNF1A* | *HRAS* | *IDH1* | *IDH2* | *JAK2* | *KRAS* | *MET* | *ROS1* | |
| *JAK3* | *KIT* | *KRAS* | *MAP2K1* | *MAP2K2* | *MET* | *MYC* | *PDGFRA* | | |
| *MLH1* | *MPL* | *MYC* | *NF1* | *NFE2L2* | *NOTCH1* | *PIK3CA* | *RAF1* | | |
| *NPM1* | *NRAS* | *NTRK1* | *PDGFRA* | *PIK3CA* | *PTEN* | | | | |
| *PTPN11* | *RAF1* | *RB1* | *RET* | *RHEB* | *RHOA* | | | | |
| *RIT1* | *ROS1* | *SMAD4* | *SMO* | *SRC* | *STK11* | | | | * exons 19 & 20 |
| *TERT* | *TP53* | *TSC1* | *VHL* | | | | | | * exons 19 & 20 |
| | | | | | | | | | **exon 14 skipping |

*FIG. 8*

I. <u>Genetic Information</u>

A. Collecting Sources of Genetic Material and Sequencing the Materials (11)

B. Processing Genetic Information (12)

1. Genetic Variants a) Sequence Variants b) Copy Number Variants

2. Frequency of Genetic Variants in Sample Containing Genetic Material

C. Separating information from noise (13)

II. <u>Diagnosis of Cancer</u>

A. Based on Frequency of Sequence Variants or Level of CNV (14)

B. Confidence of Detecting Genetic Variants in the Noise Range (15)

III. <u>Increase Confidence of Diagnosis</u>

A. Using a plurality of measurements to increase confidence of Diagnosis (16)

B. Using measurements at a plurality of time points to determine whether cancer is advancing, in remission or stabilized (17)

IV. <u>Generate Report/Diagnosis</u>

A. Generating genetic graph for a plurality of measurements showing mutation trend (18)

B. Generating report showing treatment results and options (19)

*FIG. 9B*

For all non-CNV (copy number variation) reported mutant allele frequencies
Transform the absolute value into a relative metric/scale that is more enable to be plotted (e.g. Multiply mutant allele frequency by 100 and take log of that value)
Compute scaling factor using maximum observed value
Using earliest test dataset
For each non-CNV alteration
Multiply the scaling factor by transformed value for each gene and use as a quantity indicator for plotting that variant
Assign a color/unique visual indicator for each alteration
For dataset for subsequent test dates
If unchanged composition of test results, continue prior panel date visual in new panel
If alterations remain the same, but quantities have changed
Recompute the quantity indicator for plotting that variant and re-plot all updated values in existing panel(s) and new panel for the latest test date.
If new alterations addition
Add the alterations to the top of all existing alterations
Compute transform values
Recompute scaling factor
Re-draw the response map, re-plotting alterations in the prior test date that are still detected in current test date as well as newly emerging alterations
If prior existing alteration is not among the set of detected alterations
Use a height of zero and plot the quantity of the alteration for all subsequent test dates
Generate Summary of Alterations and Treatment Options
Group Alterations based on max mutant allele frequencies

*FIG. 10C*

Doe, Johnxxxxxxxxxxxxxxxxxxxxxxxx (A000001)
DOB: XX/XX/XXXX | Test Number 3 | Status: CORRECTED Biopsy-Free Tumor Sequencing The chart above annotates the percentage or allele frequency of altered circulating cell-free DNA (% cfDNA) detected in this patient. The detected genomic alterations are listed in descending order by % cfDNA by gene.

The "Approved in Indication" and "Approved in Other Indication" columns describe drugs associated with specific genomic alterations. It is based on publicly available information as described in the Appendix of this Report.

Definitions

Copy Number: Amplification was detected for this gene in the patient's circulating cell-free DNA. The test only detects amplification in certain genes asterisked in Table 3. This test does not examine other copy number alterations in other genes.

Deletion (Del): The test detects short deletions in exons 19 and 20 of the *EGFR* gene. This test does not examine deletions in other genes.

Fusion: The test detects fusions of the *ALK*, *NTRK1*, *RET*, and *ROS1* genes and all their partner genes. This test does not examine fusions of other genes.

^Denotes synonymous genomic mutations that do not result in amino acid changes.

Comments

EGFR-L747L: This genomic alteration encodes a synonymous substitution that does not result in a change in the amino acid at this position. Although the protein structure is not expected to be altered, the functional consequences and exact clinical significance of this variant remain unknown. The relevance of any available therapies and clinical trials targeting this alteration is uncertain.

Electronically signed
Arthur Baca, MD PhD, [illegible] 14:53

Interpretation

Genomic alterations were detected in the circulating cell-free DNA isolated from this patient's blood specimen. These genomic alterations are cancer-associated somatic variants, some of which have been associated with either increased or reduced clinical response to specific treatments.

All genes listed in Table X were analyzed as part of the test and genomic alterations were detected only in the genes listed on the first page of this report. Genomic alterations were not detected in the other genes listed in Table X.

Amplification was detected in the circulating cell-free DNA isolated from this patient's blood specimen for the annotated gene(s). The test only detects amplification in the asterisked genes in Table X by analysis of next-generation sequencing data on circulating cell-free DNA. This test does not examine other copy number alterations in other genes. This test is not a substitute for other established tissue-based methods that detect gene amplification, for example, by immunohistochemistry (IHC) or FISH. Unlike tissue-based amplifications tests (IHC or FISH), a positive test represents the average amplification for the interrogated gene across all circulating cell-free DNA present in the patient's blood sample. For example, a positive test could represent a small population of cells with extremely high levels of the detected gene amplification. Alternatively, it could represent a large population of cells with low to medium levels of the detected gene amplification. The exact correlation between amplification obtained by the test compared to IHC or FISH, and how each test differentially guides patient management, is an area of active investigation.

*FIG. 10E*

Doe, Johnxxxxxxxxxxxxxxxxxxxxxxxxx (A000001)
DOB: XX/XX/XXXX | Test Number 3 | Status: CORRECTED Biopsy-Free Tumor Sequencing The chart above annotates the percentage or allele frequency of altered circulating cell-free DNA (% cfDNA) detected in this patient. The detected genomic alterations are listed in descending order by % cfDNA by gene.

The "Approved in Indication" and "Approved in Other Indication" columns describe drugs associated with specific genomic alterations. It is based on publicly available information as described in the Appendix of this Report.

Definitions

Copy Number: Amplification was detected for this gene in this patient's circulating cell-free DNA. The test only detects amplification in certain genes asterisked in Table 3. This test does not examine other copy number alterations in other genes.

Deletion (Del): The test detects short deletions in exons 19 and 20 of the *EGFR* gene. This test does not examine deletions in other genes.

Fusion: The test detects fusions of the *ALK*, *NTRK1*, *RET*, and *ROS1* genes and all their partner genes. This test does not examine fusions of other genes.

^Denotes synonymous genomic mutations that do not result in amino acid changes.

FIG. 10E-1

Comments

EGFR-L747L: This genomic alteration encodes a synonymous substitution that does not result in a change in the amino acid at this position. Although the protein structure is not expected to be altered, the functional consequences and exact clinical significance of this variant remain unknown. The relevance of any available therapies and clinical trials targeting this alteration is uncertain.

Electronically signed,
Arthur Baca, MD PhD, 01/27/2015 14:53

Interpretation

Genomic alterations were detected in the circulating cell-free DNA isolated from this patient's blood specimen. These genomic alterations are cancer-associated somatic variants, some of which have been associated with either increased or reduced clinical response to specific treatments.

All genes listed in Table X were analyzed as part of the test and genomic alterations were detected only in the genes listed on the first page of this report. Genomic alterations were not detected in the other genes listed in Table X.

Amplification was detected in the circulating cell-free DNA isolated from this patient's blood specimen for the annotated gene(s). The test only detects amplification in the asterisked genes in Table X by analysis of next-generation sequencing data on circulating cell-free DNA. This test does not examine other copy number alterations in other genes. This test is not a substitute for other established tissue-based methods that detect gene amplification, for example, by immunohistochemistry (IHC) or FISH. Unlike tissue-based amplification tests (IHC or FISH), a positive test represents the average amplification for the interrogated gene across all circulating cell-free DNA present in the patient's blood sample. For example, a positive test could represent a small population of cells with extremely high levels of the detected gene amplification. Alternatively, it could represent a large population of cells with low to medium levels of the detected gene amplification. The exact correlation between amplification obtained by the test compared to IHC or FISH, and how each test differentially guides patient management, is an area of active investigation.

FIG. 10E-2

Doe, Johnxxxxxxxxxxxxxxxxxxxxxx (A000001)
DOB: XX/XX/XXXX | Test Number 3 | Status: CORRECTED

Detailed Therapy Results

| Alteration | Drug | Trade Name | Target | Current Status |
|---|---|---|---|---|
| EGFR T790M amplification | Neratinib | | Egfr/Her2/ErbB4 inhibitor | Phase 2 (Non-small cell lung carcinoma (NSCLC)) Phase 3 (Breast carcinoma) |
| | CO-1686 | | Egfr T790M inhibitor | Phase 2 (Non-small cell lung carcinoma (NSCLC)) Phase 2 (Lung cancer) |
| | Panitumumab | Vectibix | Egfr inhibitory antibody | Phase 2 (Non-small cell lung carcinoma (NSCLC)) FDA Approved in other indications (Colorectal carcinoma) |
| | AZD9291 | | Egfr T790M inhibitor | Phase 3 (Non-small cell lung carcinoma (NSCLC)) Phase 3 (Lung cancer) |
| | Afatinib | Gilotrif | Irreversible pan-ErbB kinase inhibitor | FDA Approved in this indication (Non-small cell lung carcinoma (NSCLC)) FDA Approved in other indications (Lung cancer) |
| | Lapatinib | Tykerb | Egfr inhibitory antibody | Phase 2 (Non-small cell lung carcinoma (NSCLC)) FDA Approved in other indications (Breast carcinoma) |
| | Dacomitinib | | Egfr T790M inhibitor | Phase 3 (Non-small cell lung carcinoma (NSCLC)) Phase 3 (Lung cancer) |
| | Nimotuzumab | Theraloc | EGFR inhibitory antibody | Phase 2 (Non-small cell lung carcinoma (NSCLC)) Phase 3 (Gastric carcinoma, Adenocarcinoma of the nasopharynx, Glioblastoma, Head and neck squamous cell carcinoma (HNSCC), Gastroesophageal junction carcinoma, Esophageal carcinoma, Squamous cell carcinoma of the tongue) |
| | Cetuximab | Erbitux | EGFR inhibitory antibody | Phase 3 (Non-small cell lung carcinoma (NSCLC)) FDA Approved in other indications (Head and neck squamous cell carcinoma (HNSCC), Squamous cell carcinoma of the tongue, Colorectal carcinoma) |
| MET amplification | Crizotinib | Xalkori | ALK/Met kinase inhibitor | FDA Approved in this indication (Non-small cell lung carcinoma (NSCLC)) Phase 2 (Gastric carcinoma, Renal cell carcinoma) |
| | LY2801653 | | Multi-kinase inhibitor targeting Met, Ron, Axl, Flt3, and other proteins. | Phase 1 (Solid Tumor) |
| | BMS-777607 | | Met/Ron/VEGFR1,2,3/Kit/Flt3/Tie-2/TrkB/Axl small molecule kinase inhibitor. | Phase 2 (Gastric carcinoma, Prostate carcinoma, Renal cell carcinoma, Head and neck squamous cell carcinoma (HNSCC), Cutaneous squamous cell carcinoma, Esophageal carcinoma) |
| | Cabozantinib | Cometriq | Met/Ret/VEGFR1,2,3/Kit/Flt3/Tie2/TrkB/Axl small molecule kinase inhibitor | Phase 2 (Non-small cell lung carcinoma (NSCLC)) FDA Approved in other indications (Thyroid medullary carcinoma) |
| | Foretinib | | Met/VEGFR2 small molecule kinase inhibitor | Phase 2 (Non-small cell lung carcinoma (NSCLC)) Phase 2 (Gastric carcinoma, Hepatocellular carcinoma, Renal cell carcinoma, Head and neck squamous cell carcinoma) |

Continued on next page

FIG. 10F

Detailed Therapy Results

| Alteration | Drug | Trade Name | Target | Current Status |
|---|---|---|---|---|
| EGFR T790M amplification | Neratinib | | *Egfr*/Her2/ErbB4 inhibitor | Phase 2 (Non-small cell lung carcinoma (NSCLC)) Phase 3 (Breast carcinoma) |
| | CO-1686 | | *EGFR* T790M inhibitor | Phase 2 (Non-small cell lung carcinoma (NSCLC)) Phase 2 (Lung cancer) |
| | Panitumumab | Vectibix | *EGFR* inhibitory antibody | Phase 2 (Non-small cell lung carcinoma (NSCLC)) FDA approved in other indications (colorectal carcinoma) |
| | AZD9291 | | *EGFR* T790M inhibitor | Phase 3 (Non-small cell lung carcinoma (NSCLC)) Phase 3 (Lung cancer) |
| | Afatinib | Gilotrif | Irreversible pan-ErbB kinase inhibitor | FDA Approved in this indication (Non-small cell lung carcinoma (NSCLC)) FDA approved in other indications (Lung cancer) |
| | Lapatinib | Tykerb | *EGFR* inhibitory antibody | Phase 2 (Non-small cell lung carcinoma (NSCLC)) FDA approved in other indications (breast carcinoma) |
| | Dacomitinib | | *EGFR* T790M inhibitor | Phase 3 (Non-small cell lung carcinoma (NSCLC)) Phase 3 (Lung cancer) |
| | Nimotuzumab | Theraloc | *EGFR* inhibitory antibody | Phase 2 (Non-small cell lung carcinoma (NSCLC)) Phase 3 (Gastric carcinoma, Adeno carcinoma of the nasopharynx, Glioblastoma, Head and neck squamous cell carcinoma (HNSCC), Gastro esophageal junction carcinoma, Esophageal carcinoma, Squamous cell carcinoma of the tongue) |
| | Cetuximab | Erbitux | *EGFR* inhibitory antibody | Phase 3 (Non-small cell lung carcinoma (NSCLC)) FDA Approved in other indications (Head and neck squamous cell carcinoma (HNSCC), Squamous cell carcinoma of the tongue, Colorectal carcinoma |

FIG. 10F-1

| | | | | |
|---|---|---|---|---|
| MET amplification | Crizotinib | Xalkori | *ALK/Met* kinase inhibitor | FDA Approved in this indication (Non-small cell lung carcinoma (NSCLC)) Phase 2 (Gastric carcinoma, Renal cell carcinoma) |
| | LY2801653 | | Multi-kinase inhibitor targeting Met, Ros1, Axl, Flt3, and other proteins | Phase 1 (Solid Tumor) |
| | BMS-777607 | | Met/Ret/VEGFR1,2,3/Flt3/Tie-2/TrkB/Axl small molecule kinase inhibitor | Phase 2 (Gastric carcinoma, Prostate carcinoma, Renal cell carcinoma, Head and neck squamous cell carcinoma (HNSCC), Cutaneous squamous cell carcinoma, Esophageal carcinoma) |
| | Cabozantinib | Cometriq | Met/Ret/VEGFR1,2,3/Flt3/Tie-2/TrkB/Axl small molecule kinase inhibitor | Phase 2 (Non-small cell lung carcinoma (NSCLC)) FDA Approved in other indications (Thyroid medullary carcinoma) |
| | Foretinib | | Met/VEGFR2 small molecule kinase inhibitor | Phase 2 (Non-small cell lung carcinoma (NSCLC)) Phase 2 (Gastric carcinoma, Hepatocellular carcinoma, Renal cell carcinoma, Head and neck squamous cell carcinoma) |

Continued on next page

FIG. 10F-2

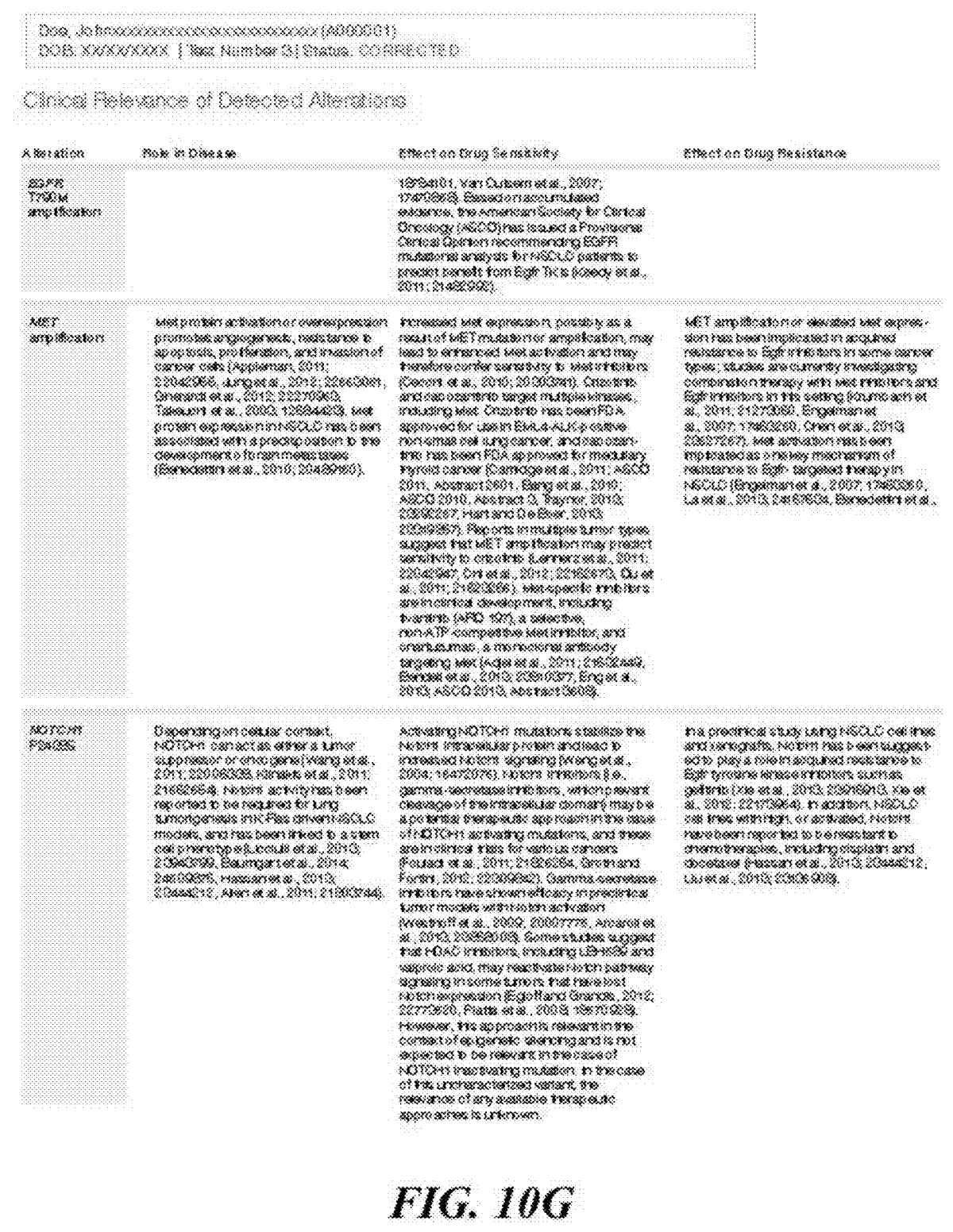

Doe, Johnxxxxxxxxxxxxxxxxxxxxxxxxx (A000001)
DOB: XX/XX/XXXX | Test Number 3 | Status: CORRECTED

Clinical Relevance of Detected Alterations

| Alteration | Role in Disease | Effect on Drug Sensitivity | Effect on Drug Resistance |
|---|---|---|---|
| EGFR T790M amplification | | 18784101, Van Cutsem et al., 2007; 17470858). Based on accumulated evidence, the American Society for Clinical Oncology (ASCO) has issued a Provisional Clinical Opinion recommending EGFR mutational analysis for NSCLC patients to predict benefit from Egfr TKIs (Keedy et al., 2011; 21482992). | |
| MET amplification | Met protein activation or overexpression promotes angiogenesis, resistance to apoptosis, proliferation, and invasion of cancer cells (Appleman, 2011; 22042966, Jung et al., 2012; 22660091, Gherardi et al., 2012; 22270953, Takeuchi et al., 2003; 12684423). Met protein expression in NSCLC has been associated with a predisposition to the development of brain metastases (Benedettini et al., 2010; 20489160). | Increased Met expression, possibly as a result of MET mutation or amplification, may lead to enhanced Met activation and may therefore confer sensitivity to Met inhibitors (Cecchi et al., 2010; 20303941). Crizotinib and cabozantinib target multiple kinases, including Met. Crizotinib has been FDA approved for use in EML4-ALK-positive non-small cell lung cancer, and cabozantinib has been FDA approved for medullary thyroid cancer (Camidge et al., 2011; ASCO 2011, Abstract 2501, Bang et al., 2010; ASCO 2010, Abstract 3, Traynor, 2013; 23352287, Hart and De Boer, 2013; 23049357). Reports in multiple tumor types suggest that MET amplification may predict sensitivity to crizotinib (Lennerz et al., 2011; 22042947, Ou et al., 2012; 22162573, Ou et al., 2011; 21623265). Met-specific inhibitors are in clinical development, including tivantinib (ARQ 197), a selective, non-ATP-competitive Met inhibitor, and onartuzumab, a monoclonal antibody targeting Met (Adjei et al., 2011; 21632449, Spigel et al., 2013; 23970977, Eng et al., 2013; ASCO 2013, Abstract 3608). | MET amplification or elevated Met expression has been implicated in acquired resistance to Egfr inhibitors in some cancer types; studies are currently investigating combination therapy with Met inhibitors and Egfr inhibitors in this setting (Krumbach et al., 2011; 21273050, Engelman et al., 2007; 17463250, Chen et al., 2013; 23527287). Met activation has been implicated as one key mechanism of resistance to Egfr-targeted therapy in NSCLC (Engelman et al., 2007; 17463250, La et al., 2013; 24167604, Benedettini et al., |
| NOTCH1 P343S | Depending on cellular context, NOTCH1 can act as either a tumor suppressor or oncogene (Wang et al., 2011; 22006338, Klinakis et al., 2011; 21562564). Notch1 activity has been reported to be required for lung tumorigenesis in K-Ras driven NSCLC models, and has been linked to a stem cell phenotype (Licciulli et al., 2013; 23943599, Baumgart et al., 2014; 24509875, Hassan et al., 2013; 23444212, Allen et al., 2011; 21880744). | Activating NOTCH1 mutations stabilize the Notch1 intracellular protein and lead to increased Notch1 signaling (Weng et al., 2004; 15472075). Notch1 inhibitors (i.e., gamma-secretase inhibitors, which prevent cleavage of the intracellular domain) may be a potential therapeutic approach in the case of NOTCH1 activating mutations, and these are in clinical trials for various cancers (Fouladi et al., 2011; 21825264, Groth and Fortini, 2012; 22309842). Gamma-secretase inhibitors have shown efficacy in preclinical tumor models with Notch activation (Weinstoff et al., 2009; 20007775, Arcaroli et al., 2013; 23858008). Some studies suggest that HDAC inhibitors, including LBH589 and valproic acid, may reactivate Notch pathway signaling in some tumors that have lost Notch expression (Egloff and Grandis, 2012; 22773820, Platta et al., 2008; 18670929). However, this approach is relevant in the context of epigenetic silencing and is not expected to be relevant in the case of NOTCH1 inactivating mutation. In the case of this uncharacterized variant, the relevance of any available therapeutic approaches is unknown. | In a preclinical study using NSCLC cell lines and xenografts, Notch1 has been suggested to play a role in acquired resistance to Egfr tyrosine kinase inhibitors such as gefitinib (Xie et al., 2013; 23916913, Xie et al., 2012; 22173964). In addition, NSCLC cell lines with high, or activated, Notch1 have been reported to be resistant to chemotherapies, including cisplatin and docetaxel (Hassan et al., 2013; 23444212, Liu et al., 2013; 23806906). |

FIG. 10G

Clinical Relevance of Detected Alterations

| Alteration | Role in Disease | Effect on Drug Sensitivity | Effect on Drug Resistance |
|---|---|---|---|
| EGFR T790M amplification | | 18784101, Van Cutsem et al., 2007; 17470858). Based on accumulated evidence, the American Society for Clinical Oncology (ASCO) has issued a Provisional Clinical Opinion recommending EGFR mutational analysis for NSCLC patients to predict benefit from Egfr TKIs (Keedy et al., 2011; 21482992). | |
| MET amplification | Met protein activation or overexpression promotes angiogenesis, resistance to apoptosis, proliferation, and invasion of cancer cells (Appleman, 2011; 22042966, Jung et al., 2012; 22553051, Gherardi et al, 2012; 22270953, Takeuchi et al., 2003 ; 12684423). Met protein expression in NSCLC has been associated with a predisposition to the development of brain metastases (Benedettini et al., 2010; 20489150). | Increased MET expression possibly as a result of MET mutation or amplification, may lead to enhanced MET activation and may therefore confer sensitivity to MET inhibitors (Cecchi et al, 2010; 20303741). Crizotinib and cabozantinib target multiple kinases, including Met. Crizotinib has been FDA approved for use in EML4-ALK positive non-small cell lung cancer, and cabozantinib has been FDA approved for medullary thyroid cancer (Camidge et al., 2011; ASCO 2011, Abstract 2501, Bang et al., 2010; ASCO 2010, Abstract 3, Traynor, 2013; 23292257, Hart and De Boer, 2013; 23319867). Reports in multiple tumor types suggest that MET amplification may predict sensitivity to crizotinib (Lennerz et al., 2011; 22042947, Chi et al., 2012; 22162573, Ou et al., 2011; 21623265). Met-specific inhibitors are in clinical development, including Tivantinib (ARQ 197), a selective non-ATP competitive MET inhibitor, and onartuzumab a monoclonal antibody targeting MET (Adjei et al., 2011; 21632449, Bendell et al., 2013; 23810377, Eng et al., 2013; ASCO 2013, Abstract 3508). | Met amplification or elevated MET expression has been implicated in acquired resistance to Egfr inhibitors in some cancer types; studies are currently investigating combination therapy with MET inhibitors and Egfr inhibitors in this setting (Krumbach et al., 2011; 21273060, Engelman et al., 2007; 17463250, Chen et al., 2013; 23527257). Met activation has been implicated as one key mechanism of resistance to Egfr-targeted therapy in NSCLC (Engelman et al., 2007; 17463250, Le et al., 2013; 24167634, Benedettini et al.) |

FIG. 10G-1

| | | | |
|---|---|---|---|
| *NOTCH1* [illegible] | Depending on cellular context, NOTCH1 can act as either a tumor suppressor or oncogene (Wang et al., 2011; 22006338, Klinakis et al., 2011; 21562564). NOTCH1 activity has been reported to be required for lung tumorigenesis in K-Ras driven NSCLC models, and has been linked to a stem cell phenotype (Licciulli et al., 2013; 23943799, Baumgart et al., 2013; 24509876, Hassan et al., 2013; 23444212, Allen et al., 2011; 21803744). | Activating NOTCH1 mutations stabilize the Notch1 intracellular protein and lead to increased Notch1 signaling (Weng et al., 2004; 15472075). Notch1 inhibitors (i.e., gamma-secretase inhibitors, which prevent cleavage of the intracellular domain) may be a potential therapeutic approach in the case of NOTCH1 activation mutations, and these are in clinical trials for various cancers (Fouladi et al., 2011; 21825264, Groth and Fortini, 2012; 22909843). Gamma-secretase inhibitors have shown efficacy in preclinical tumor models with Notch activation (Westhoff et al., 2009; 20007775, Arcaroli et al., 2013; 23658008). Some studies suggest that HDAC inhibitors, including LBH589 and valproic acid, may reactivate Notch pathway signaling in some tumors that have lost Notch expression (Egloff and Grandis, 2012; 22773520, Platta et al., 2008; 18570928). However, this approach is relevant in the context of epigenetic silencing and is not expected to be relevant in the case of NOTCH1 inactivating mutation. In the case of this uncharacterized variant, the relevance of any available therapeutic approaches is unknown. | In a preclinical study using NSCLC cell lines and xenografts, Notch1 has been suggested to play a role in acquired resistance to Egfr tyrosine kinase inhibitors such as gefitinib (Xie et al., 2013; 23916913, Xie et al., 2012; 22173954). In addition, NSCLC cell lines with high, or activated, Notch1 have been reported to be resistant to chemotherapies, including cisplatin and docetaxel (Hassan et al., 2013; 23444212). |

FIG. 10G-2

Doe, Johnxxxxxxxxxxxxxxxxxxxxxxxxxx (A000001)
DOB: XX/XX/XXXX | Test Number 3 | Status: CORRECTED Available Clinical Trials

| Alteration | Trial ID | Title | Phase | Site |
|---|---|---|---|---|
| **EGFR T790M amplification** | NCT01647711 | A Study of Intermittent, High-dose Afatinib to Determine the Maximal Tolerated Dose and Assess Activity of This Dose Against Non-small Cell Lung Cancer With T790M Mutations | Phase 1 | Aurora, CO<br>Boston, MA (2) |
| | NCT01526928 | Study to Evaluate Safety, Pharmacokinetics, and Efficacy of Rociletinib (CO-1686) in Previously Treated Mutant Epidermal Growth Factor Receptor (EGFR) in Non-Small Cell Lung Cancer (NSCLC) Patients | Phase 1/Phase 2 | Duarte, CA; Fountain Valley, CA; Los Angeles, CA (2); Orange, CA; Sacramento, CA; Santa Monica, CA; Stanford, CA; Whittier, CA (2); Aurora, CO; Washington, DC; Miami, FL; Orlando, FL; Athens, GA; Boston, MA (2); Ann Arbor, MI; Detroit, MI; Morristown, NJ; Buffalo, NY; Lake Success, NY; New York, NY; Cincinnati, OH; Columbus, PH; Tulsa, OK; Portland, OR; Philadelphia, PA, Pittsburgh, PA; Nashville, TN; Houston, TX |
| **MET amplification** | NCT01324479 | Study of INC280 in Patients With c-MET Dependent Advanced Solid Tumors | Phase 1 | Fayetteville, AR; Los Angeles, CA; Chicago, IL; Rockville, MD; Detroit, MI, Buffalo, NY; Nashville, TN, Dallas, TX; Houston, TX, Salt Lake City UT; Australia (2); Canada (2); France (3); Germany (6); Hong Kong (2); Israel (4); Italy (6); Korea (6); Netherlands (3); Norway; Singapore, Granada; Spain (6), Taiwan (2); Thailand (3) |
| | NCT01712217 | A Study of AT13387 in Patients With Non-Small Cell Lung Cancer (NSCLC) Alone and in Combination With Crizotinib | Phase 1/Phase 2 | Scottsdale, AZ; La Jolla, CA, Los Angeles, CA; San Diego, CA, Santa Monica, CA; Whittier, CA; Aurora, CO; New Haven, CT; Newark, DE; Orlando, FL; Tampa, FL; Chicago, IL (2); Ann Arbor, MI; Detroit, MI; Rochester, MN; St. Louis, MO; Omaha, NE; Lebanon, NH; Bronx, NY; New York, NY; Greensboro, NC; Winston Salem, NC; Cincinnati, OH (2); Cleveland, OH; Columbus, OH; Portland, OR; Hershey, PA, Philadelphia, PA; Memphis, TN; Nashville, TN; Dallas, TX; Fairfax, VA; Seattle, WA (2); Madison, WI; Canada (8); France (10); Korea (9); Spain (6) |

*FIG. 10H*

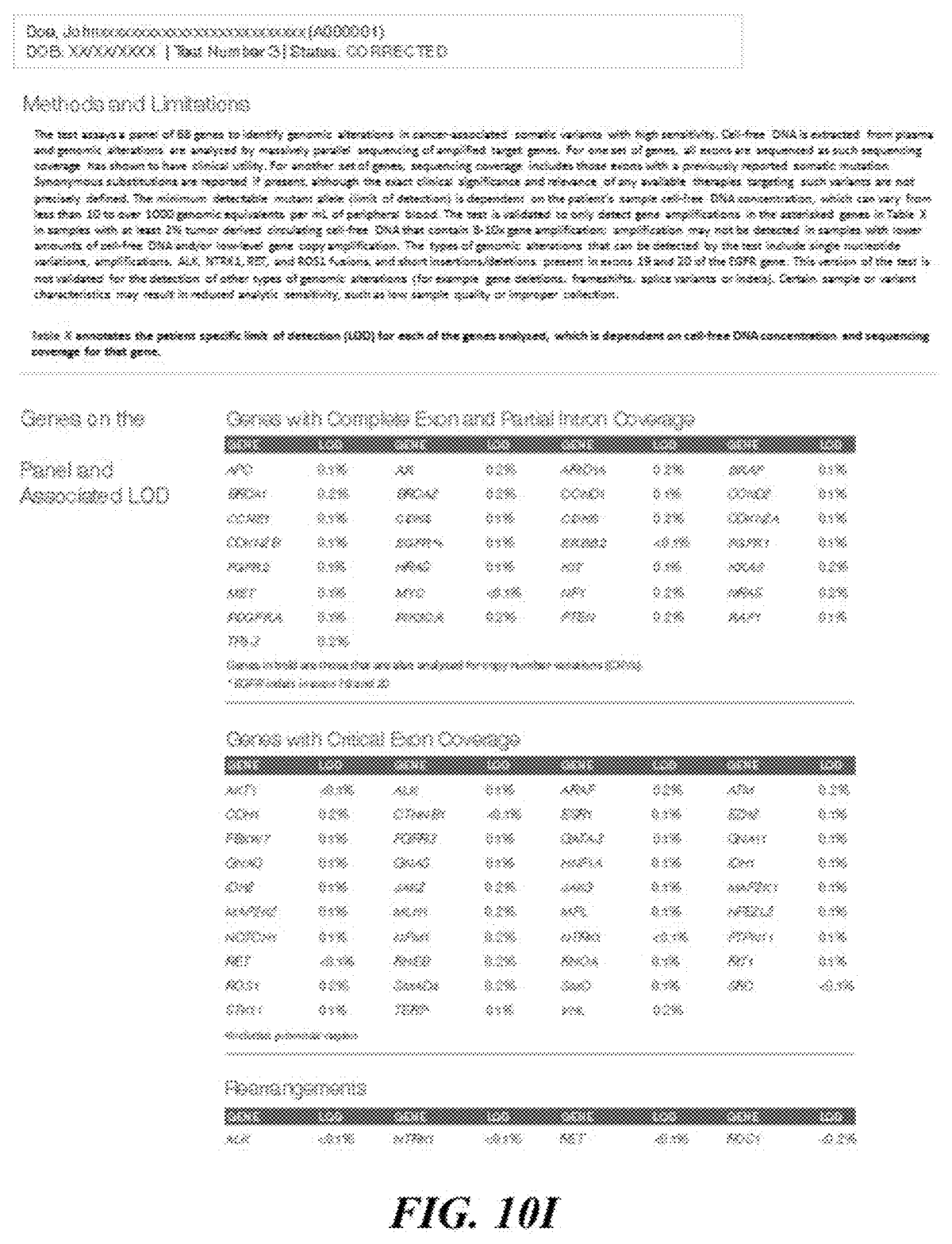

Doe, Johnxxxxxxxxxxxxxxxxxxxxxxxxx (A000001)
DOB: XX/XX/XXXX | Test Number 3 | Status: CORRECTED

Methods and Limitations

The test assays a panel of 83 genes to identify genomic alterations in cancer-associated somatic variants with high sensitivity. Cell-free DNA is extracted from plasma and genomic alterations are analyzed by massively parallel sequencing of amplified target genes. For one set of genes, all exons are sequenced as such sequencing coverage has shown to have clinical utility. For another set of genes, sequencing coverage includes those exons with a previously reported somatic mutation. Synonymous substitutions are reported if present, although the exact clinical significance and relevance of any available therapies targeting such variants are not precisely defined. The minimum detectable mutant allele (limit of detection) is dependent on the patient's sample cell-free DNA concentration, which can vary from less than 10 to over 1000 genomic equivalents per mL of peripheral blood. The test is validated to only detect gene amplifications in the asterisked genes in Table X in samples with at least 2% tumor derived circulating cell-free DNA that contain 8-10x gene amplification; amplification may not be detected in samples with lower amounts of cell-free DNA and/or low-level gene copy amplification. The types of genomic alterations that can be detected by the test include single nucleotide variations, amplifications, ALK, NTRK1, RET, and ROS1 fusions, and short insertions/deletions present in exons 19 and 20 of the EGFR gene. This version of the test is not validated for the detection of other types of genomic alterations (for example gene deletions, frameshifts, splice variants or indels). Certain sample or variant characteristics may result in reduced analytic sensitivity, such as low sample quality or improper collection.

Table X annotates the patient specific limit of detection (LOD) for each of the genes analyzed, which is dependent on cell-free DNA concentration and sequencing coverage for that gene.

Genes on the Panel and Associated LOD

Genes with Complete Exon and Partial Intron Coverage

| GENE | LOD | GENE | LOD | GENE | LOD | GENE | LOD |
|---|---|---|---|---|---|---|---|
| *APC* | 0.1% | *AR* | 0.2% | *ARID1A* | 0.2% | *BRAF* | 0.1% |
| *BRCA1* | 0.2% | *BRCA2* | 0.2% | *CCND1* | 0.1% | *CCND2* | 0.1% |
| *CCNE1* | 0.1% | *CDK4* | 0.1% | *CDK6* | 0.2% | *CDKN2A* | 0.1% |
| *CDKN2B* | 0.1% | *EGFR** | 0.1% | *ERBB2* | <0.1% | *FGFR1* | 0.1% |
| *FGFR2* | 0.1% | *HRAS* | 0.1% | *KIT* | 0.1% | *KRAS* | 0.2% |
| *MET* | 0.1% | *MYC* | <0.1% | *NF1* | 0.2% | *NRAS* | 0.2% |
| *PDGFRA* | 0.1% | *PIK3CA* | 0.2% | *PTEN* | 0.2% | *RAF1* | 0.1% |
| *TP53* | 0.2% | | | | | | |

Genes in bold are those that are also analyzed for copy number variations (CNVs).
* EGFR indels in exons 19 and 20

Genes with Critical Exon Coverage

| GENE | LOD | GENE | LOD | GENE | LOD | GENE | LOD |
|---|---|---|---|---|---|---|---|
| *AKT1* | <0.1% | *ALK* | 0.1% | *ARAF* | 0.2% | *ATM* | 0.2% |
| *CDH1* | 0.2% | *CTNNB1* | <0.1% | *ESR1* | 0.1% | *EZH2* | 0.1% |
| *FBXW7* | 0.1% | *FGFR3* | 0.1% | *GATA3* | 0.1% | *GNA11* | 0.1% |
| *GNAQ* | 0.1% | *GNAS* | 0.1% | *HNF1A* | 0.1% | *IDH1* | 0.1% |
| *IDH2* | 0.1% | *JAK2* | 0.2% | *JAK3* | 0.1% | *MAP2K1* | 0.1% |
| *MAP2K2* | 0.1% | *MLH1* | 0.2% | *MPL* | 0.1% | *NFE2L2* | 0.1% |
| *NOTCH1* | 0.1% | *NTRK1* | 0.2% | *NTRK3* | <0.1% | *PTPN11* | 0.1% |
| *RET* | <0.1% | *RHEB* | 0.2% | *RHOA* | 0.1% | *RIT1* | 0.1% |
| *ROS1* | 0.2% | *SMAD4* | 0.2% | *SMO* | 0.1% | *SRC* | <0.1% |
| *STK11* | 0.1% | *TERT* | 0.1% | *VHL* | 0.2% | | |

*Includes promoter region

Rearrangements

| GENE | LOD | GENE | LOD | GENE | LOD | GENE | LOD |
|---|---|---|---|---|---|---|---|
| *ALK* | <0.1% | *NTRK1* | <0.1% | *RET* | <0.1% | *ROS1* | <0.1% |

*FIG. 10I*

Doe, Johnxxxxxxxxxxxxxxxxxxxxxxxxxx (A000001)
DOB: XX/XX/XXXX | Test Number 3 | Status: CORRECTED

Methods and Limitations

The test assays a panel of 68 genes to identify genomic alterations in cancer-associated somatic variants with high sensitivity. Cell-free DNA is extracted from plasma and genomic alterations are analyzed by massively parallel sequencing of amplified target genes. For one set of genes, all exons are sequenced as such sequencing coverage has shown to have clinical utility. For another set of genes, sequencing coverage includes those exons with a previously reported somatic mutation. Synonymous substitutions are reported if present, although the exact clinical significance and relevance of any available therapies targeting such variants are not precisely defined. The minimum detectable mutant allele (limit of detection) is dependent on the patient's sample cell-free DNA concentration, which can vary from less than 10 to over 1000 genomic equivalents per mL of peripheral blood. The test is validated to only detect gene amplifications in the asterisked genes in Table X in samples with at least 2% tumor derived circulating cell-free DNA that contain 8-10x gene amplification; amplification may not be detected in samples with lower amounts of cell-free DNA and/or low-level gene copy amplification. The types of genomic alterations that can be detected by the test include single nucleotide variations, amplifications, ALK, NTRK1, RET, and ROS1 fusions, and short insertions/deletions present in exons 19 and 20 of the EGFR gene. This version of the test is not validated for the detection of other types of genomic alterations (for example gene deletions, frameshifts, splice variants or indels). Certain sample or variant characteristics may result in reduced analytic sensitivity, such as low sample quality or improper collection.

*FIG. 10I-1*

Table X annotates the patient specific limit of detection (LOD) for each of the genes analyzed, which is dependent on cell-free DNA concentration and sequencing coverage for that gene.

Genes with Complete Exon and Partial Intron Coverage

| GENE | LOD | GENE | LOD | GENE | LOD | GENE | LOD |
|---|---|---|---|---|---|---|---|
| APC | 0.1% | AR | 0.2% | ARID1A | 0.2% | BRAF | 0.1% |
| BRCA1 | 0.2% | BRCA2 | 0.2% | CCND1 | 0.1% | CCND2 | 0.1% |
| CCNE1 | 0.1% | CDK4 | 0.1% | CDK6 | 0.2% | CDKN2A | 0.1% |
| CDKN2B | 0.1% | EGFR*+ | 0.1% | ERBB2 | <0.1% | FGFR1 | 0.1% |
| FGFR2 | 0.1% | HRAS | 0.1% | KIT | 0.1% | KRAS | 0.2% |
| MET | 0.1% | MYC | <0.1% | NF1 | 0.2% | NRAS | 0.2% |
| PDGFRA | 0.1% | PIK3CA | 0.2% | PTEN | 0.2% | RAF1 | 0.1% |
| TP53 | 0.2% | | | | | | |

Genes in bold are those that are also analyzed for copy number variations (CNVs).
*+EGFR indels in exon 19 and 20.

Genes with Critical Exon Coverage

| GENE | LOD | GENE | LOD | GENE | LOD | GENE | LOD |
|---|---|---|---|---|---|---|---|
| AKT1 | <0.1% | ALK | 0.1% | ARAF | 0.2% | ATM | 0.2% |
| CDH1 | 0.2% | CTNNB1 | <0.1% | ESR1 | 0.1% | EZH2 | 0.1% |
| FBXW7 | 0.1% | FGFR3 | 0.1% | GATA3 | 0.1% | GNA11 | 0.1% |
| GNAQ | 0.1% | GNAS | 0.1% | HNF1A | 0.1% | IDH1 | 0.1% |
| IDH2 | 0.1% | JAK2 | 0.2% | JAK3 | 0.1% | MAP2K1 | 0.1% |
| MAP2K2 | 0.1% | MLH1 | 0.2% | MPL | 0.1% | NFE2L2 | 0.1% |
| NOTCH1 | 0.1% | NPM1 | 0.2% | NTRK1 | <0.1% | PTPN11 | 0.1% |
| RET | <0.1% | RHEB | 0.2% | RHOA | 0.1% | RIT1 | 0.1% |
| ROS1 | 0.2% | SMAD4 | 0.2% | SMO | 0.1% | SRC | <0.1% |
| STK11 | 0.1% | TERT* | 0.1% | VHL | 0.2% | | |

* Includes promoter region

Rearrangements

| GENE | LOD | GENE | LOD | GENE | LOD | GENE | LOD |
|---|---|---|---|---|---|---|---|
| ALK | <0.1% | NTRK1 | <0.1% | RET | <0.1% | ROS1 | <0.2% |

*FIG. 10I-2*

DATABASE FOR THERAPEUTIC INTERVENTIONS

CROSS-REFERENCE TO RELATED APPLICATIONS

This application is a continuation of U.S. patent application Ser. No. 17/818,944 filed Aug. 10, 2022, which is a continuation of U.S. patent application Ser. No. 17/699,968 filed Mar. 21, 2022, which is a continuation of U.S. patent application Ser. No. 17/462,906 filed Aug. 31, 2021, which is a continuation of U.S. patent application Ser. No. 17/000,010, filed Aug. 21, 2020, which is a continuation of U.S. patent application Ser. No. 15/431,395, filed Feb. 13, 2017, which is a continuation of International Patent Application No. PCT/US2015/067717, filed Dec. 28, 2015, which claims the benefit of U.S. Provisional Application No. 62/098,426, filed Dec. 31, 2014 and U.S. Provisional Application No. 62/155,763, filed on May 1, 2015, each of which is incorporated entirely herein by reference.

BACKGROUND

Health care is just now starting to effectively use information from the human genome to diagnose and treat disease. Nowhere is this more crucial than in the treatment of cancer, from which 7.6 million people in the U.S. die each year, and for which the US spends $87 billion a year on treatment. Cancer refers to any disorder of various malignant neoplasms characterized by the proliferation of anaplastic cells that tend to invade surrounding tissue and metastasize to new body sites and the pathological conditions characterized by such growths.

One of the reasons cancer is difficult to treat is that current testing methods may not help doctors match specific cancers with effective drug treatments. And it is a moving target—cancer cells are constantly changing and mutating. Cancers can accumulate genetic variants through, e.g., somatic cell mutation. Such variants include, for example, sequence variants and copy number variants. Analysis of tumors has indicated that different cells in a tumor can bear different genetic variants. Such differentiation between tumor cells has been referred to as tumor heterogeneity.

Cancers can evolve over time, becoming resistant to a therapeutic intervention. Certain variants are known to correlate with responsiveness or resistance to specific therapeutic interventions. More effective treatments for cancers exhibiting tumor heterogeneity would be beneficial. Such cancers may be treated with a second, different, therapeutic intervention to which the cancer responds.

DNA sequencing methods allow detection of genetic variants in DNA from tumor cells. Cancer tumors continually shed their unique genomic material into the bloodstream. Unfortunately, these telltale genomic "signals" are so weak that current genomic analysis technologies, including next-generation sequencing, may only detect such signals sporadically or in patients with terminally high tumor burden. The main reason for this is that such technologies are plagued by error rates and bias that can be orders of magnitude higher than what is required to reliably detect de novo genomic alterations associated with cancer.

In a parallel trend, to understand the clinical significance of a genetic test, treating professionals must have a working knowledge of basic principles of genetic inheritance and reasonable facility with the interpretation of probabilistic data. Some studies suggest that many treating professionals are not adequately prepared to interpret genetic tests for disease susceptibility. Some physicians have difficulty interpreting probabilistic data related to the clinical utility of diagnostic tests, such as the positive or negative predictive value of a laboratory test.

The error rates and bias in detecting de novo genomic alterations associated with cancer, along with inadequate explanation or the implications of the genetic tests for cancer, have lowered the quality of care for cancer patients. Professional societies, such as the College of American Pathologists (CAP) and the American College of Medical Genetics (ACMG), have published standards or guidelines for laboratories that provide genetic testing, which require that reports containing genetic information include interpretive content that is understandable by generalist physicians.

SUMMARY

In an aspect provided herein is a method comprising: (a) sequencing polynucleotides from cancer cells from a biological sample of a subject; (b) identifying and quantifying somatic mutations in the polynucleotides; (c) developing a profile of tumor heterogeneity in the subject indicating the presence and relative quantity of a plurality of the somatic mutations in the polynucleotides, wherein different relative quantities indicates tumor heterogeneity; and (d) determining a therapeutic intervention for a cancer exhibiting the tumor heterogeneity, wherein the therapeutic intervention is effective against a cancer having the profile of tumor heterogeneity determined. In some embodiments, the cancer cells are spatially distinct. In some embodiments, the therapeutic intervention is more effective against a cancer presenting with the plurality of somatic mutations than it is against a cancer presenting with any one, but not all, of the somatic mutations. In some embodiments, the method further comprises: (e) monitoring changes in tumor heterogeneity in the subject over time and determining different therapeutic interventions over time based on the changes. In some embodiments, the method further comprises: (e) displaying the therapeutic intervention. In some embodiments, the method further comprises: (e) implementing the therapeutic intervention. In some embodiments, the method further comprises: (e) generating a phylogeny of tumor evolution based on the tumor profile; wherein determining the therapeutic intervention takes into account the phylogeny.

In some embodiments, determining is performed with the aid of computer-executed algorithm. In some embodiments, sequence reads generated by sequencing are subject to noise reduction before identifying and quantifying. In some embodiments, noise reduction comprises molecular tracking of sequences generated from a single polynucleotide in the sample.

In some embodiments, determining a therapeutic intervention takes into account the relative frequencies of the tumor-related genetic alterations. In some embodiments, the therapeutic intervention comprises administering, in combination or in series, a plurality of drugs, wherein each drug is relatively more effective against a cancer presenting with a different one of somatic mutations that occur at different relative frequency. In some embodiments, a drug that is relatively more effective against a cancer presenting with a somatic mutation occurring at higher relative frequency is administered in higher amount. In some embodiments, the drugs are delivered at doses that are stratified to reflect the relative amounts of the variants in the DNA. In some embodiments, cancers presenting with at least one of the genetic variants is resistant to at least one of the drugs. In some embodiments, determining a therapeutic intervention takes into account the tissue of origin of the cancer. In some embodiments, the therapeutic intervention is determined based on a database of interventions shown to be therapeutic for cancers having tumor heterogeneity characterized by each of the somatic mutations.

In some embodiments, the polynucleotides comprise cfDNA from a blood sample. In some embodiments, the polynucleotides comprise polynucleotides from spatially distinct cancer cells. In some embodiments, the polynucleotides comprise polynucleotides from different metastatic tumor sites. In some embodiments, the polynucleotides comprise polynucleotides from a solid tumor or a diffuse tumor. In some embodiments, the polynucleotides are comprised in a blood sample or in solid tumor biopsy.

In some embodiments, identifying comprises generating a plurality of sequence reads for parent polynucleotides from the sample, and collapsing the sequence reads to generate consensus calls for bases in each parent polynucleotide. In some embodiments, quantifying comprises determining frequency at which the somatic mutations are detected in the population of polynucleotides from the biological sample. In some embodiments, the biological sample comprises biological molecules from non-disease cells. In some embodiments, the biological sample comprises biological molecules from a plurality of different tissues. In some embodiments, the biomolecules are comprised in one biological sample. In some embodiments, the biomolecules are comprised in a plurality of biological samples. In some embodiments, the plurality of biological samples are tumors from a plurality of metastases.

In some embodiments, sequencing comprises sequencing all or part of a subset of genes in the subject's genome. In some embodiments, the somatic mutations are selected from single nucleotide variations (SNVs), insertions, deletions, inversions, transversions, translocations, copy number variations (CNVs) (e.g., aneuploidy, partial aneuploidy, polyploidy), chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns and abnormal changes in nucleic acid methylation. In some embodiments, genetic loci are selected from single nucleotides, genes and chromosomes.

In some embodiments, the cancer is selected from carcinomas, sarcomas, leukemias, lymphomas, myelomas and central nervous system cancers (e.g., breast cancer, prostate cancer, colorectal cancer, brain cancer, esophageal cancer, head and neck cancer, bladder cancer, gynecological cancer, liposarcoma, and multiple myeloma). In some embodiments, cancer cells of the tumor are derived from a common parent disease cell. In some embodiments, cancer cells of the tumor are derived from different parent cancer cells of the same or different cancer type. In some embodiments, the method further comprises determining a measure of the somatic mutations to one or more control references to determine the relative quantity.

In some embodiments, the polynucleotides are sourced from both circulating cancer polynucleotides and from solid tumor biopsy. In some embodiments, profiles are separately developed for polynucleotides sourced from the circulating cancer polynucleotides and from the solid tumor biopsy.

In an aspect provided herein is a method comprising providing a therapeutic intervention for a subject having a cancer having a tumor profile from which tumor heterogeneity can be inferred, wherein the therapeutic intervention is effective against cancers with the tumor profile. In some embodiments, the tumor profile indicates relative frequency of a plurality of more somatic mutations. In some embodiments, the method further comprises monitoring changes in the relative frequencies in the subject over time and determining different therapeutic interventions over time based on the changes. In some embodiments, the therapeutic intervention is more effective against a cancer presenting with each of the somatic mutations than it is against a cancer presenting with any one, but not all, of the somatic mutations. In some embodiments, the therapeutic intervention comprises administering, in combination or in series, a plurality of drugs, wherein each drug is relatively more effective against a cancer presenting with a different one of somatic mutations that occur at different relative frequency. In some embodiments, a drug that is relatively more effective against a cancer presenting with a somatic mutation occurring at higher relative frequency is administered in higher amount. In some embodiments, the drugs are delivered at doses that are stratified to reflect the relative amounts of the variants in the DNA. In some embodiments, cancers presenting with at least one of the genetic variants is resistant to at least one of the drugs. In some embodiments, the cancer is selected from carcinomas, sarcomas, leukemias, lymphomas, myelomas and central nervous system cancers (e.g., breast cancer, prostate cancer, colorectal cancer, brain cancer, esophageal cancer, head and neck cancer, bladder cancer, gynecological cancer, liposarcoma, and multiple myeloma).

In an aspect provided herein is a method comprising administering to a subject a therapeutic intervention that is effective against a tumor exhibiting tumor heterogeneity, wherein the therapeutic intervention is based on a profile of tumor heterogeneity in the subject indicating the presence and relative quantity of a plurality of the somatic mutations in the polynucleotides, wherein different relative quantities indicates tumor heterogeneity.

In an aspect provided herein is a system comprising a computer readable medium comprising machine-executable code that, upon execution by a computer processor, implements a method comprising: (a) receiving into memory sequence reads of polynucleotides mapping to a genetic locus; (b) determining, among said sequence reads, identity of bases that are different than a base of a reference sequence at the locus of the total number of sequence reads mapping to a locus; (c) reporting the identity and relative quantity of the determined bases and their location in the genome; and (d) inferring heterogeneity of a given sample based on information in (c). In some embodiments, the method implemented further comprises receiving into memory sequence reads derived from samples at a plurality of different times and calculating a difference in relative amount and identity of a plurality of bases between the two samples.

In an aspect provided herein is a kit comprising a first pharmaceutical drug and a second pharmaceutical drug, wherein a combination of the first drug and the second drug is more therapeutically effective against a cancer presenting with a first and a second somatic mutation than it is against a cancer presenting with any one, but not all, of the somatic mutations. In some embodiments, the combination is contained in a mixture or each drug is contained in a separate container.

In an aspect provided herein is a method comprising: (a) performing biomolecular analysis of biomolecular polymers from disease cells (e.g., spatially distinct disease cells) from a subject; (b) identifying and quantifying biomolecular variants in the biomolecular macromolecules; (c) developing a profile of disease cell heterogeneity in the subject indicating the presence and relative quantity of a plurality of the variants in the biomolecular macromolecules, wherein different relative quantities indicates disease cell heterogeneity; and (d) determining a therapeutic intervention for a disease exhibiting the disease cell heterogeneity, wherein the therapeutic intervention is effective against a disease having the profile of disease cell heterogeneity determined. In some embodiments, the disease cells are spatially distinct disease cells. In some embodiments, the therapeutic intervention is determined based on a database of interventions shown to be therapeutic for cancers having tumor heterogeneity characterized by each of the somatic mutations.

In an aspect herein is a method of detecting disease cell heterogeneity in a subject comprising: a) quantifying polynucleotides that bear a sequence variant at each of a plurality of genetic loci in polynucleotides from a sample from the subject, wherein the sample comprises polynucleotides from somatic cells and from disease cells; b) determining for each locus a measure of copy number variation (CNV) for polynucleotides bearing the sequence variant; c) determining for each locus a weighted measure of quantity of polynucleotides bearing a sequence variant at the locus as a function of CNV at the locus; and d) comparing the weighted measures at each of the plurality of loci, wherein different weighted measures indicate disease cell heterogeneity. In some embodiments, the disease cells are tumor cells. In some embodiments, polynucleotides comprise cfDNA.

In an aspect provided herein is a method comprising: a) subjecting a subject to one or more pulsed therapy cycles, each pulsed therapy cycle comprising: (i) a first period during which one or more drugs is administered at a first amount and (ii) a second period during which the one or more drugs is administered at a second, reduced (e.g., completely not administered) amount; wherein: (A) the first period is characterized by a tumor burden detected above a first clinical level; and (B) the second period is characterized by a tumor burden detected below a second clinical level. In some embodiments, tumor burden is measured as a function of a quantity of a selected somatic variant in tumor polynucleotides. In some embodiments, one or more drugs is a plurality of drugs and each amount of each drug in each cycle is determined as a function of tumor burden measured as a function of a quantity of each of a plurality of different selected somatic variants in tumor polynucleotides. In some embodiments, the method comprises subjecting the subject to a plurality of pulsed therapy cycles. In some embodiments, the method further comprises: b) when the subject exhibits resistance to the one or more drugs, subjecting the subject to one or more pulsed therapy cycles, each pulsed therapy cycle comprising: (i) a first period during which a different one or more drugs is administered at a first amount and (ii) a second period during which the different one or more drugs is administered at a second, reduced (e.g., completely not administered) amount; wherein: (A) the first period is characterized by a tumor burden detected above a first clinical level; and (B) the second period is characterized by a tumor burden detected below a second clinical level.

In an aspect provided herein is a method comprising: (a) sequencing polynucleotides from cancer cells from a subject; (b) identifying and quantifying somatic mutations in the polynucleotides; and (c) developing a profile of tumor heterogeneity in the subject for use in determining a therapeutic intervention effective for a cancer exhibiting tumor heterogeneity, wherein the profile indicates the presence and relative quantity of a plurality of the somatic mutations in the polynucleotides, wherein different relative quantities indicates tumor heterogeneity.

In an aspect provided herein is a method comprising providing a therapeutic intervention for a subject wherein the therapeutic intervention is determined from a profile of disease cell heterogeneity in the subject, wherein the profile indicates the presence and relative quantity of a plurality of the somatic mutations in the polynucleotides, wherein different relative quantities indicates disease cell heterogeneity; and wherein the therapeutic intervention is effective against a disease having the profile of disease cell heterogeneity determined, e.g., more effective against a disease presenting with the plurality of somatic mutations than it is against a disease presenting with any one, but not all, of the somatic mutations.

In an aspect provided herein is a method comprising: a) determining a measure of deviation from a value of central tendency (e.g., standard deviation, variance) of copy number in polynucleotides in a sample across a region of at least 1 kb, at least 10 kb, at least 100 kb, at least 1 mb, at least 10 mb or at least 100 mb of a genome; b) inferring a measure of burden of DNA from cells undergoing cell division in the sample based on the measure of deviation. In some embodiments, the value of central tendency is mean, median or mode. In some embodiments, determining comprises partitioning the region into a plurality of non-overlapping intervals, determining a measure of copy number at each interval and determining the measure of deviation based on measures of copy number at each interval. In some embodiments, the interval is no more than any of 1 base, 10 bases, 100 bases, 1 kb bases or 10 kb.

In an aspect provided herein is a method of inferring a measure of burden of DNA from cells undergoing cell division in a sample comprising measuring copy number variation induced by proximity of one or more genomic loci to cells' origins of replication, wherein increased CNV indicates cells undergoing cell division. In some embodiments, the burden is measured in cell-free DNA. In some embodiments, the measure of burden relates to the fraction of tumor cells or genome-equivalents of DNA from tumor cells in the sample. In some embodiments, CNV due to proximity to origins of replication is inferred from a set of control samples or cell-lines. In some embodiments, a hidden-markov model, regression model, principal component analysis-based model, or genotype-modified model is used to approximate variations due to origins of replications. In some embodiments, the measure of burden is presence or absence of cells undergoing cell division. In some embodiments, proximity is within 1 kb of an origin of replication.

In an aspect provided herein is a method of increasing sensitivity and/or specificity of determining gene-related copy-number variations by ameliorating the effect of variations due to proximity to origins of replications. In some embodiments, the method comprises measuring CNV at a locus, determining amount of CNV due to proximity of the locus to an origin of replication, and correcting the measured CNV to reflect genomic CNV, e.g., by subtracting amount of CNV attributable to cell division. In some embodiments, the genomic data is obtained from cell-free DNA. In some embodiments, the measure of burden relates to the fraction of tumor cells or genome-equivalents of DNA in a sample. In some embodiments, variations due to origins of replication are inferred from a set of control samples or cell-lines. In some embodiments, a hidden-markov model, regression model, principal component analysis-based model, or genotype-modified model is used to approximate variations due to origins of replications.

In an aspect provided herein is a method comprising: a) determining a baseline measure of copies of DNA molecules at one or more loci from one or more control samples, wherein one or more of the loci includes an origin of replication, each containing DNA from cells undergoing a predetermined level of cell division; b) determining a test measure of DNA molecules in a test sample; wherein the measure in test sample is from one or more loci partitioned into one or more partitions and wherein one or more of the loci includes an origin of replication; c) comparing the test measure and the baseline measure, wherein a test measure above a baseline measure indicates DNA in the test sample from cells dividing at a rate faster than cells providing DNA to the control sample. In some embodiments, the measure is selected from molecule count, a measure of central tendency of molecule count across partitions or a measure of variation of molecule count across partitions.

In an aspect provided herein is a method comprising: (a) administering to a subject an intervention that increases an amount of tumor-derived DNA in the subject's circulation; and (b) when said amount is increased, collecting from the subject a sample containing tumor-derived DNA. In some embodiments, the intervention preferentially kills tumor cells. In some embodiments, the intervention comprises exposing the subject or suspected diseased areas of the subject to radiation. In some embodiments, the intervention comprises exposing the subject or suspected diseased areas of subject to ultrasound. In some embodiments, the intervention comprises exposing the subject or suspected diseased areas of subject to physical agitation. In some embodiments, the intervention comprises administering to the subject a low dose of chemotherapy. In some embodiments, the method comprises administering the intervention to the subject within 1 week before collecting the sample. In some embodiments, the sample is selected from blood, plasma, serum, urine, saliva, cerebral spinal fluid, vaginal secretion, mucous and semen.

In an aspect provided herein is a method comprising compiling a database, wherein the database includes, for each of a plurality of subjects having cancer, tumor genomic testing data, including somatic alterations, collected at two or more time intervals per subject, one or more therapeutic interventions administered to each of the subjects at one or more times and efficacy of the therapeutic interventions, wherein the database is useful to infer efficacy of the therapeutic interventions in subjects with a tumor genomic profile. In some embodiments, the plurality is at least 50, at least 500 or at least 5000. In some embodiments, the tumor genomic testing data is collected via serial biopsy, cell-free DNA, cell-free RNA or circulating tumor cells. In some embodiments, relative frequencies of detected genetic variants are used to classify treatment efficacy. In some embodiments, additional information is used to help classify treatment efficacy, including but not limited to, weight, adverse treatment effects, histological testing, blood testing, radiographic information, prior treatments, and cancer type. In some embodiments, treatment response per patient is collected and classified quantitatively through additional testing. In some embodiments, the additional testing is blood or urine based testing.

In an aspect provided herein is a method comprising use of a database to identify one or more effective therapeutic interventions for a subject having cancer, wherein the database includes, for each of a plurality of subjects having cancer, tumor genomic testing data, including somatic alterations, collected at two or more time intervals per subject, one or more therapeutic interventions administered to each of the subjects at one or more times and efficacy of the therapeutic interventions. In some embodiments, identified therapeutic interventions are stratified by efficacy. In some embodiments, quantitative bounds on predicted therapeutic interventions efficacy or lack thereof are reported. In some embodiments, the therapeutic interventions use information of predicted tumor genomic evolution or acquired resistance mechanisms in similar patients in response to treatment.

In some embodiments, the method comprises classifying effectiveness of treatment using a classification algorithm, e.g., linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (e.g., support vector machines).

In an aspect disclosed herein is a method to report results of one or more genetic tests comprising: capturing genetic information including genetic variants and quantitative measures thereof over one or more test points using a genetic analyzer; normalizing the quantitative measures for rendering with the one or more test points and generating a scaling factor; applying the scaling factor to render a tumor response map; and generating a summary of genetic variants. In some embodiments, the method comprises analyzing non-CNV (copy number variation) mutant allele frequencies. In some embodiments, the method comprises transforming an absolute value into a relative metric for rendering the tumor response map. In some embodiments, the method comprises multiplying a mutant allele frequency by a predetermined value and taking a log thereof. In some embodiments, the method comprises: multiplying the scaling factor by a transformed value for each gene to determine a quantity indicator to be rendered on the tumor response map; and assigning a unique visual indicator for each alteration in a visual panel. In some embodiments, the method comprises Y-centering or vertically centering the quantity indicator in a contiguously placed panel that indicates continuity. In some embodiments, the assigning further comprises providing a unique color for each alteration.

In some embodiments, the method comprises analyzing genetic information from another test point or test time. In some embodiments, wherein a new test result does not differ from a prior test result, the method comprises rendering the prior visual panel. In some embodiments, wherein if alterations remain the same, but quantities have changed, the method comprises: maintaining the order and unique visual indicator for each alteration; and determining a new quantity indicator and generating a new visual panel for all test points. In some embodiments, the method comprises determining a new alteration in the genetic information and adding the alteration to the top of existing alterations. In some embodiments, the method comprises determining a new alteration in the genetic information and determining new transform values and scaling factor and assigning a unique visual indicator for each new alteration. In some embodiments, the method comprises determining a new alteration in the genetic information and re-generating the tumor response map including alterations from a prior test point that are still detected in current test point and the new alteration. In some embodiments, the method comprises determining if a prior alteration is no longer present and if so, comprising using a height of zero when rendering the quantity of the alteration of the prior alteration for subsequent test points. In some embodiments, the method comprises determining if a prior alteration is no longer present and if so, reserving the unique visual indicator associated with the prior alternation from future use.

In some embodiments, the method comprises analyzing CNV mutant allele frequencies and methylation mutant allele frequencies. In some embodiments, the method comprises grouping of maximum mutant allele frequencies for rendering first on the tumor response map. In some embodiments, the method comprises rendering alterations for the gene in decreasing mutant allele frequency order of alterations. In some embodiments, the method comprises rendering alterations for the gene in a decreasing order. In some embodiments, the method comprises selecting a next gene with next highest mutant allele frequency.

In some embodiments, for each reported alteration, the method comprises generating a trend indicator for the alteration over the different test points. In some embodiments, the method comprises generating a summary of alterations. In some embodiments, the method comprises generating a summary of treatment options. In some embodiments, the method comprises generating a summary of mutant allele frequency, cell free amplification, clinical approval indication, and clinical trial. In some embodiments, the method comprises generating a panel based on a biological pathway. In some embodiments, the method comprises generating a panel based on an evidence level. In some embodiments, the genetic information includes one or more of single-nucleotide variations, copy number variations, insertions and deletions, and gene rearrangements. In some embodiments, the method comprises generating a clinical relevance report on detected alterations. In some embodiments, the method comprises generating a therapy result summary.

In an aspect provided herein is a method to generate a genetic report comprising: generating non-copy number variation (CNV) data using a genetic analyzer; determining a scaling factor for each non-CNV mutant allele frequency; for a first test, generating a visual panel each non-CNV alteration using the scaling factor; and for each subsequent test, generating changes in the non-CNV alteration for the visual panel using the scaling factor.

In some embodiments, the method comprises transforming an absolute value into a relative metric for rendering. In some embodiments, the method comprises multiplying a mutant allele frequency by a predetermined value and taking a log of the predetermined value. In some embodiments, the method comprises determining a scaling factor using a maximum observed value. In some embodiments, for each non-CNV alteration, the method comprises multiplying a scaling factor by a transformed value for each gene variant as a quantity indicator for visualizing the gene variant.

In some embodiments, the method comprises assigning a unique visual indicator for each alteration. In some embodiments, for the subsequent test, the method comprises using the visual panel if the test result is unchanged. In some embodiments, if alterations remain the same in the subsequent test, the method comprises maintaining the order and unique visual indicator for each alteration; and recomputing a quantity indicator for visualizing that variant and re-rendering updated values in existing panel(s) and new panel for the latest test. In some embodiments, if new alteration is found in the subsequent test, the method comprises adding the alterations to the top of all existing alterations; computing transform values and the scaling factor; and assigning a unique visual indicator for each new alterations.

In some embodiments, the method comprises: re-rendering alterations in the prior test point and the new alteration; and vertically centering an image of the alterations in a contiguously placed panel that indicates continuity. In some embodiments, if a prior alteration is not present in a subsequent test, the method comprises using a height of zero as the quantity of the alteration for a subsequent rendering. In some embodiments, the method comprises rendering subject or intervention information associated with alteration changes. In some embodiments, the method comprises identifying an alteration with the maximum Mutant Allele Frequency.

In some embodiments, the method comprises: reporting alterations for that gene in decreasing mutant allele frequency order of non-CNV alterations; and reporting CNV alterations for that gene in decreasing order of CNV value. In some embodiments, the method comprises selecting the next gene with next highest non-CNV mutant allele frequency and reporting alterations for that gene in decreasing mutant allele frequency order of non-CNV alterations; and reporting CNV alterations for that gene in decreasing order of CNV value.

In some embodiments, the method comprises rendering a trend indicator for an alteration over different test dates. In some embodiments, the method comprises grouping of maximum mutant allele frequencies and generating annotations including biological pathways or evidence level. In some embodiments, the method comprises generating a panel based on an evidence level. In some embodiments, the method comprises generating a panel based on a biological pathway. In some embodiments, the genetic information includes one or more of single-nucleotide variations, copy number variations, insertions and deletions, and gene rearrangements.

In an aspect provided herein is a method comprising: a) providing a plurality of nucleic acid samples from a subject, the samples collected at serial time points; b) sequencing polynucleotides from the samples to generate sequences; c) determining a quantitative measure of each of a plurality of genetic variants among the polynucleotides in each sample; d) graphically representing by computer relative quantities of genetic variants at each serial time point for those somatic mutations present at a non-zero quantity at least one of the serial time points. In some embodiments, the quantitative measure is the frequency of the genetic variant among all sequences mapping to the same genetic locus. In some embodiments, the relative quantities are represented as a stacked area graph. In some embodiments, the relative quantities are stacked, at the earliest time point, highest to lowest from the bottom to the top of the graph, and wherein a genetic variant first appearing at a non-zero quantity at a later time point is stacked at the top of the graph. In some embodiments, the areas are represented by different colors. In some embodiments, the graphical representation further indicates, for each time point, the quantitative measure of the predominant genetic variant. In some embodiments, the graphical representation further includes a key identifying genetic variants represented on the graph. In some embodiments, graphically representing comprises normalizing and scaling the quantitative measures.

In some embodiments, the polynucleotides comprise cfDNA. In some embodiments, the loci are located in oncogenes. In some embodiments, the plurality of the genetic variants maps to a different gene in the genome. In some embodiments, the plurality of the genetic variants maps to the same gene in the genome. In some embodiments, at least 10 different oncogenes are sequenced.

In some embodiments, determining comprises receiving the sequences into computer memory and using a computer processor to execute software to determine the quantitative measurement. In some embodiments, graphically representing comprises using a computer processor to execute software that transforms the quantitative measures into a graphical format and representing the graphical format on an electronic graphical user interface, e.g., a display screen.

In an aspect provided herein is a method to generate a paper or electronic patient test report from data generated by a genetic analyzer comprising: a) summarizing data from two or more testing time points, whereby a union of all non-zero testing results are reported at each subsequent test point after the first test; and b) rendering the testing results on the paper or electronic patient test report. In some embodiments, summarizing and rendering are performed on a computer by executing code with a computer processor to (i) identify all non-zero testing results, (ii) generate the test report and (iii) display the test report on a graphical user interface.

In an aspect provided herein is a method of graphically representing evolution of genetic variants of a tumor in a subject from data generated by a genetic analyzer comprising: a) generating by computer a stacked representation of genetic variants detected at each of a plurality of time points in the subject, wherein a height or width of each layer in the stack that corresponds to a genetic variant represents a quantitative contribution of the genetic variant to the a total quantity of genetic variants at each time point; and b) displaying the stacked representation on a computer monitor or a paper report. In some embodiments, the method further comprises using a combination of a magnitude of detected genetic variants in a body-fluid based test to infer a disease burden. In some embodiments, the method further comprises using allele fractions of detected mutations, allelic imbalances, gene-specific coverage to infer the disease burden.

In some embodiments, an overall stack height is representative of overall disease burden or a disease burden score in the subject. In some embodiments, a distinct color is used to represent each genetic variant. In some embodiments, only a subset of detected genetic variants is plotted. In some embodiments, the subset is chosen based on likelihood of being a driver alteration or association with increased or reduced response to treatment.

In some embodiments, the method comprises producing a test report for a genomic test. In some embodiments, a non-linear scale is used for representing the heights or widths of each represented genetic variant. In some embodiments, a plot of previous test points is depicted on the report. In some embodiments, the method comprises estimating a disease progression or remission based on rate of change and/or quantitative precision of each testing result. In some embodiments, the method comprises displaying a therapeutic intervention between intervening testing points. In some embodiments, displaying comprises: a) receiving data representing the detected tumor genetic variants into computer memory; b) executing code with a computer processor to graphically represent the quantitative contribution of each genetic variant at a time point as a line or area proportional to the relative contribution; and c) displaying the graphical representation on a graphical user interface.

BRIEF DESCRIPTION OF THE DRAWINGS

FIG. 8 shows an exemplary panel of 70 genes that exhibit genetic variation in cancer.

FIG. 9B shows an exemplary process to reduce error rates and bias in DNA sequence readings and generate genetic reports for users.

FIG. 10A-10C show exemplary processes for reporting genetic test results to users.

FIG. 10D-10I-2 show pages from an exemplary genetic test report.

DETAILED DESCRIPTION

Figure 1:
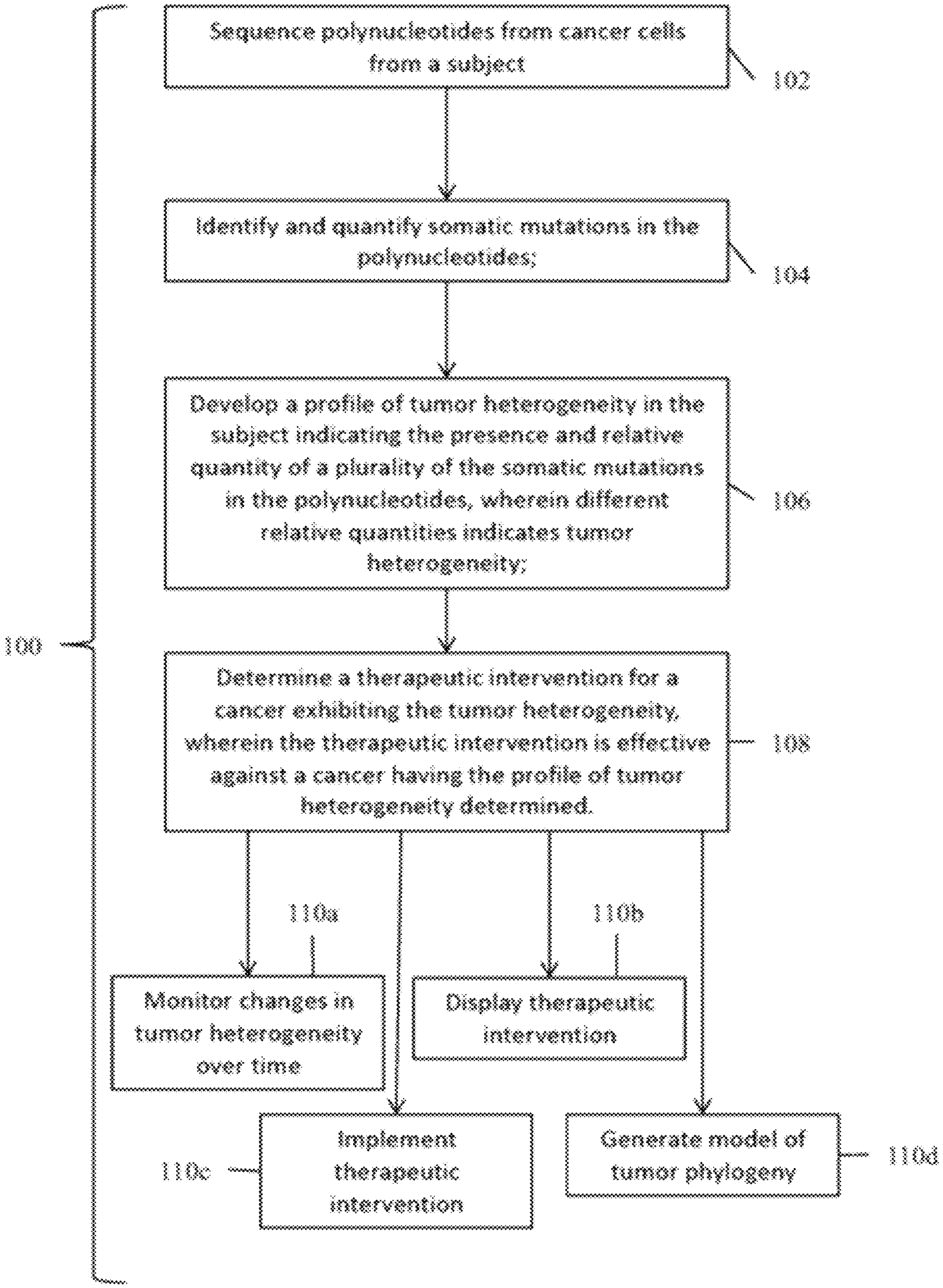
FIG. 1 shows a flow chart of an exemplary method of determination and use of a therapeutic intervention.

Methods of the present disclosure can detect biomolecular mosaicism (e.g., genetic mosaicism) in a biological sample, such as a heterogeneous genomic population of cells or deoxyribonucleic acid (DNA). Genetic mosaicism can exist at the organismal level. For example, genetic variants that arise early in development can result in different somatic cells having different genomes. An individual can be a chimera, e.g., produced by the fusion of two zygotes. Organ transplant from an allogeneic donor can result in genetic mosaics, which also can be detected by examining polynucleotides shed into the blood from the transplanted organ. Disease cell heterogeneity, in which diseased cells have different genetic variants, is another form of genetic mosaicism. Methods provided herein can detect mosaicism and, in the case of disease, provide therapeutic intervention. In certain embodiments, this disclosure provides methods for performing body-wide profiling of biomolecular mosaicism through the use of circulating polynucleotides, which may derive or otherwise originate from cells in diverse locations of the body of a subject.

Diseased cells, such as tumors, may evolve over time, resulting in different clonal sub-populations having new genetic and phenotypic characteristics. This may result from natural mutations as the cells divide, or it may be driven by treatments that target certain clonal sub-populations, allowing clones more resistant to the treatment to proliferate by negative selection. The existence of sub-populations of diseased cells that bear different genotypic or phenotypic characteristics is referred to herein as disease cell heterogeneity, or, in the case of cancer, tumor heterogeneity.

Presently, cancers are treated based on mutant forms found in a cancer biopsy. For example, the finding of Her2+ in even small amounts of breast cancer cells may be indicative of breast cancer, which may be followed through with a treatment using an anti-Her2+ therapy. As another example, a colorectal cancer in which a KRAS mutant is found in small amounts may be treated with a therapy for which KRAS is responsive.

Tools for fine analysis of diseased cells (e.g., tumors), allows detection of disease cell heterogeneity. Furthermore, the analysis of polynucleotides sourced from diseased cells located throughout the body allows for a whole-body profile of disease cell heterogeneity. The use of cell-free DNA, or circulating DNA, is particularly powerful because polynucleotides in the blood are not sourced from physically localized cells. Rather, they include cells from metastatic sites throughout the body. For example, analysis may show that a population of breast-cancer cells includes 90% that are Her2+ and 10% that are Her2−. This may be determined, for example, by quantifying DNA for each form in a sample, e.g., cell free DNA (cfDNA), thereby detecting heterogeneity in the tumor.

This information can be used by a health care provider, e.g., a physician, to develop therapeutic interventions. For example, a subject that has a heterogeneous tumor can be treated as if they had two tumors, and a therapeutic intervention can treat each of the tumors. The therapeutic intervention could include, for example, a combination therapy including a first drug effective against the first tumor type and a second drug effective against the second tumor type. The drugs can be given in amounts that reflect the relative amounts of the mutant forms detected. For example, a drug to treat the mutant form that is found in higher relative amounts can be delivered at greater dose than a drug to treat the mutant form in lesser relative amount. Or, treatment for the mutant in the lesser relative amount can be delayed or staggered with respect the mutant in greater amount.

Monitoring changes in the profile of disease cell heterogeneity over time allows therapeutic intervention to be calibrated to an evolving tumor. For example, analysis may show increasing amounts of polynucleotides bearing drug resistance mutants. In this case, the therapeutic intervention can be modified to decrease the amount of drug effective to treat a tumor that does not bear the resistance mutant and increase administration of a drug that does treat a tumor bearing the resistance marker.

Therapeutic interventions can be determined by a healthcare provider or by a computer algorithm, or a combination of the two. A database can contain the results of therapeutic interventions against diseases having various profiles of disease cell heterogeneity. The database can be consulted in determining a therapeutic intervention for a disease with a particular profile.

This present disclosure provides, among other things, methods of determining a therapeutic intervention for a subject having a disease, such as cancer, that exhibits disease cell heterogeneity, e.g., tumor heterogeneity. In one embodiment, the method involves analyzing biological macromolecules (e.g., sequencing polynucleotides) of disease cells (e.g., spatially distinct disease cells) from a subject having the disease. A profile of disease cell heterogeneity is developed that indicates the existence of genetic variants specific to the disease cells and the amount of these variants relative to each other. This information, in turn, is used to determine a therapeutic intervention that takes the profile into account.

Disease Cells

A subject of the methods of this disclosure is any multicellular organism. More specifically, the subject can be a plant or an animal, a vertebrate, a mammal, a mouse, a primate, a simian or a human. Animals include, but are not limited to, farm animals, sport animals, and pets. A subject can be a healthy individual, an individual that has or is suspected of having a disease or a pre-disposition to the disease, or an individual that is in need of therapy or suspected of needing therapy. A subject can be a patient, e.g., a subject under the care of a professional healthcare provider.

The subject can have a pathological condition (disease). Cells exhibiting pathology of disease are referred to herein as disease cells.

In particular, the disease can be a cancer. Cancer is a condition characterized by abnormal cells that divide out of control. Cancers include, without limitation, carcinomas, sarcomas, leukemias, lymphomas, myelomas and central nervous system cancers. More specific examples of cancers are breast cancer, prostate cancer, colorectal cancer, brain cancer, esophageal cancer, head and neck cancer, bladder cancer, gynecological cancer, liposarcoma, and multiple myeloma.

Other cancers include, for example, acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloepithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chronic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, nonmelanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom macroglobulinemia, and/or Wilms Tumor.

A tumor is a collection of cancer cells (cancer disease cells). This includes, for example, a collection of cells in a single mass of cells (e.g., a solid tumor), a collection of cells from different metastatic tumor sites (metastatic tumors), and diffuse tumors (e.g., circulating tumor cells). A tumor can include cells of a single cancer (e.g., colorectal cancer), or multiple cancers (e.g., colorectal cancer and pancreatic cancer). A tumor can include cells originating from a single original somatic cell or from different somatic cells.

In certain embodiments, disease cells in the subject are spatially distinct. Disease cells are spatially distinct if the cells are located at least 1 cm, at least 2 cm, at least 5 cm or at least 10 cm apart in a body, e.g, in different tissues or organs, or the same tissue or organ. In the case of cancer, examples of spatially distinct cancer cells include cancer cells from diffuse cancers (such as leukemias), cancer cells at different metastatic sites, and cancer cells from the same mass of tumor cells that are separated by at least 1 cm.

Disease cell burden (e.g., "tumor burden") is a quantitative measure of the amount of disease cells in a subject. One measure of disease cell burden is the fraction of total biological macromolecules in a sample that are disease biological macromolecules, e.g., the relative amount of tumor polynucleotides in a sample of cell free polynucleotides. For example, if cfDNA from a first subject has 10% cancer polynucleotides, the subject may be said to have a cell-free tumor burden of 10%, If cfDNA from a second subject has 5% cancer polynucleotides, the a second subject may be said to have half the cell-free tumor burden of the first subject. These measures are much more relevant on an intra-subject basis than on an inter-subject basis, as cell-free tumor burdens in one individual can be much higher or lower than another individual despite differing levels of disease burden. However, these measures can be used quite effectively for monitoring disease burden within an individual, e.g., an increase from a 5% to a 15% cell-free DNA tumor burden may indicate significant progression of disease, while a decrease from 10% to 1% may indicate partial response to treatment.

Polynucleotides to be sequenced can be sourced from spatially distinct sites. This includes polynucleotides sourced from biopsies of different locations in a single tumor mass. It also includes polynucleotides sourced from cells at different metastatic tumor sites. Cells shed polynucleotides into the blood where it is detectable as cell free polynucleotides (e.g., circulating tumor DNA). Cell free polynucleotides also can be found in other bodily fluids such as urine. Therefore, cfDNA provides a more accurate profile of tumor heterogeneity across the entire disease cell population than DNA sourced from a single tumor location. DNA sampled from cells across the disease cell population in a body is referred to as "disease burden DNA" or, in the case of cancer, "tumor burden DNA".

Disease cells, such as tumors, can share the same or similar biomolecular profiles. For example, tumors may share one, two, three or more genetic variants. Such variants may share the same stratification, for example highest frequency, second highest frequency, etc. Profiles can also share similar disease cell burdens, e.g., cfDNA burdens, e.g., within 15%, within 10%, within 5% or within 2%.

Analytes

As used herein, a macromolecule is a molecule formed from monomeric subunits. Monomeric subunits forming biological macromolecules include, for example, nucleotides, amino acids, monosaccharides and fatty acids. Biological macromolecules include, for example, biopolymers and non-polymeric macromolecules.

A polynucleotide is a macromolecule comprising a polymer of nucleotides. Polynucleotides include, for example, polydeoxyribonucleotides (DNA) and polyribonucleotides (RNA). A polypeptide is a macromolecule comprising a polymer of amino acids. A polysaccharide is a macromolecule comprising a polymer of monosaccharides. Lipids are a diverse group of organic compounds including, for example, fats, oils and hormones that share the functional characteristic of not interacting appreciably with water. For example, a triglyceride is a fat formed from three fatty acid chains.

A cancer polynucleotide (e.g., cancer DNA) is a polynucleotide (e.g., DNA) derived from a cancer cell. Cancer DNA and/or RNA can be extracted from tumors, from isolated cancer cells or from biological fluids (e.g., saliva, serum, blood or urine) in the form of cell free DNA (cfDNA) or cell free RNA.

Cell free DNA is DNA located outside of a cell in a bodily fluid, e.g., in blood or urine. Circulating nucleic acids (CNA) are nucleic acids found in the blood stream. Cell free DNA in the blood is a form of circulating nucleic acid. Cell free DNA is believed to arise from dying cells that shed their DNA into the blood. Because spatially distinct cancer cells will shed DNA into bodily fluids, such as blood, cfDNA of cancer subjects typically comprises cancer DNA from spatially distinct cancer cells.

Biological Samples

Analytes for analysis in the methods of this disclosure can derive from a biological sample, e.g., a sample comprising a biological macromolecule. A biological sample can be derived from any organ, tissue or biological fluid. A biological sample can comprise, for example, a bodily fluid or a solid tissue sample. An example of a solid tissue sample is a tumor sample, e.g., from a solid tumor biopsy. Bodily fluids include, for example, blood, serum, tumor cells, saliva, urine, lymphatic fluid, prostatic fluid, seminal fluid, milk, sputum, stool and tears. Bodily fluids are particularly good sources of biological macromolecules from spatially distinct disease cells, as such cells from many locations in a body can shed these molecules into the bodily fluid. For example, blood and urine are good sources of cell free polynucleotides. Macromolecules from such sources can provide a more accurate profile of the diseased cells than macromolecules derived from a localized disease cell mass.

Amounts of disease polynucleotides in a bodily fluid sample can be increased. Such increases can increase sensitivity of detection of disease polynucleotides. In one method, an intervention, such as a therapeutic intervention, is administered to a subject that causes disease cells to lyse, emptying their DNA into the surrounding fluid. Such interventions can include administration of chemotherapy. It also can include administering radiation or ultrasound to the whole body of a subject, or to a portion of the body of a subject, such as being directed to a tumor or a diseased organ. After administration of the intervention and when the amount disease polynucleotides in the fluid is increased, a fluid sample is collected for analysis. The interval between administration of the intervention and collection can be long enough for the disease polynucleotides to increase, but not so long that they are cleared from the body. For example, a low dose of chemotherapy can be administered about a week before collection of the sample.

Analytic Methods

This disclosure contemplates several types of biomolecular analysis including, for example, genomic, epigenetic (e.g., methylation), RNA expression and proteomic. Genomic analysis can be performed by, for example, a genetic analyzer, e.g., using DNA sequencing. Methylation analysis can be performed by, for example, conversion of methylated bases followed by DNA sequencing. RNA expression analysis can be performed by, for example, polynucleotide array hybridization. Proteomic analysis can be performed by, for example, mass spectrometry.

As used herein, the term "genetic analyzer" refers to a system including a DNA sequencer for generating DNA sequence information and a computer comprising software that performs bioinformatic analysis on the DNA sequence information. Bioinformatic analysis can include, without limitation, assembling sequence data, detecting and quantifying genetic variants in a sample, including either of germline variants (e.g., heterozygosity) and somatic cell variants (e.g., cancer cell variants).

Analytic methods can include generating and capturing genetic information. Genetic information can include genetic sequence information, ploidy states, the identity of one or more genetic variants, as well as a quantitative measure of the variants. The term "quantitative measure" refers to any measure of quantity including absolute and relative measures. A quantitative measure can be, for example, a number (e.g., a count), a percentage, a frequency, a degree or a threshold amount.

Polynucleotides can be analyzed by any method known in the art. Typically, the DNA sequencer will employ next generation sequencing (e.g., Illumina, 454, Ion torrent, SOLiD). Sequence analysis can be performed by massively parallel sequencing, that is, simultaneously (or in rapid succession) sequencing any of at least 100,000, 1 million, 10 million, 100 million, or 1 billion polynucleotide molecules. Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxam-Gilbert or Sanger sequencing, primer walking, sequencing using PacBio, SOLiD, Ion Torrent, Genius (GenapSys) or Nanopore (e.g., Oxford Nanopore) platforms and any other sequencing methods known in the art.

The DNA sequencer can apply Gilbert's sequencing method based on chemical modification of DNA followed by cleavage at specific bases, or it can apply Sanger's technique which is based on dideoxynucleotide chain termination. The Sanger method became popular due to its increased efficiency and low radioactivity. The DNA sequencer can use techniques that do not require DNA amplification (polymerase chain reaction—PCR), which speeds up the sample preparation before sequencing and reduces errors. In addition, sequencing data is collected from the reactions caused by the addition of nucleotides in the complementary strand in real time. For example, the DNA sequencers can utilize a method called Single-molecule real-time (SMRT), where sequencing data is produced by light (captured by a camera) emitted when a nucleotide is added to the complementary strand by enzymes containing fluorescent dyes.

Sequencing of the genome can be selective, e.g., directed to portions of the genome of interest. For example, many genes (and mutant forms of these genes) are known to be associated with various cancers. Sequencing of select genes, or portions of genes may suffice for the analysis desired. Polynucleotides mapping to specific loci in the genome that are the subject of interest can be isolated for sequencing by, for example, sequence capture or site-specific amplification.

A nucleotide sequence (e.g., DNA sequence) can refer to raw sequence reads or processed sequence reads, such as unique molecular counts inferred from raw sequence reads.

Sequence reads generated from sequencing are subject to analysis including, for example, identifying genetic variants. This can include identifying sequence variants and quantifying numbers of base calls at each locus. Quantifying can involve, for example, counting the number of reads mapping to a particular genetic locus. Different numbers of reads at different loci can indicate copy number variation (CNV).

Sequencing and bioinformatics methods that reduce noise and distortion are particularly useful when the number of target polynucleotides in a sample is small compared with non-target polynucleotides. When the target molecules are few in number, the signal from the target may be weak. This can be the case, for example, in the case of cell free DNA, where a small number of tumor polynucleotides may be mixed with a much larger number of polynucleotides from healthy cells. Molecular tracking methods can be useful in such situations. Molecular tracking involves tracking sequence reads from a sequencing protocol back to molecules in an original sample (e.g., before amplification and/or sequencing) from which the reads are derived. Certain methods involve tagging molecules in such a way that multiple sequence reads produced from original molecules can be grouped into families of sequences derived from original molecules. In this way, base calls representing noise can be filtered out. Such methods are described in more detail in, for example, WO 2013/142389 (Schmitt et al.), US 2014/0227705 (Vogelstein et al.) and WO 2014/149134 (Talasaz et al.). Up-sampling methods also are useful to more accurately determine counts of molecules in a sample. In some embodiments, up-sampling methods involve determining a quantitative measure of individual DNA molecules for which both strands (Watson and Crick strands) are detected; determining a quantitative measure of individual DNA molecules for which only one of the DNA strands is detected; inferring from these measures a quantitative measure of individual DNA molecules for which neither strand was detected; and using these measures to determine the quantitative measure indicative of a number of individual double-stranded DNA molecules in the sample. This method is described in more detail in PCT/US2014/072383, filed Dec. 24, 2014.

Genetic Variants

Methods of the present disclosure can be used in the detection of genetic variants (also referred to a "gene alterations"). Genetic variants are alternative forms at a genetic locus. In the human genome, approximately 0.1% of nucleotide positions are polymorphic, that is, exist in a second genetic form occurring in at least 1% of the population. Mutations can introduce genetic variants into the germ line, and also into disease cells, such as cancer. Reference sequences, such as hg19 or NCBI Build 37 or Build 38, intend to represent a "wild type" or "normal" genome. However, to the extent they have a single sequence, they do not identify common polymorphisms which may also be considered normal.

Genetic variants include sequence variants, copy number variants and nucleotide modification variants. A sequence variant is a variation in a genetic nucleotide sequence. A copy number variant is a deviation from wild type in the number of copies of a portion of a genome. Genetic variants include, for example, single nucleotide variations (SNPs), insertions, deletions, inversions, transversions, translocations, gene fusions, chromosome fusions, gene truncations, copy number variations (e.g., aneuploidy, partial aneuploidy, polyploidy, gene amplification), abnormal changes in nucleic acid chemical modifications, abnormal changes in epigenetic patterns and abnormal changes in nucleic acid methylation.

Genetic variants can be detected by comparing sequences from polynucleotides in a sample to a reference, e.g., to a reference genome sequence, to an index or to a database of known mutations. In one embodiment, the reference sequence is a publicly available reference sequence, such as the human genome sequence HG-19 or NCBI Build 37. In another embodiment, the reference sequence is a sequence in a non-public database. In another embodiment, the reference sequence is a germ line sequence of an organism inferred or determined from sequencing polynucleotides from the organism.

A somatic mutation or somatic alteration is a genetic variant that arises in a somatic cell. Somatic mutations are distinguished from mutations that arise in the genome of a germ line cell (i.e., sperm or egg) or a zygote, of an individual. Somatic mutations, e.g., those found in cancer cells, are distinguishable from the germ line genome of a subject in which the cancer arose. They also can be detected by comparing the cancer genome with the germ line genome or with a reference genome. There also are known genetic variants that are common in cancer cells. A database of SNVs in human cancer can be found at the website: cancer.sanger.ac.uk/cancergenome/projects/cosmic/.

FIG. 8 shows genes known, in cancer, to exhibit point mutations, amplifications, fusions and indels.

CNV Deviation in Rapidly Dividing Cells

During the S phase of the cell cycle, the cell replicates DNA. A diploid cell having 2N chromosomes with replicated DNA may correspond to about 4×DNA content, whereas a diploid cell having 2N chromosomes without replicated DNA may correspond to about 2×DNA content. Replication proceeds from origins of replication. In mammals, origins of replication are spaced at intervals of about 15 kb to 300 kb. During this period, portions of the genome exist in polyploid form. Those areas between origins of replication and the position of the polymerase are duplicated, while those areas beyond the position of the polymerase (or just before the origin of replication) are still in single copy number in the strand undergoing replication. When scanned across the genome, copy number appears uneven or distorted, having regions that exist in polyploidy form and regions that exist in diploid form. Such a scan appears noisy. This is true even for cells that do not bear copy number variations in the genome in the resting state. In contrast, a scan of CNV in cells in Go shows a profile in which copy number is relatively flat or undistorted across the genome. Because cancer cells divide rapidly, their CNV profile across the genome exhibits distortion, whether or not the genome also bears CNVs at certain loci.

One can take advantage of this fact to detect tumor burden in DNA from samples comprising heterogeneous DNA, e.g., a mixture of disease DNA and healthy DNA, such as cfDNA. One method to detect tumor burden involves determining copy-number variation due to proximity of examined locus or loci to various origins of replication. Regions that include a replication origin will have very close to 4 copies of DNA in that locus (in a diploid cell), while regions that are far removed from a replication origin will have closer to 2 copies (in a diploid cell). In certain embodiments, the examined locus or loci include, at least 1 kb, at least 10 kb, at least 100 kb, at least 1 mb, at least 10 mb, at least 100 mb, across an entire chromosome or across an entire genome. A measure of replication origin CNV (ROCNV) across the region is determined. This can be, for example, a measure of deviation in copy number from a value of central tendency. The value of central tendency can be, for example, mean, median or mode. The measure of deviation can be for example, variance or standard deviation. This measure can be compared with a measure of ROCNVs across the same region in a control sample, e.g., from a healthy individual or cells in resting state. ROCNVs can be determined by partitioning the region or regions analyzed into non-overlapping partitions of various lengths and taking a measure of CNV in this partition. This measure of CNV can be derived from the number of reads or fragments determined to map to those regions after sequencing. The partitions can have various sizes, to produce various levels of resolution, e.g., a single base level (base-per-base), 10 bases, 100 bases, 1 kb, 10 kb or 100 kb. Deviations that are greater than a control indicate the presence of DNA undergoing replication, which, in turn, indicates malignancy. The greater the degree of deviation, the greater the amount of DNA from cells undergoing cell division in the sample.

Various methods can be used to calculate true genetic copy number variations that differ from replication origin based distortion. For example, heterozygous SNP positions at affected CNV loci can be used to infer copy number variation by calculating the deviation from 50% or the allelic imbalance at those loci. Distortion due to replication origin proximity should not affect this imbalance since both copies would generally be copied at similar time intervals and thus self-normalizing (although allelic changes could conceivably change the replication of origin between the two allelic variants). For example, duplication of a chromosome segment containing a SNP could be detected in around 67% of reads, while duplication resulting from ROCNV would be detected in about 50% of reads. In another method, counting-based techniques that use the density of detected fragments or reads at a certain locus are used to calculate relative copy number. These techniques are generally limited by poisson noise and systematic bias due to DNA sample preparation and sequencing bias. A combination of these methods may also be to obtain even greater accuracy.

ROCNV can be calculated for a given sample and be used to give a value on cell-free tumor burden despite lack of detection of traditional somatic variants, such as, SNVs, gene-specific CNVs, genomic rearrangements, epigenetic variants, loss of heterozygosity, etc. ROCNVs can also be used to subtract distortion for a given sample to increase sensitivity and/or specificity of a given CNV detection/estimation method by removing variation that is related to replication origin proximity rather than due to true copy number changes in a cell. Cell-lines with known or no copy number changes over a reference can also be used as a reference of ROCNVs for use in estimating its contribution to a given sample.

In one embodiment, the method involves determining a baseline level of copies of DNA molecules at one or more loci from one or more control samples, each containing DNA from cells undergoing a predetermined level of cell division, e.g., cells in resting state or rapidly dividing tumor cells. A measure of copies of DNA molecules in a test sample is also determined. The measure in test samples can be from one or more loci partitioned into one or more partitions. In each case, a plurality of loci each include an origin or replication. The measure of copies from the test sample can be an average across all partitions, or a level of variance across loci. A measure of central tendency or of variation (e.g., variance or standard deviation) in copy number in the test sample is compared to the control sample. A measure that is greater in a test sample than in a control of cells in resting state, or slowly dividing, indicates that cells generating the DNA in the test sample are dividing more rapidly than cells providing DNA to the control sample, e.g., are cancerous. Similarly, measures that are similar between a test sample and a control of cells in actively dividing state, indicates that cells generating the DNA in the test sample are dividing at a rate similar to the rapidly dividing cells, e.g., are cancerous.

Disease Cell Heterogeneity

Disease cell heterogeneity, e.g., tumor heterogeneity, is the occurrence of diseased cells having different genetic variants. Disease cell heterogeneity can be determined by examination of polynucleotides isolated from diseased cells and detection of differences in their genomes. Disease cell heterogeneity also can be inferred from examination of polynucleotides from a sample containing polynucleotides from both diseased and healthy cells based on differences in relative frequency of somatic mutations. For example, cancer is characterized by changes at the genetic level, e.g., through the accumulation of somatic mutations in different clonal groups of cells. These changes can contribute to unregulated growth of the cancer cells, or function as markers of responsiveness or non-responsiveness to various therapeutic interventions.

Tumor heterogeneity is a condition in which a tumor characterized by cancer cells containing different combinations of genetic variants, e.g., different combinations of somatic mutations. That is, the tumor can have different cells containing alterations in different genes, or containing different alterations in the same gene. For example, a first cell could include a mutant form of BRAF, while a second cell could include mutant forms of both BRAF and ERBB2. Alternatively, a first cancer cell could include the single nucleotide polymorphism EGRF 55249063 G>A, while a second cell could include the single nucleotide polymorphism EGRF 55238874 T>A. (Numbers refer to nucleotide position in genomic reference sequence.)

For example, an original tumor cell can include a genetic variant in a gene, e.g., an oncogene. As the cells continue to divide, some progeny cells, which carry the original mutation, may independently develop genetic variants in other genes or in different parts of the same gene. In subsequent divisions, tumor cells can accumulate still more genetic variants.

Profile of Disease Heterogeneity

Methods of this disclosure allow quantitative as well as qualitative profiling of disease mosaicism, e.g., tumor heterogeneity. In one embodiment, the profile includes information from polynucleotides from spatially distinct disease cells. In one embodiment, the profile is a whole body profile containing information from cells distributed throughout the body. Analysis of polynucleotides in cfDNA allows sampling of DNA across the entire geographic extent of a tumor, in contrast with sampling of a localized area of a tumor. In particular, it allows sampling of diffuse and metastatic tumors. This contrasts with methods that detect the mere existence of tumor heterogeneity through the localized sampling of a tumor. The profile can indicate the exact nucleotide sequence of the variant, or may simply indicate a gene bearing the somatic mutation.

In one embodiment of a profile of disease cell heterogeneity, such as tumor cell heterogeneity, the profile identifies genetic variations and the relative amounts of each variant. From this information, one can infer possible distributions of the variants in different cell sub-population. For example, a cancer may begin with a cell bearing somatic mutation X. As a result of clonal evolution, some progeny of this cell may develop variant Y. Other progeny may develop variant Z. At the cellular level, after analysis, the tumor may be characterized as 50% X, 35% XY and 15% XZ. At the DNA level (and considering DNA from tumor cells only), the profile may indicate 100% X, 35% Y and 15% Z. One may also detect both CNV at a first locus and sequence variants at a second locus.

Tumor heterogeneity can be detected from analysis of sequences of cancer polynucleotides, based on the existence of genomic variations at different loci occurring at different frequencies. For example, in a sample of cell free DNA (which is likely to contain germ line DNA as well as cancer DNA), it may be found that a sequence variant of BRAF occurs at a frequency of 17%, a sequence variant of CDKN2A occurs at a frequency of 6%, a sequence variant of ERBB2 occurs at a frequency of 3% and a sequence variant of ATM occurs at a frequency of 1%. These different frequencies of sequence variants indicate tumor heterogeneity. Similarly, genetic sequences exhibiting different amounts of copy number variation also indicate tumor heterogeneity. For example, analysis of a sample may show different levels of amplification for the EGFR and CCNE1 genes. This also indicates tumor heterogeneity.

In the case of cell free DNA, detection of somatic mutations can be made by comparing base calls in the sample to a reference sequence or, internally, as less frequent base calls to more common base calls, presumed to be in the germ line sequence. In either case, the existence of subdominant forms (e.g., less than 40% of total base calls) at different loci and at different frequency indicates disease cell heterogeneity.

Cell free DNA typically comprises a preponderance of DNA from normal cells having the germ line genome sequence and, in the case of a disease, such as cancer, a small percentage of DNA from cancer cells and having a cancer genome sequence. Sequences generated from polynucleotides in a sample of cfDNA can be compared with a reference sequence to detect differences between the reference sequence and the polynucleotides in the cfDNA. At any locus, all or nearly all of the polynucleotides from a test sample may be identical to a nucleotide in the reference sequence. Alternatively, a nucleotide detected at nearly 100% frequency in a sample may be different than a nucleotide in the reference sequence. This most likely indicates a normal polymorphic form at this locus. If a first nucleotide that matches a reference nucleotide is detected at about 50% and a second nucleotide that is different than a reference nucleotide is detected at about 50%, this most likely indicates normal heterozygosity. Heterozygosity may present at allele ratios divergent from 50:50, e.g., 60:40 or even 70:30. However, if the sample comprises a nucleotide detectable above noise at a frequency below (of above) an unambiguously heterozygote range (for example, less than about 45%, less than 40%, less than 30%, less than 20%, less than 10% or less than 5%), this can be attributed to the existence of somatic mutations in a percentage of the cells contributing DNA to the cfDNA population. These may come from disease cells, e.g., cancer cells. (The exact percentage is a function of tumor load.) If the frequency of somatic mutations at two different genetic loci are different, e.g., 16% at one locus and 5% at another locus, this indicates that the disease cells, e.g., the cancer cells, are heterogeneous.

In the case of DNA from solid tumors, which is expected to predominantly comprise tumor DNA, somatic mutations also can be detected by comparison to a reference sequence. Detection of somatic mutations that exist in 100% of the tumor cells may require reference to a standard sequence or information about known mutants to. However, the existence of sub-dominant sequences among the polynucleotide pool at different loci and at different relative frequencies, indicates tumor heterogeneity.

The profile may include genetic variants in genes that are known to be actionable. Knowledge of such variants can contribute to selecting therapeutic interventions, as therapies can be targeted to such variants. In the case of cancer, many actionable genetic variants are already known.

CNV and SNV in Disease Cell Heterogeneity

In general, the copy number state of a gene should be reflected in the frequency of a genetic form of the gene in the sample. For example, a sequence variant may be detected at a frequency consistent with homozygosity or heterozygosity (e.g., about 100% or about 50%, respectively) with no copy number variation. This is consistent with a germ line polymorphism or mutation. A sequence variant may be detected at frequency of about 67% (or, alternatively, at about 33%) of polynucleotides at a locus, and also in a gene measured at increased copy number (generally, n=2), This is consistent with gene duplication in the germ line. For example, a trisomy would present in this fashion. However, if a sequence variant is detected at a level consistent with homozygosity (e.g., about 100%) but at amounts consistent with copy number variation, this is more likely to reflect the presence of disease cell polynucleotides having undergone gene amplification. Similarly, if a sequence variant is detected at a level not inconsistent with heterozygosity (e.g., deviating somewhat from 50%) but at amounts consistent with copy number variation, this also is more likely to reflect the presence of disease cell polynucleotides; the diseased polynucleotides create some level of imbalance in allele frequency away from 50:50.

This observation can be used to infer whether a sequence variant is more likely present in the germ line level or resulted from a somatic cell mutation, e.g., in a cancer cell. For example, a sequence variant in a gene detected at levels arguably consistent with heterozygosity in the germ line is more probably the product of a somatic mutation in disease cells if copy number variation also is detected in that gene.

Also, to the extent we expect that a gene duplication in the germ line should bear a variant consistent with increased genetic dose (e.g., about 67% for trisomy at a locus), detection gene amplification with a sequence variant dose that deviates significantly from this expected amount indicates that the CNV is more likely present as a result of somatic cell mutation.

The fact that somatic mutations at different loci may be present at single or multiple copy number in the same disease cell also can be used to infer tumor heterogeneity. More specifically, tumor heterogeneity can be inferred when two genes are detected at different frequency but their copy number is relatively equal. Alternatively, tumor homogeneity can be inferred when the difference in frequency between two sequence variants is consistent with difference in copy number for the two genes. Thus, if an EGFR variant is detected at 11% and a KRAS variant is detected at 5%, and no CNV is detected at these genes, the difference in frequency likely reflects tumor heterogeneity (e.g., all tumor cells carry an EGFR mutant and half the tumor cells also carry a KRAS mutant). Alternatively, if the EGFR gene carrying the mutant is detected at increased copy number, one consistent interpretation is a homogenous population of tumor cells, each cell carrying a mutant in the EGFR and KRAS genes, but in which the KRAS gene is duplicated. Accordingly, both the frequency of a sequence variant and a measure of CNV at the locus of the sequence variant in a sample can be determined. The frequency can then be corrected to reflect the relative number of cells bearing the variant by weighing the frequency based on dose per cell determined from the measure of CNV. This result is now more comparable in terms of number of cells carrying the variant to a sequence variant that does not vary in copy number.

Communicating Test Results

A report of results from genetic variant analysis (e.g., sequence variants, CNV, disease cell heterogeneity, and combinations thereof) may be provided by a report generator, for example to a healthcare practitioner, e.g., a physician, to aid the interpretation of the test results (e.g., data) and selection of treatment options. A report generated by a report generator may provide additional information, such as clinical lab results, that may be useful for diagnosing disease and selecting treatment options.

Figure 9A:
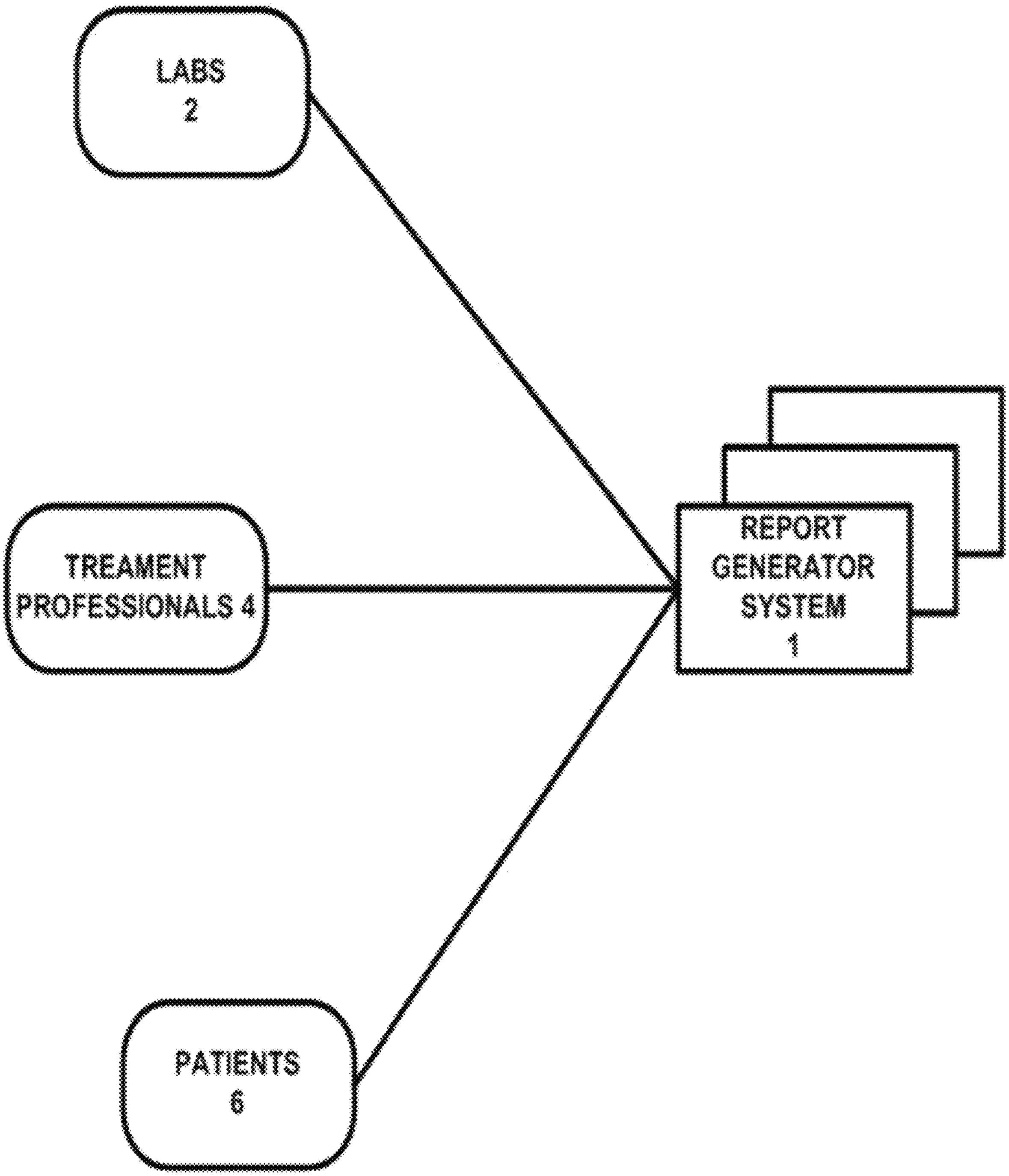
FIG. 9A shows an exemplary system for communicating cancer test results.

Referring now to FIG. 9A, a system with a report generator 1 for reporting on, e.g., cancer test results and treatment options therefrom is schematically illustrated. The report generator system can be a central data processing system configured to establish communications directly with: a remote data site or lab 2, a medical practice/healthcare provider (treating professional) 4, and/or a patient/subject 6 through communication links. The lab 2 can be medical laboratory, diagnostic laboratory, medical facility, medical practice, point-of-care testing device, or any other remote data site capable of generating subject clinical information. Subject clinical information includes but it is not limited to laboratory test data, e.g., analysis of genetic variants; imaging and X-ray data; examination results; and diagnosis. The healthcare provider or practice 6 may include medical services providers, such as doctors, nurses, home health aides, technicians and physician's assistants, and the practice may be any medical care facility staffed with healthcare providers. In certain instances the healthcare provider/practice is also a remote data site. Where cancer is a disease to be treated, the subject may be afflicted with cancer, among other possible diseases or disorders.

Other clinical information for a cancer subject 6 can include the results of laboratory tests, e.g., analysis of genetic variants, metabolic panel, complete blood count, etc.; medical imaging data; and/or medical procedures directed to diagnosing the condition, providing a prognosis, monitoring the progression of the disease, determining relapse or remission, or combinations thereof. The list of appropriate sources of clinical information for cancer includes, but it is not limited to, CT scans, MRI scans, ultrasound scans, bone scans, PET Scans, bone marrow test, barium X-ray, endoscopies, lymphangiograms, IVU (Intravenous urogram) or IVP (IV pyelogram), lumbar punctures, cystoscopy, immunological tests (anti-malignin antibody screen), and cancer marker tests.

The subject 6's clinical information may be obtained from the lab 2 manually or automatically. Where simplicity of the system is desired, the information may be obtained automatically at predetermined or regular time intervals. A regular time interval can refer to a time interval at which the collection of the laboratory data is carried out automatically by the methods and systems described herein based on a measurement of time such as hours, days, weeks, months, years etc. In one embodiment, the collection of data and processing is carried out at least once a day. In one embodiment, the transfer and collection of data is carried out about any of monthly, biweekly, weekly, several times a week or daily. Alternatively the retrieval of information may be carried out at predetermined time intervals, which may not be regular time intervals. For instance, a first retrieval step may occur after one week and a second retrieval step may occur after one month. The transfer and collection of data can be customized according to the nature of the disorder that is being managed and the frequency of required testing and medical examinations of the subjects.

FIG. 9B shows an exemplary process to generate genetic reports, including a tumor response map and associated summary of alterations. A tumor response map is a graphical representation of genetic information indicating changes over time in genetic information from a tumor, e.g., qualitative and quantitative changes. Such changes can reflect response of a subject to a therapeutic intervention. This process can reduce error rates and bias that may be orders of magnitude higher than what is required to reliably detect de novo genetic variants associated with cancer. The process can comprise first capturing genetic information by collecting body fluid samples as sources of genetic material (e.g., blood, saliva, sweat, urine, etc). Then, the process can comprise sequencing the materials (11). For example, polynucleotides in a sample can be sequenced, producing a plurality of sequence reads. The tumor burden in a sample that comprises polynucleotides can be estimated as the relative number of sequence reads bearing a variant to the total number of sequence reads generated from the sample. Where copy number variants are analyzed, the tumor burden can be estimated as the relative excess (e.g., in the case of gene duplication) or relative deficit (e.g., in the case of gene elimination) of the total number of sequence reads at test and control loci. For example, a run may produce 1000 reads mapping to an oncogene locus of which 900 correspond to wild type and 100 correspond to a cancer mutant, indicating a copy number variant at this gene. More details on exemplary specimen collection and sequencing of the genetic materials are discussed below in FIGS. 10-11.

Next, genetic information can be processed (12). Genetic variants can then be identified. The process can comprise determining the frequency of genetic variants in the sample containing the genetic material. The process can comprise separating information from noise (13) if this process is noisy.

The sequencing methods for genetic analysis may have error rates. For example, the mySeq system of Illumina can produce percent error rates in the low single digits. For 1000 sequence reads mapping to a locus, about 50 reads (about 5%) may be expected to include errors. Certain methodologies, such as those described in WO 2014/149134 can significantly reduce the error rate. Errors create noise that can obscure signals from cancer present at low levels in a sample. For example, if a sample has a tumor burden at a level around the sequencing system error rate, e.g., around 0.1%-5%, it may be difficult to distinguish a signal corresponding to a genetic variant due to cancer from one due to noise.

Analysis of genetic variants may be used for diagnosing in the presence of noise. The analysis can be based on the frequency of Sequence Variants or Level of CNV (14) and a diagnosis confidence indication or level for detecting genetic variants in the noise range can be established (15).

Next, the process can comprise increasing the diagnosis confidence. This can be done using a plurality of measurements to increase confidence of diagnosis (16), or alternatively using measurements at a plurality of time points to determine whether cancer is advancing, in remission or stabilized (17). The diagnostic confidence can be used to identify disease states. For example, cell free polynucleotides taken from a subject can include polynucleotides derived from normal cells, as well as polynucleotides derived from diseased cells, such as cancer cells. Polynucleotides from cancer cells may bear genetic variants, such as somatic cell mutations and copy number variants. When cell free polynucleotides from a sample from a subject are sequenced, these cancer polynucleotides are detected as sequence variants or as copy number variants.

Measurements of a parameter, whether or not they are in the noise range, may be provided with a confidence interval. Tested over time, one can determine whether a cancer is advancing, stabilized or in remission by comparing confidence intervals over time. When confidence intervals overlap, one may not be able to tell whether disease is increasing or decreasing, because there is no statistically significant difference between the measures. However, where the confidence intervals do not overlap, this indicates the direction of disease. For example, comparing the lowest point on a confidence interval at one time point and the highest point on a confidence interval at a second time point indicates the direction.

Next, the process can comprise generating genetic Report/Diagnosis. The process can comprise generating genetic graph for a plurality of measurements showing mutation trend (18) and generating report showing treatment results and options (19).

Figure 10A:
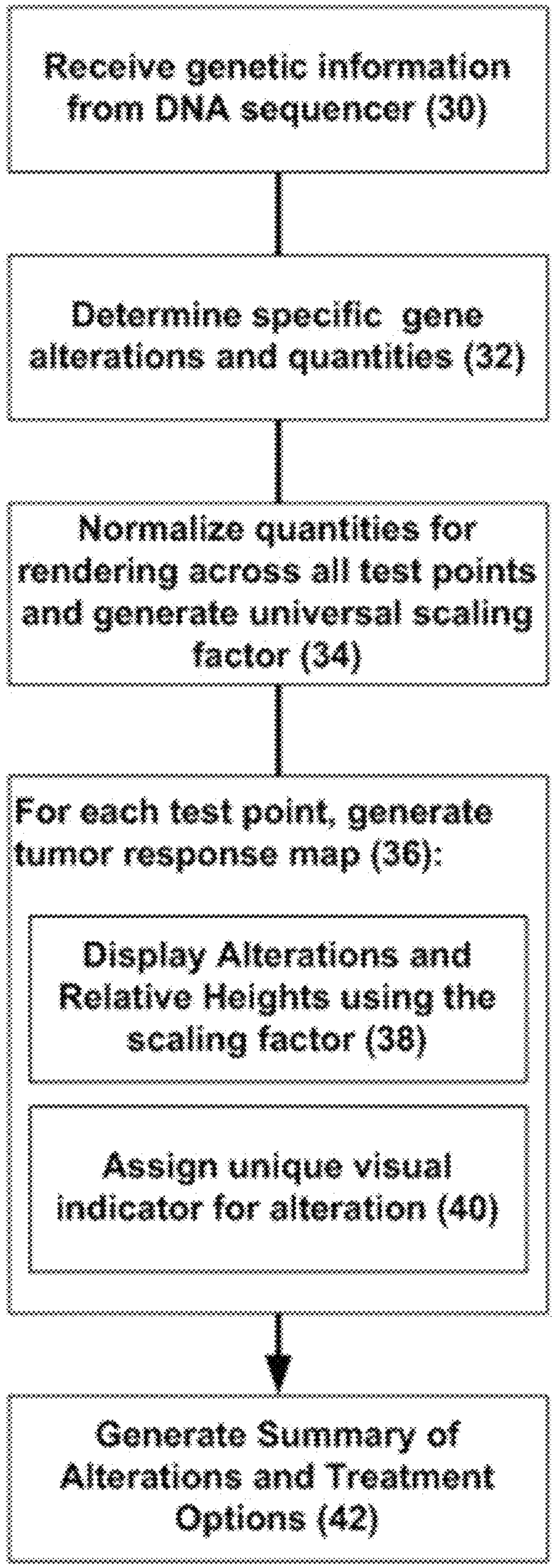
Figure 10B:
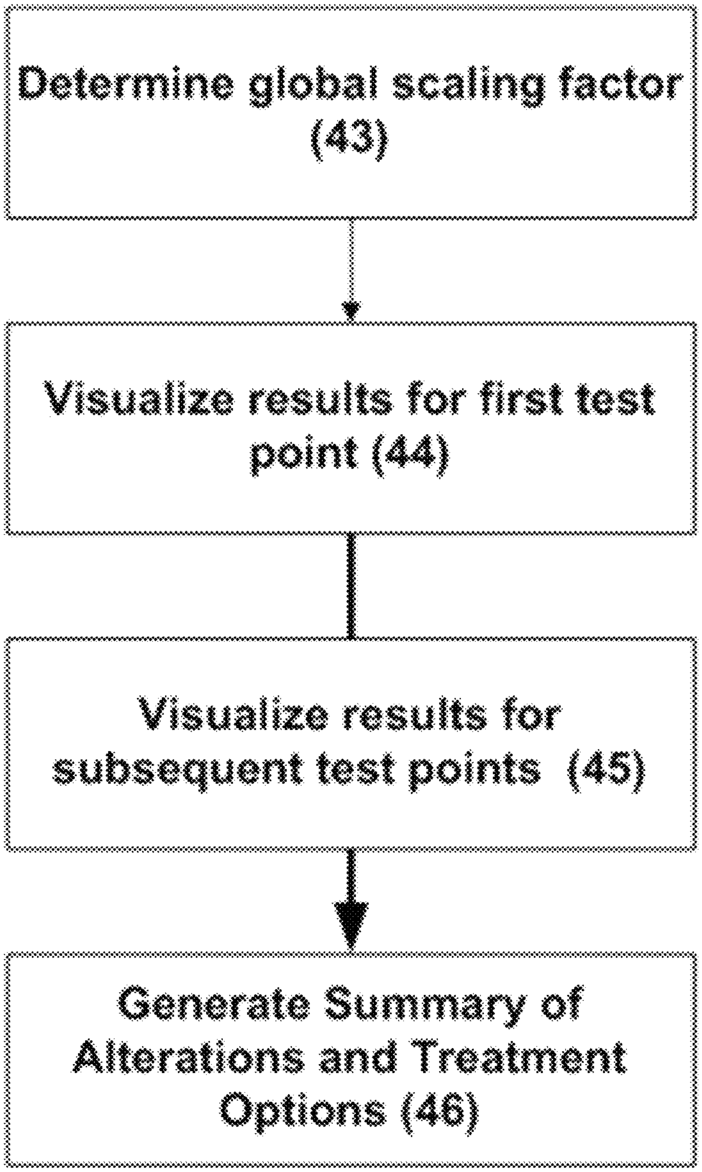

FIGS. 10A-10C show in more details one embodiment for generating genetic reports and diagnosis (e.g., Report/Diagnosis). In one implementation, FIG. 10C shows an exemplary pseudo-code executed by the system of FIG. 9A to process non-CNV reported mutant allele frequencies. However, the system can process CNV reported mutant allele frequencies as well.

Samples comprising genetic material, such as cfDNA, can be collected from a subject at a plurality of time points, that is, serially. The genetic material can be sequenced, e.g., using a high-throughput sequencing system. Sequencing can target loci of interest to detect genetic variants, such genes bearing somatic mutations, genes that undergo copy number variation, or genes involved in gene fusions, for example, in cancer. At each time point, a quantitative measure of the genetic variants found can be determined. For example, in the case of cfDNA, the quantitative measure can be the frequency or percentage of a genetic variant among polynucleotides mapping to a locus, or the absolute number of sequence reads or polynucleotides mapping to a locus. Genetic variants having a non-zero quantity at at least one time point can then be represented graphically through all time points. For example, in a collection of 1000 sequences, variant 1 may be found at time points 1, 2 and 3 in amounts of 50, 30 and 0, respectively. Variant 2 may be found in amounts 0, 10 and 20 at these time points. These amounts can be normalized, for variant 1, to 5%, 3% and 0%, and, for variant 2, 0%, 1% and 2%. A graphical representation showing the union of all non-zero results can indicate these amounts for both variants at all of the time points. The normalized amounts can be scaled so that each percentage is represented by a layer, for example, having height 1 mm. So, for example, in this case the heights would be at time point 1: heights 5 mm (variant 1) and 0 mm (variant 2); at time point 2: heights 3 mm (variant 1) and 1 mm (variant 2), at time point 3: heights 0 mm (variant 1) and 2 mm (variant 2). The graphical representation can be in the form of a stacked area graph, such as a streamgraph. A "zero" time point (before the first time point) can be represented by a point, with all values at 0. The height of the quantity of the variants in the graphical representation can be, for example, relative or proportional to each other. For example, a variant frequency 5% at one time point could be represented with a height of twice that of a variant with frequency of 2.5% at the same time point. The order of stacking can be chosen for ease of understanding. For example, variants can be stacked in order of quantity high to low from bottom to top. Or, they can be stacked in a streamgraph with the variant of largest initial amount in the middle, and other variants of decreasing quantity on either side. In certain embodiments, the areas can be color coded based on variant. Variants in the same gene can be shown in different hues of the same color. For example, KRAS mutants can be shown in different shades of blue, EGFR mutants in different shades of red.

Turning now to FIG. 10A, the process can comprise receiving genetic information from a DNA sequencer (30). The process can then comprise determining specific gene alterations and quantities thereof (32).

Next, a tumor response map is generated. To generate the map, the process can comprise normalizing the quantities for each gene alteration for rendering across all test points and then generates a scaling factor (34). As used herein, the term "normalize" generally refers to means adjusting values measured on different scales to a notionally common scale. For example, data measured at different points are converted/adjusted so that all values can be resized to a common scale. As used herein, the term "scaling factor" generally refers to a number which scales, or multiplies, some quantity. For example, in the equation y=Cx, C is the scale factor for x. C is also the coefficient of x, and may be called the constant of proportionality of y to x. The values are normalized to allow plotting on a common scale that is visually-friendly. And the scaling factor is used to know the exact heights that correspond to the values to be plotted (e.g. 10% mutant allele frequency may represent 1 cm on the report wherein the total height is 10 cm). The scaling factor is applied to all test points and thus is considered to be a universal scaling factor. For each test point, the process can comprise rendering information on a tumor response map (36). In operation 36, the process can comprise rendering alterations and relative heights using the determined scaling factor (38) and assigns a unique visual indicator for each alteration (40). In addition to the response map, the process can comprise generating a summary of alterations and treatment options (42). Also, information from clinical trials that may help the particular genetic alterations and other helpful treatment suggestions is presented, along with explanations of terminology, test methodology, and other information is added to the report and rendered for the user.

In one implementation, the copy number variation may be reported as graph, indicating various positions in the genome and a corresponding increase or decrease or maintenance of copy number variation at each respective position. Additionally, copy number variation may be used to report a percentage score indicating how much disease material (or nucleic acids having a copy number variation) exists in the cell free polynucleotide sample.

In another embodiment, the report includes annotations to help physicians interpret the results and recommend treatment options. The annotating can include annotating a report for a condition in the NCCN Clinical Practice Guidelines in Oncology™ or the American Society of Clinical Oncology (ASCO) clinical practice guidelines. The annotating can include listing one or more FDA-approved drugs for off-label use, one or more drugs listed in a Centers for Medicare and Medicaid Services (CMS) anti-cancer treatment compendia, and/or one or more experimental drugs found in scientific literature, in the report. The annotating can include connecting a listed drug treatment option to a reference containing scientific information regarding the drug treatment option. The scientific information can be from a peer-reviewed article from a medical journal. The annotating can include providing a link to information on a clinical trial for a drug treatment option in the report. The annotating can include presenting information in a pop-up box or fly-over box near provided drug treatment options in an electronic based report. The annotating can include adding information to a report selected from the group consisting of one or more drug treatment options, scientific information concerning one or more drug treatment options, one or more links to scientific information regarding one or more drug treatment options, one or more links to citations for scientific information regarding one or more drug treatment options, and clinical trial information regarding one or more drug treatment options.

FIG. 10B shows an exemplary process to generate a tumor response map pathway which may be used by a healthcare practitioner, e.g., physician, for example to make patient care decisions. In this embodiment, the process can comprise first determining a global scaling factor (43). In one embodiment, for all non-CNV (copy number variation) reported mutant allele frequencies, the process can comprise transforming the absolute value into a relative metric/scale that may be more amenable for plotting (e.g. Multiply mutant allele frequency by 100 and take log of that value) and determines a global scaling factor using maximum observed value. The process then involves visualizing information from the earliest test dataset (44). Visualizing can comprise graphically representing the information on a user interface (e.g., a computer screen) or in tangible form (e.g., on a piece of paper). For each non-CNV alteration, the process can comprise multiplying the scaling factor by a transformed value for each gene and use as a quantity indicator for plotting that variant, and then assigns a color/unique visual indicator for each alteration. Then the process can comprise visualizing information for subsequent test points (45) using the following pseudo-code:

If unchanged composition of test results, continue prior panel date visual in new panel If alterations remain the same, but quantities have changed Recompute the quantity indicator for plotting that variant and re-plot all updated values in existing panel(s) and new panel for the latest test date.

If new alterations addition

Add the alterations to the top of all existing alterations

Compute transform values

Recompute scaling factor

Re-draw the response map, re-plotting alterations in the prior test date that are still detected in current test date as well as newly emerging alterations If prior existing alteration is not among the set of detected alterations Use a height of zero and plot the quantity of the alteration for all subsequent test dates Still include color is set of unavailable colors Each subsequent panel denoting a test date may also include additional patient or intervention information that may correlate with the alteration changes seen in the remainder of the map. Similar scaling, plotting, and transformation may be also implemented on CNV and other types of DNA alterations (e.g. methylation) to display these quantities in separate or combined charts. These additional annotations may themselves also be quantifiable and similarly plotted on the map.

The process can then comprise determining a summary of alterations and treatment options (46). In one embodiment, for the alteration with the maximum mutant allele frequencies, the following actions are done:

Report all alterations for that gene in decreasing mutant allele frequency order of non-CNV alterations Report all CNV alterations for that gene in decreasing order of CNV value Repeat for next gene with next highest non-CNV mutant allele frequency not yet reported For each reported alteration, the process can comprise including a trend indicator for that alteration over the different test date points.

Grouping of maximum mutant allele frequencies may also extend beyond just the genes they are harbored in to greater encapsulating annotations such as biological pathways, evidence level, etc.

Figure 10D:
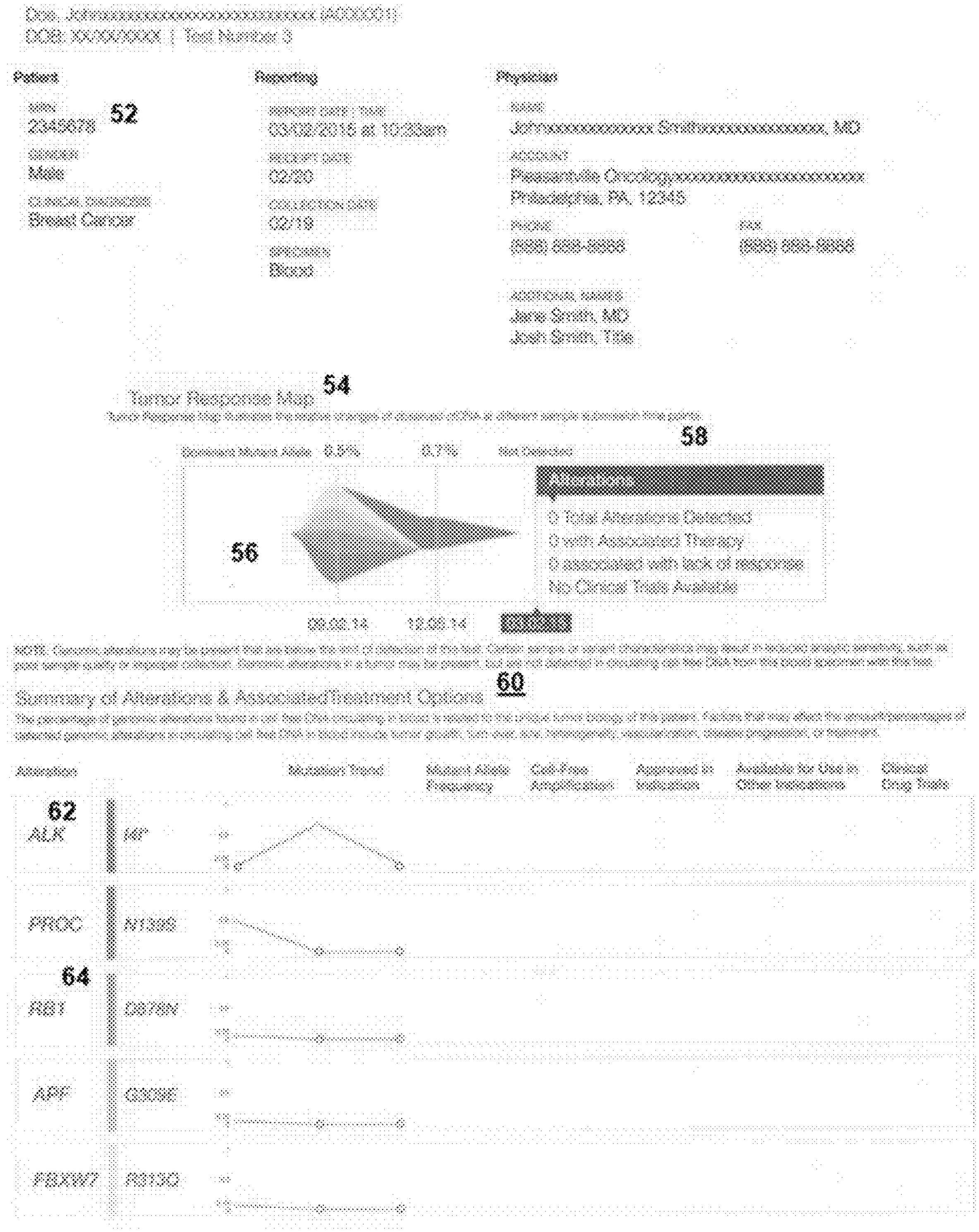
Figures 1, 10D:
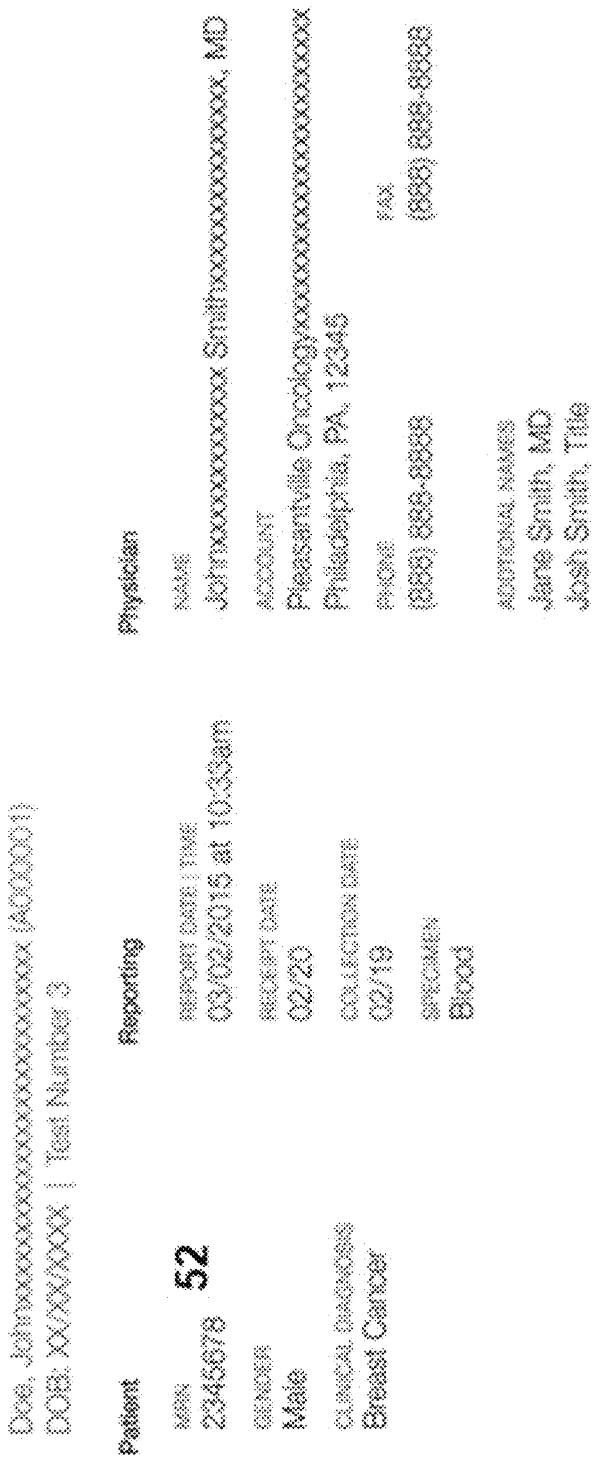
Figures 2, 10D:
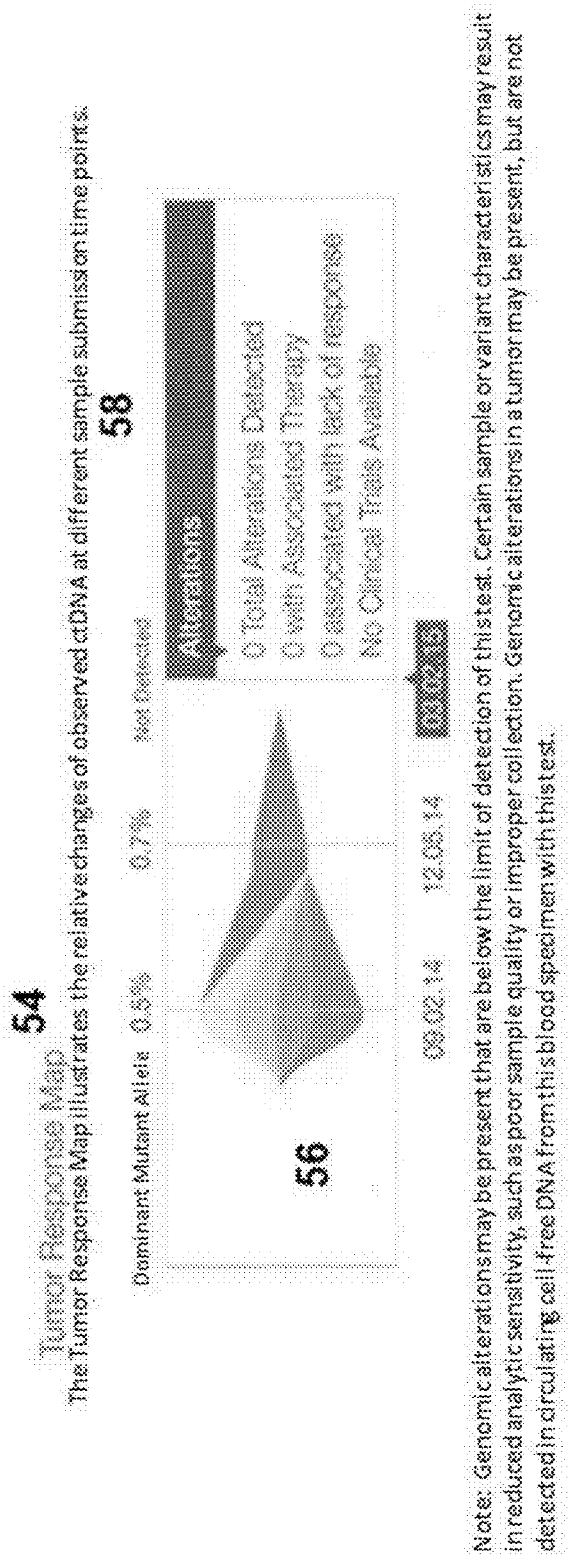
Figures 3, 10D:
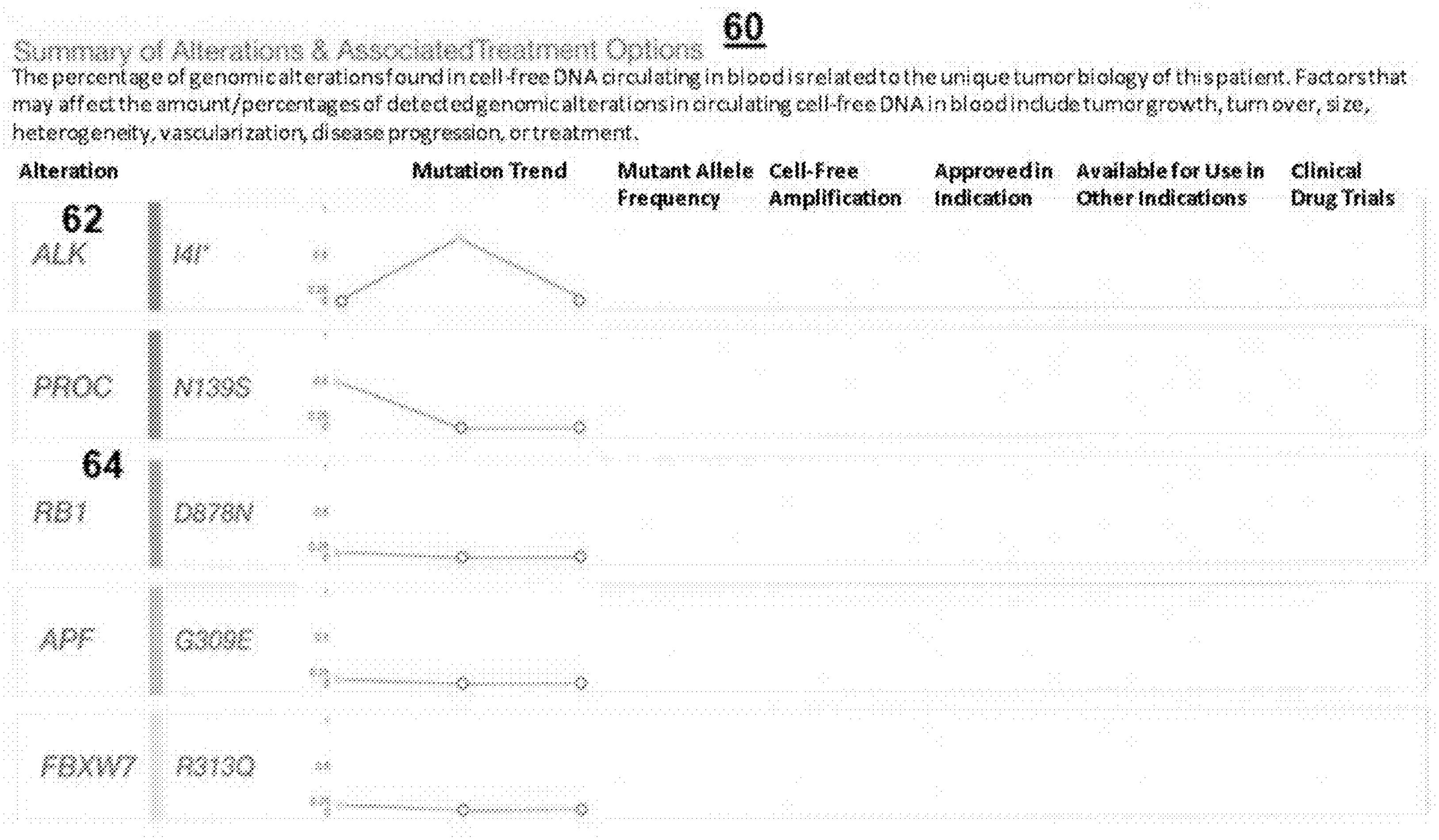

FIGS. 10D-10I show one exemplary report generated by the system of FIG. 9A. In FIG. 10D, a patient identification section 52 provides patient information, reporting date, and physician contact information. A tumor response map 54 includes a modified streamgraph 56 that shows tumor activities with unique colors for each mutant gene. The graph 56 has accompanying summary explanation textbox 58. More details are provided in a summary of alterations and treatment option section 60. The alterations 62 and 64 are presented in section 60, along with mutation trend, mutant allele frequency, cell-free amplification, FDA Approved Drug Indication, FDA Approved Drugs with other Indications, and Clinical Drug Trial information. FIGS. 10D-1, 10D-2, and 10D-3 provide enlarged views of FIG. 10D.

Figure 2:
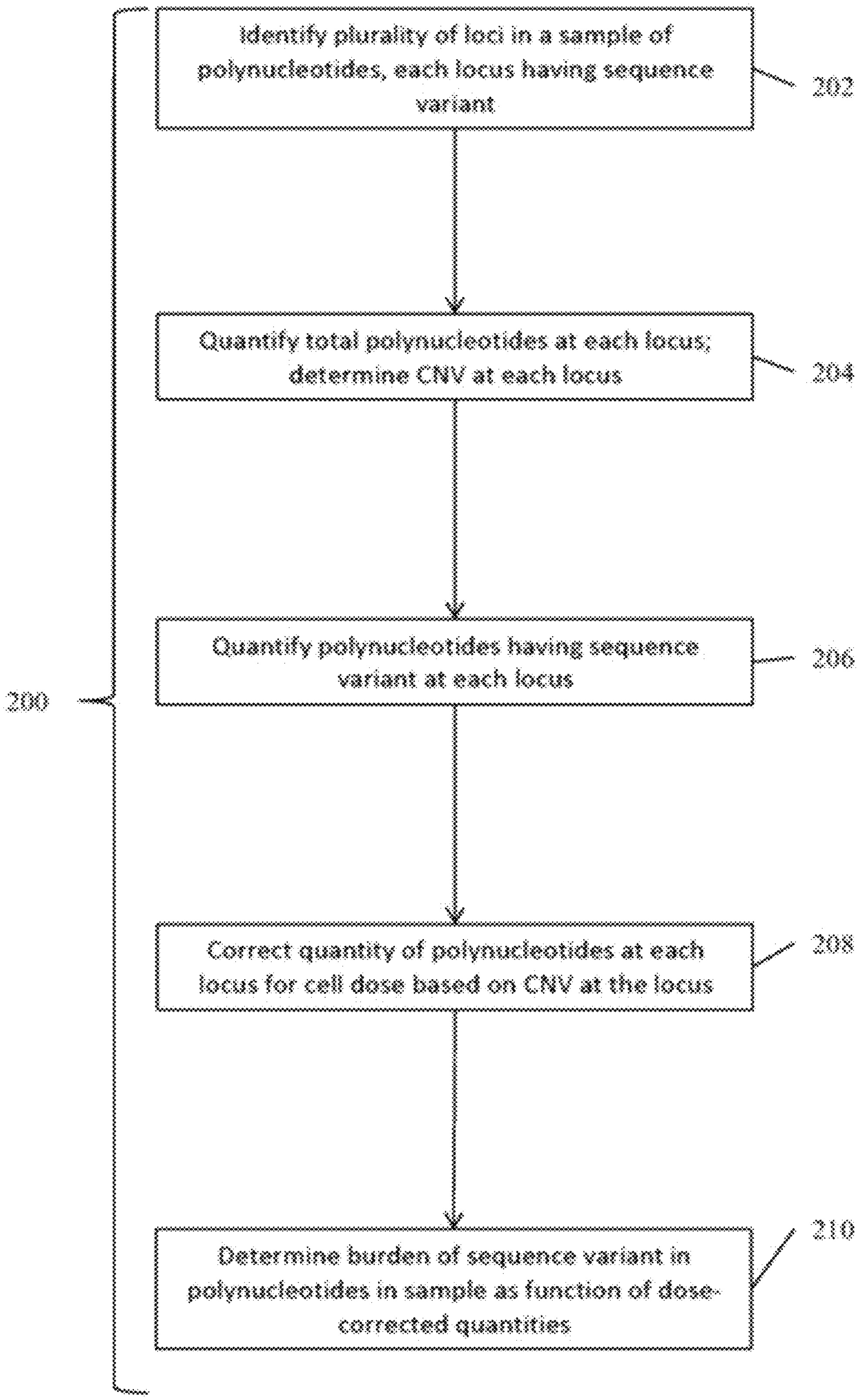
FIG. 2 shows a flow chart of an exemplary method of determining frequency of variants in a sample corrected based on CNV at a locus.
Figure 3:
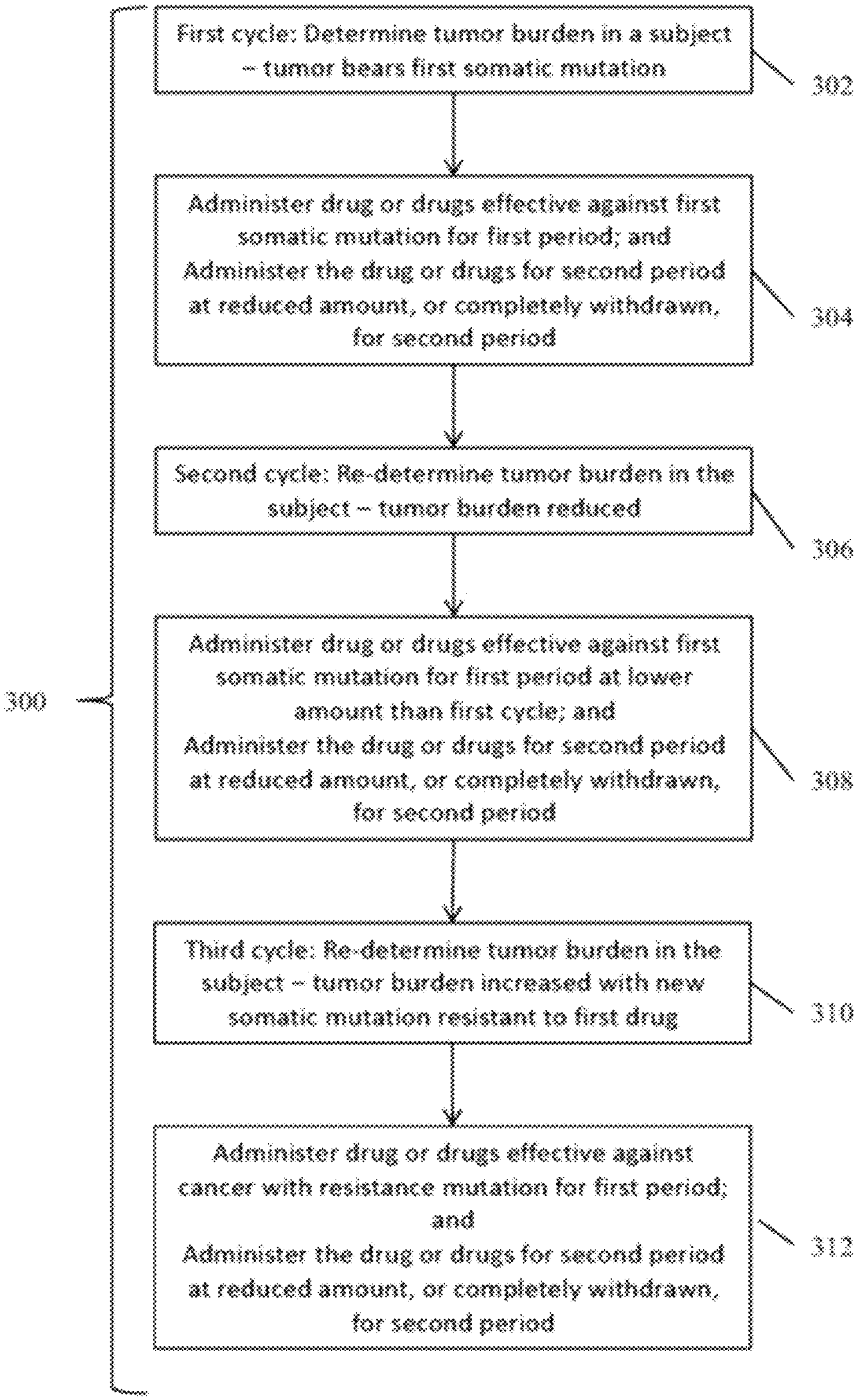
FIG. 3 shows a flow chart of an exemplary method of providing pulsed therapy cycles which can delay drug resistance.
Figure 4:
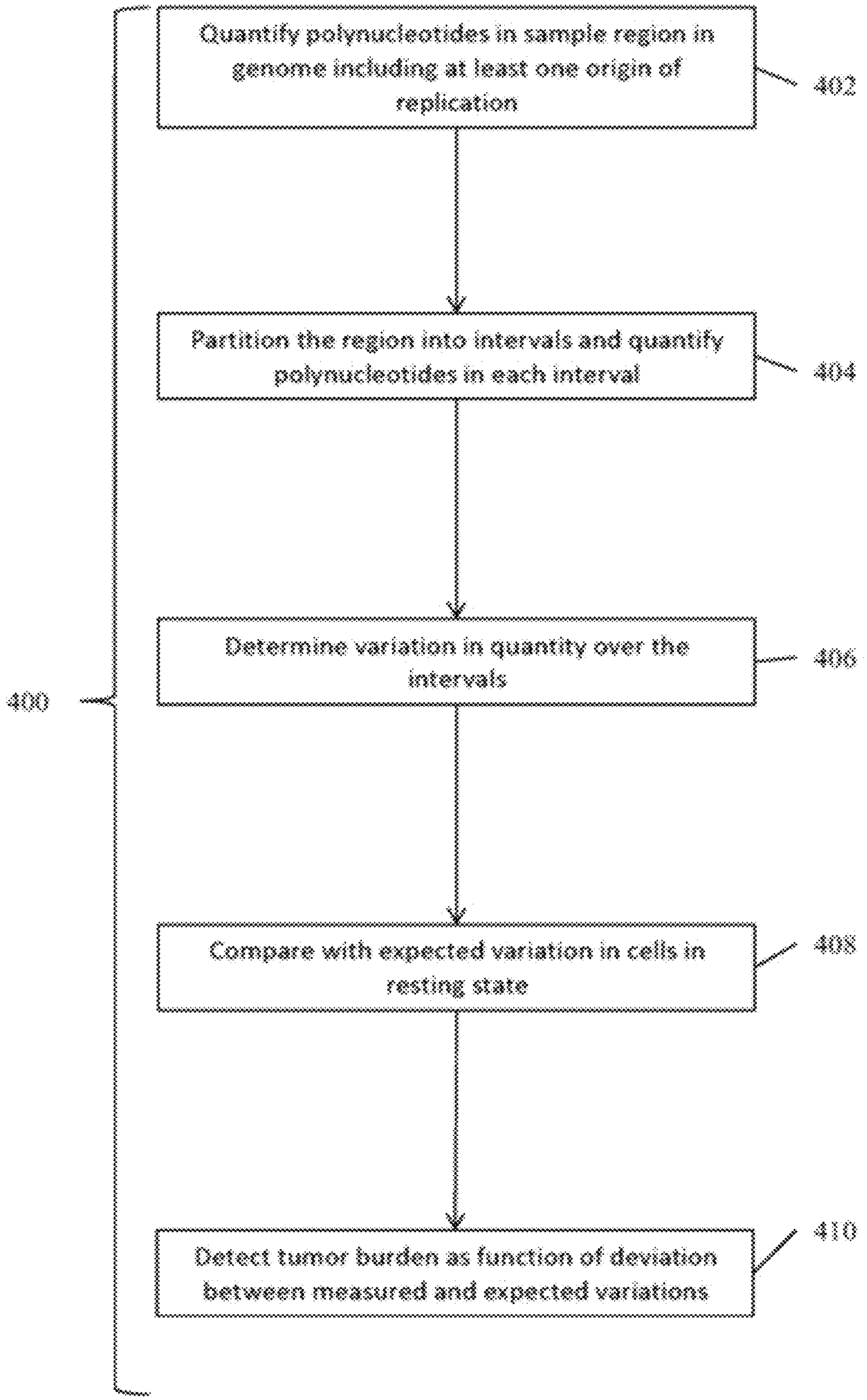
FIG. 4 shows a flow chart of an exemplary method of detecting tumor burden using CNV at origins of replication to detect DNA from dividing cells.

FIG. 10E shows an exemplary report section providing definitions, comments, and interpretation of the tests. FIGS. 10E-1 and 10E-2 provide enlarged views of FIG. 10E. FIG. 10F shows an exemplary detailed therapy result portion of the report. FIGS. 10F-1 and 10F-2 provide enlarged views of FIG. 10F. FIG. 10G shows an exemplary discussion of the clinical relevance of detected alterations. FIGS. 10G-1 and 10G-2 provide enlarged views of FIG. 10G. FIG. 10H shows potentially available medications that are going through clinical trials. FIG. 10I shows the test methods and limitations thereof. FIGS. 10I-1 and 10I-2 provide enlarged views of FIG. 10I.

FIG. 10J-19P shows various exemplary modified streamgraph 56. A streamgraph, or stream graph, is a type of stacked area graph which is displaced around a central axis, resulting in a flowing, organic shape. Streamgraphs are a generalization of stacked area graphs where the baseline is free. By shifting the baseline, it is possible to minimize the change in slope (or "wiggle") in individual series, thereby making it easier to perceive the thickness of any given layer across the data.

Figure 10J:
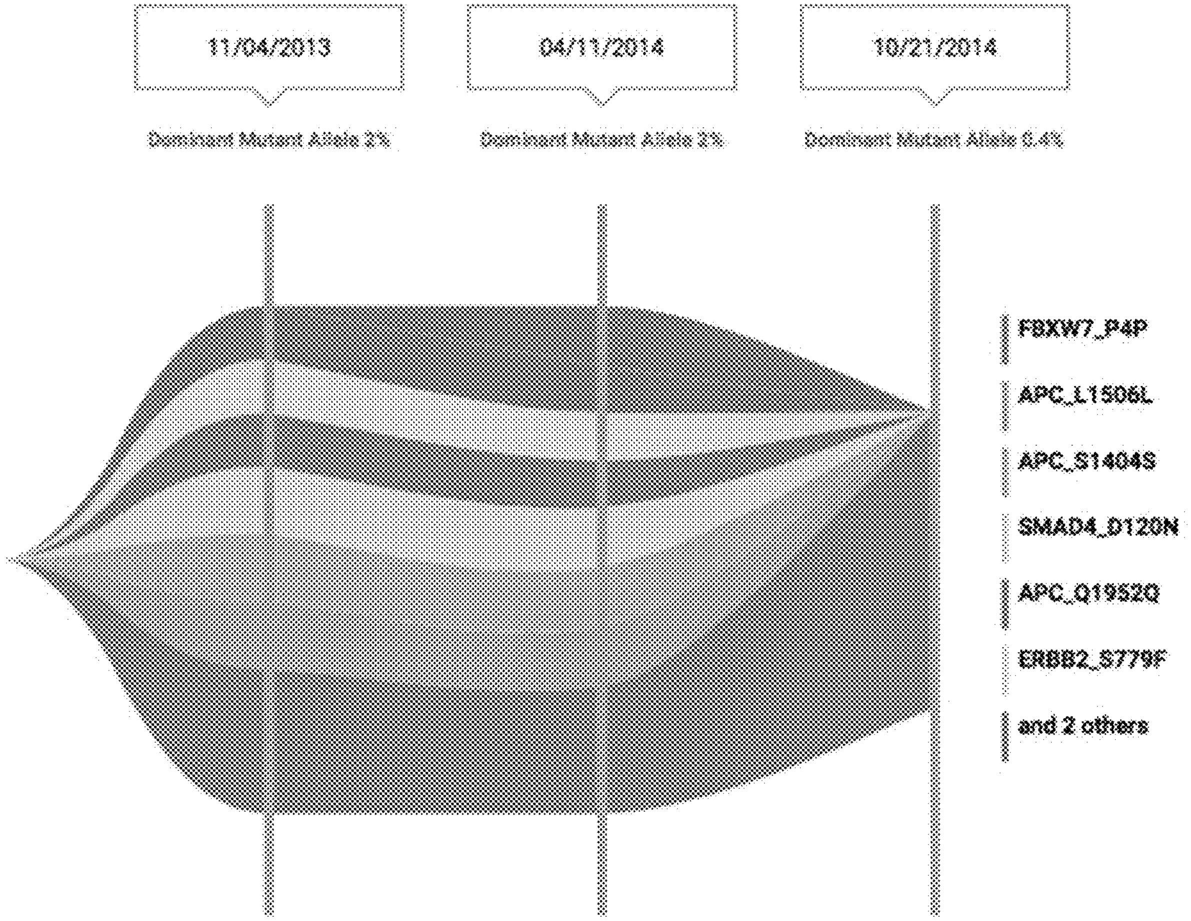
FIG. 10J-10P shows various exemplary modified streamgraph.
Figure 10K:
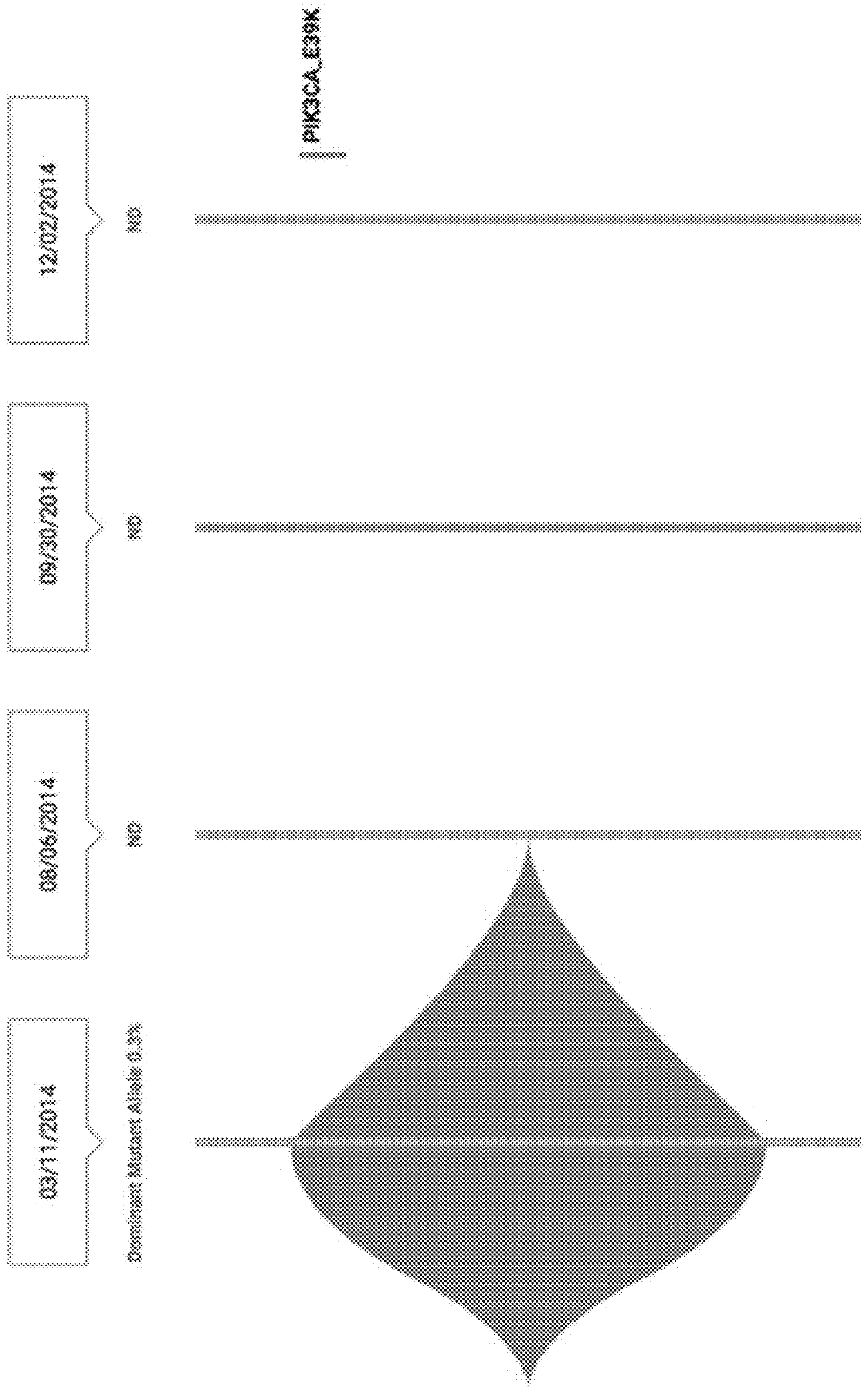
Figure 10L:
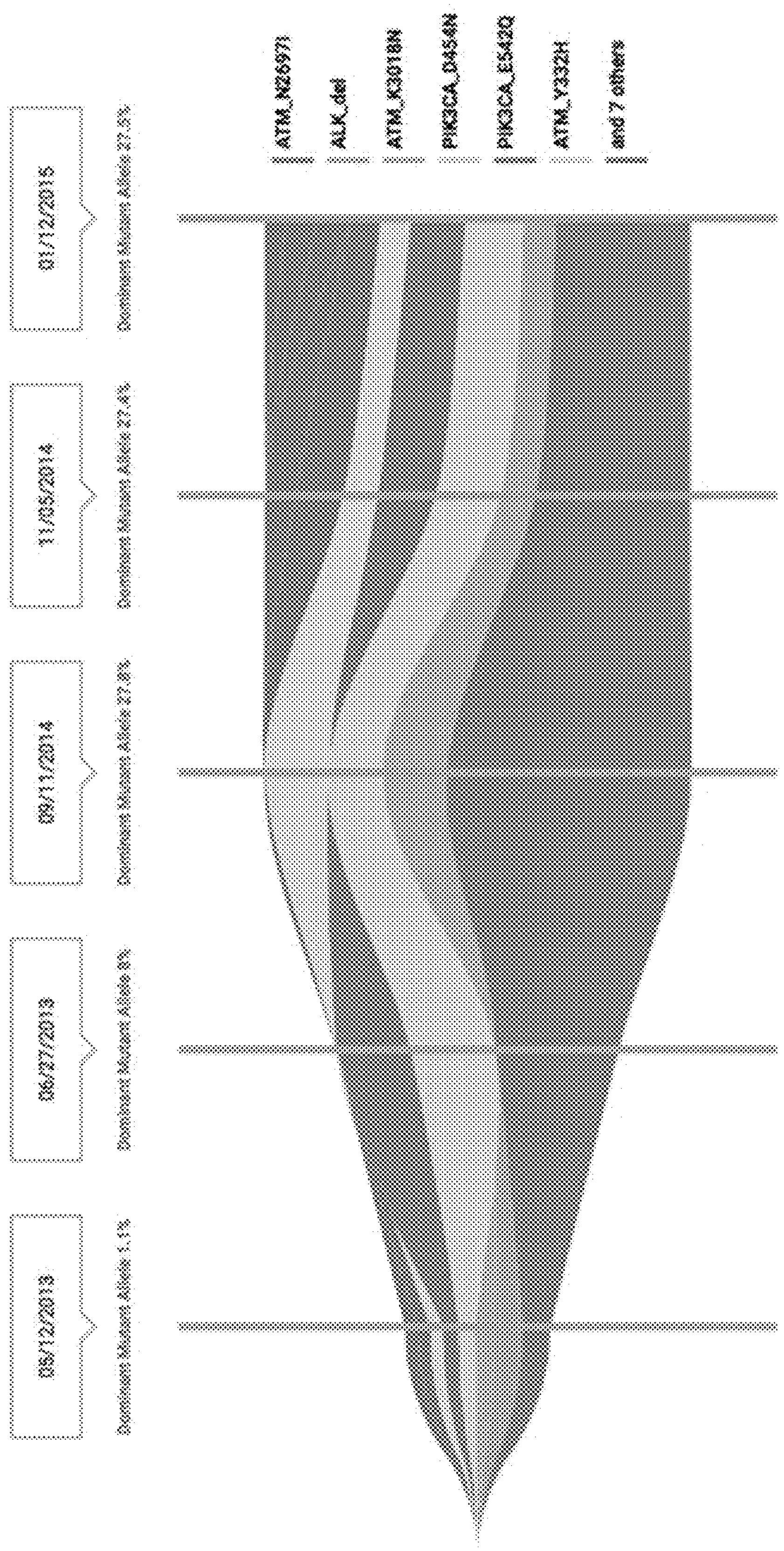
Figure 10M:
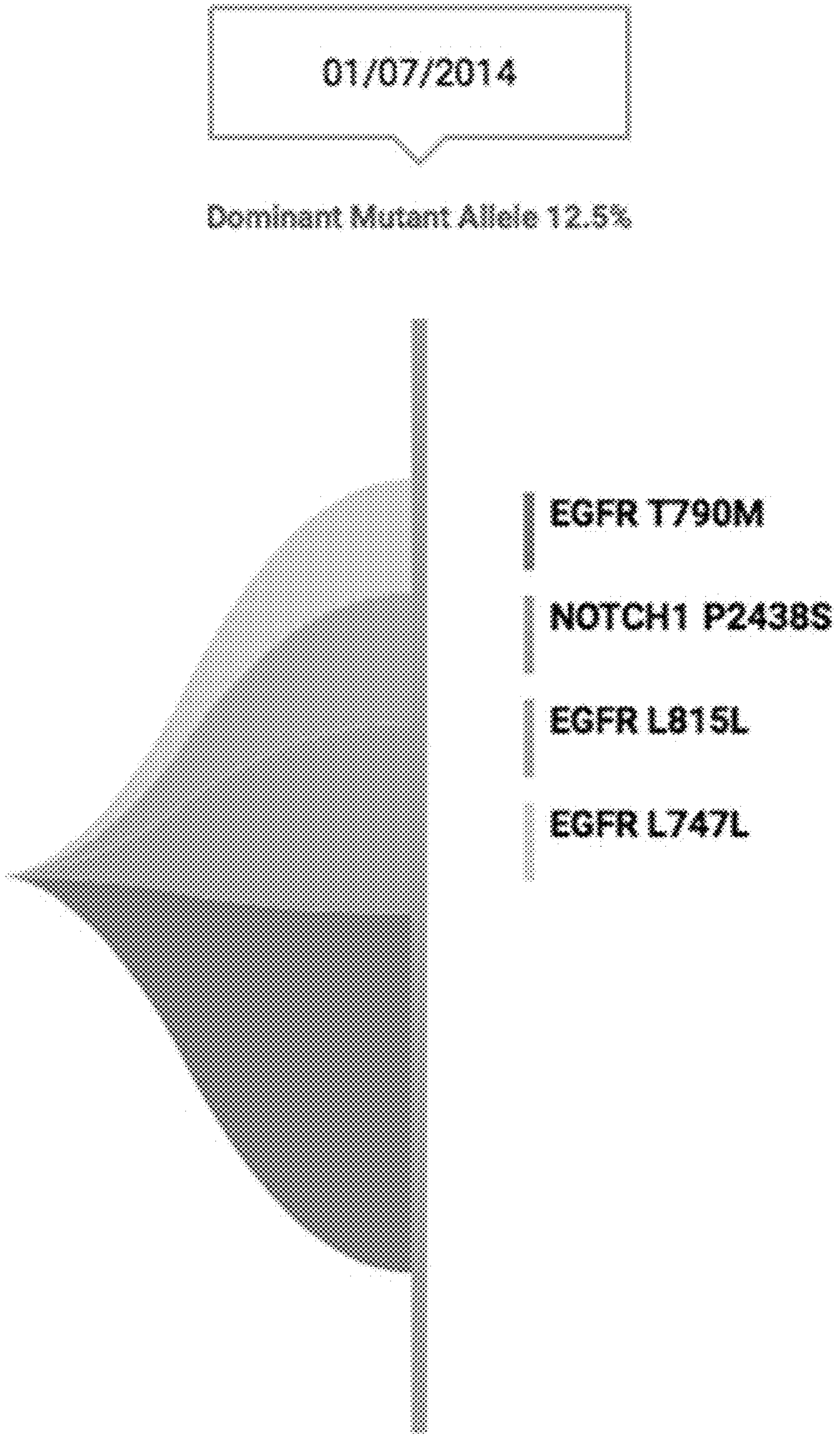
Figure 10N:
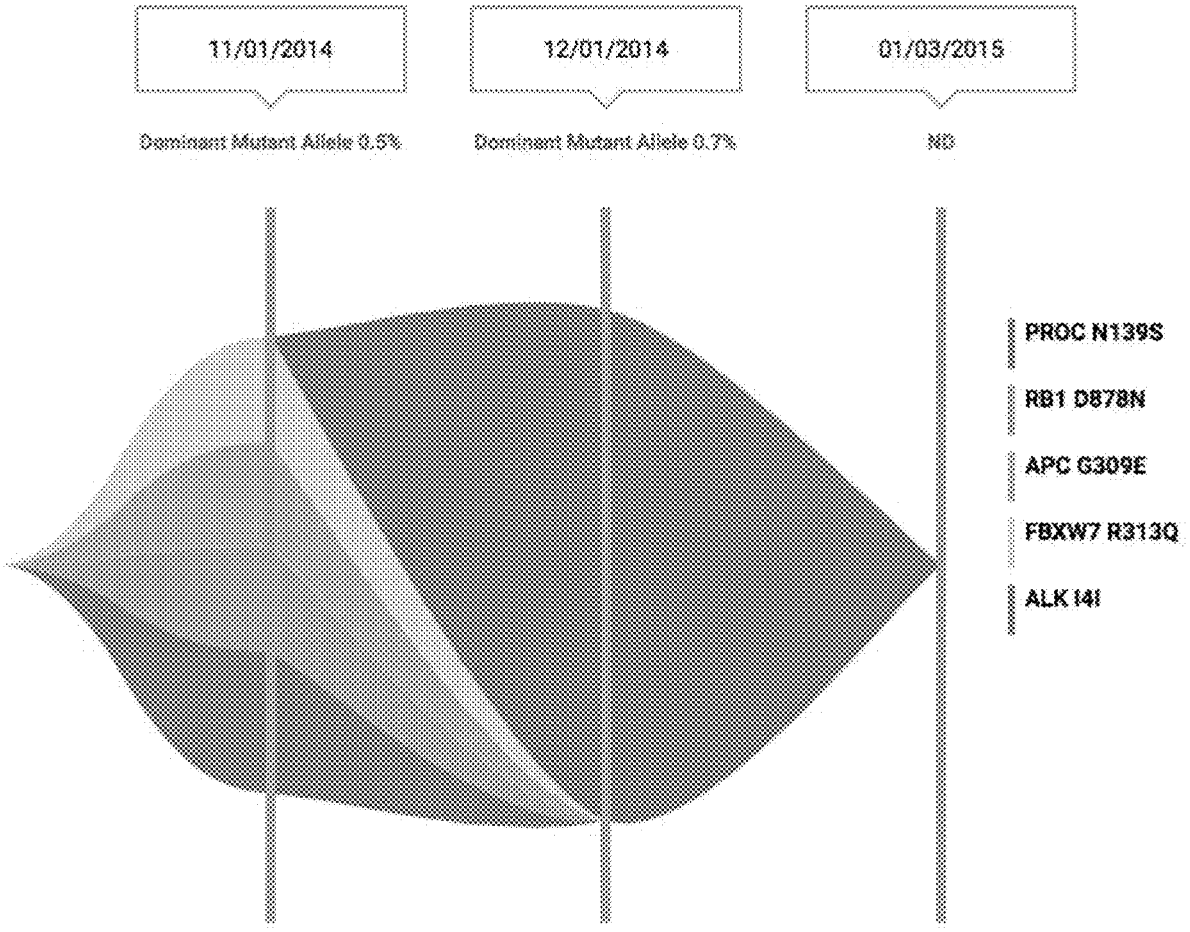
Figure 10O:
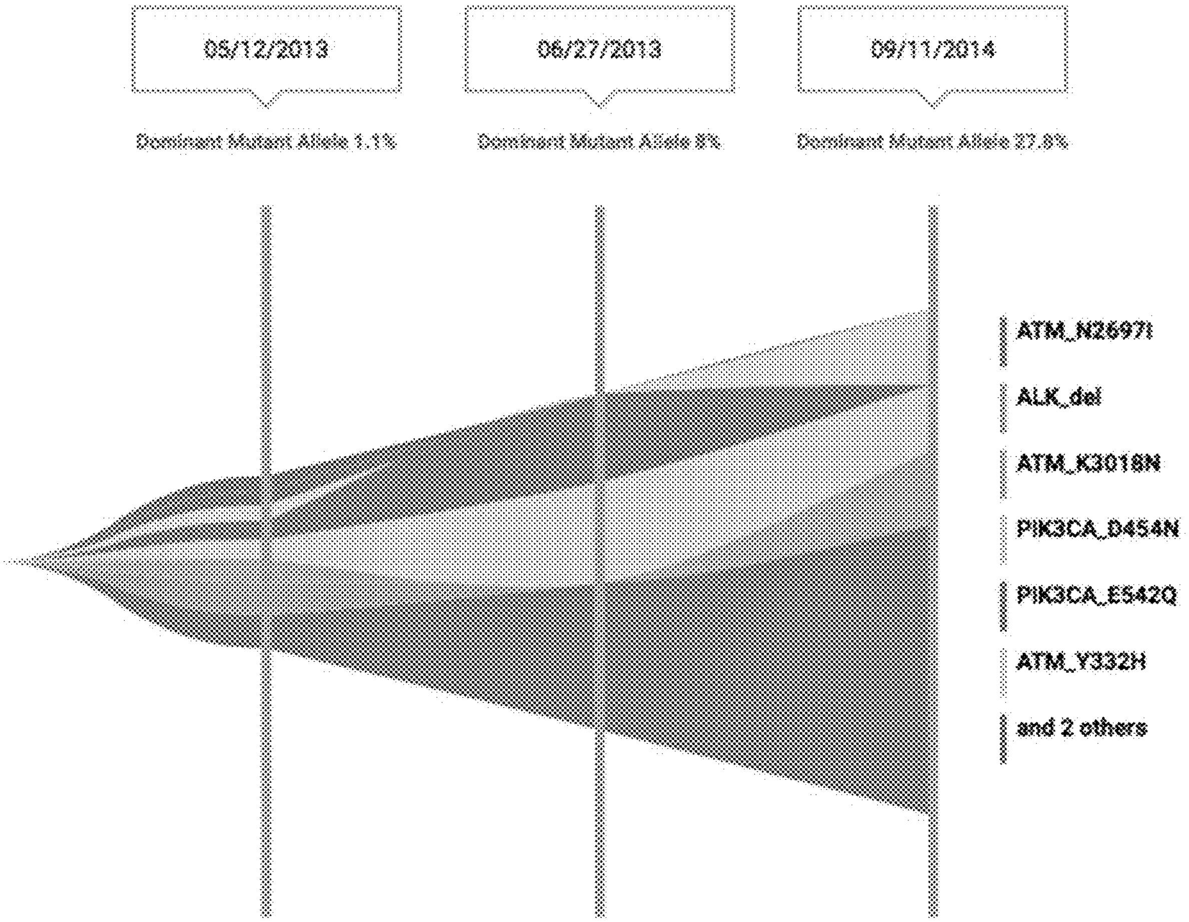
Figure 10P:
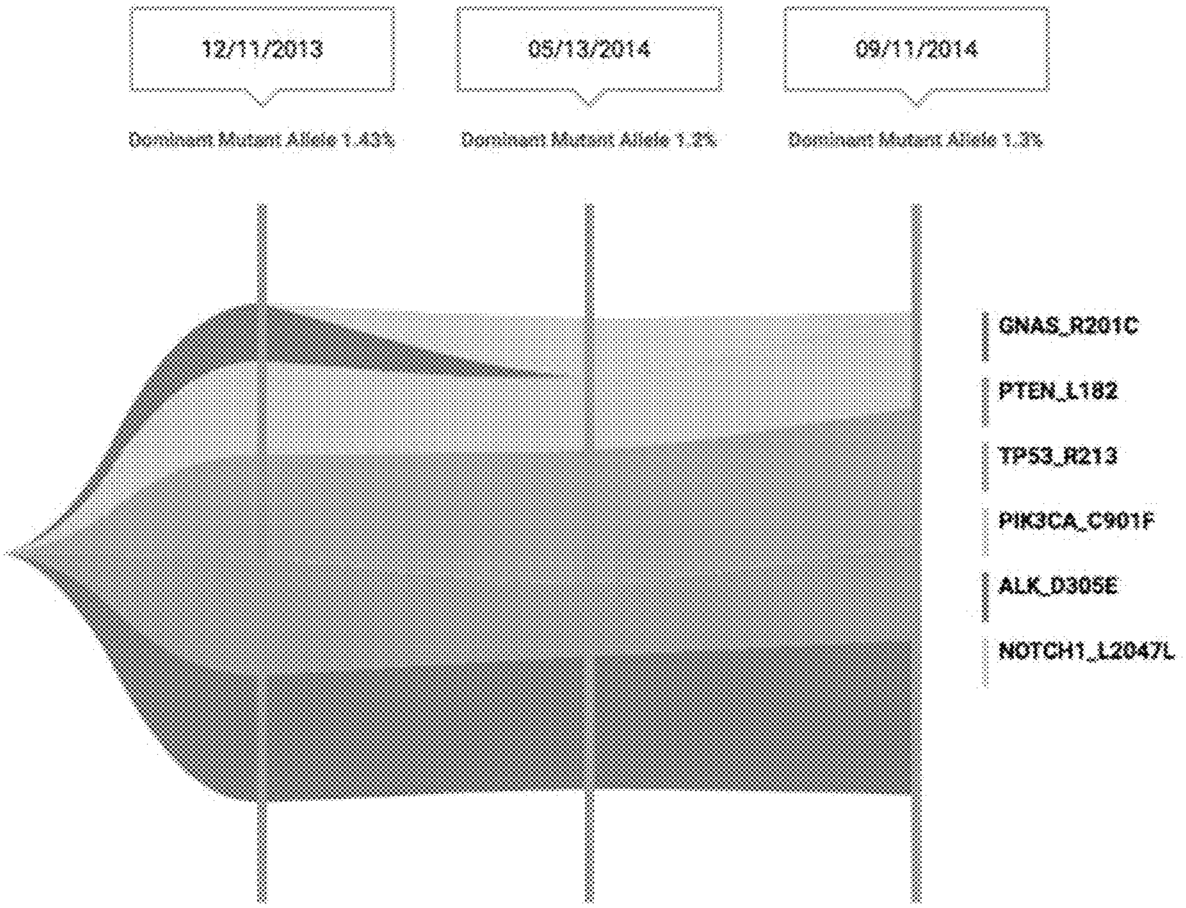

For example, FIG. 10J shows seven layers representing at least 8 mutants over three time periods, and a "0" time point (all values "0"). FIG. 10K shows a single mutant over 4 time periods. No mutants are detected at the second, third and fourth time points. FIG. 10L indicates frequency of dominant allele at each time point. FIG. 10M shows a single time point with a total of four mutants in two genes. Mutants are identified by amino acid at a position changed (i.e., EGFR T790M).

One embodiment renders a streamgraph so that it is not x-axis reflective. The modified graph applies a unique scaling to denote proportional attributes. The graph can indicate the addition of new attributes over time. The presence or absence of a mutation may be reflected in graphical form, indicating various positions in the genome and a corresponding increase or decrease or maintenance of a frequency of mutation at each respective position. Additionally, mutations may be used to report a percentage score indicating how much disease material exists in the cell free polynucleotide sample. A confidence score may accompany each detected mutation, given known statistics of typical variances at reported positions in non-disease reference sequences. Mutations may also be ranked in order of abundance in the subject or ranked by clinically actionable importance.

The mapping of genome positions and copy number variation for the subject with cancer can indicate that a particular cancer is aggressive and resistant to treatment. The subject may be monitored for a period and retested. If at the end of the period, the copy number variation profile, e.g., as depicted in a tumor response map, begins to increase dramatically, this may indicate that the current treatment is not working. A comparison can also done with genetic profiles of other subjects. For example, if it is determined that this increase in copy number variation indicates that the cancer is advancing, then the original treatment regimen as prescribed is no longer treating the cancer and a new treatment is prescribed.

These reports can be submitted and accessed electronically via the internet. Analysis of sequence data may occur at a site other than the location of the subject. The report can be generated and transmitted to the subject's location. Via an internet enabled computer, the subject may access the reports reflecting his tumor burden.

Figure 11A:
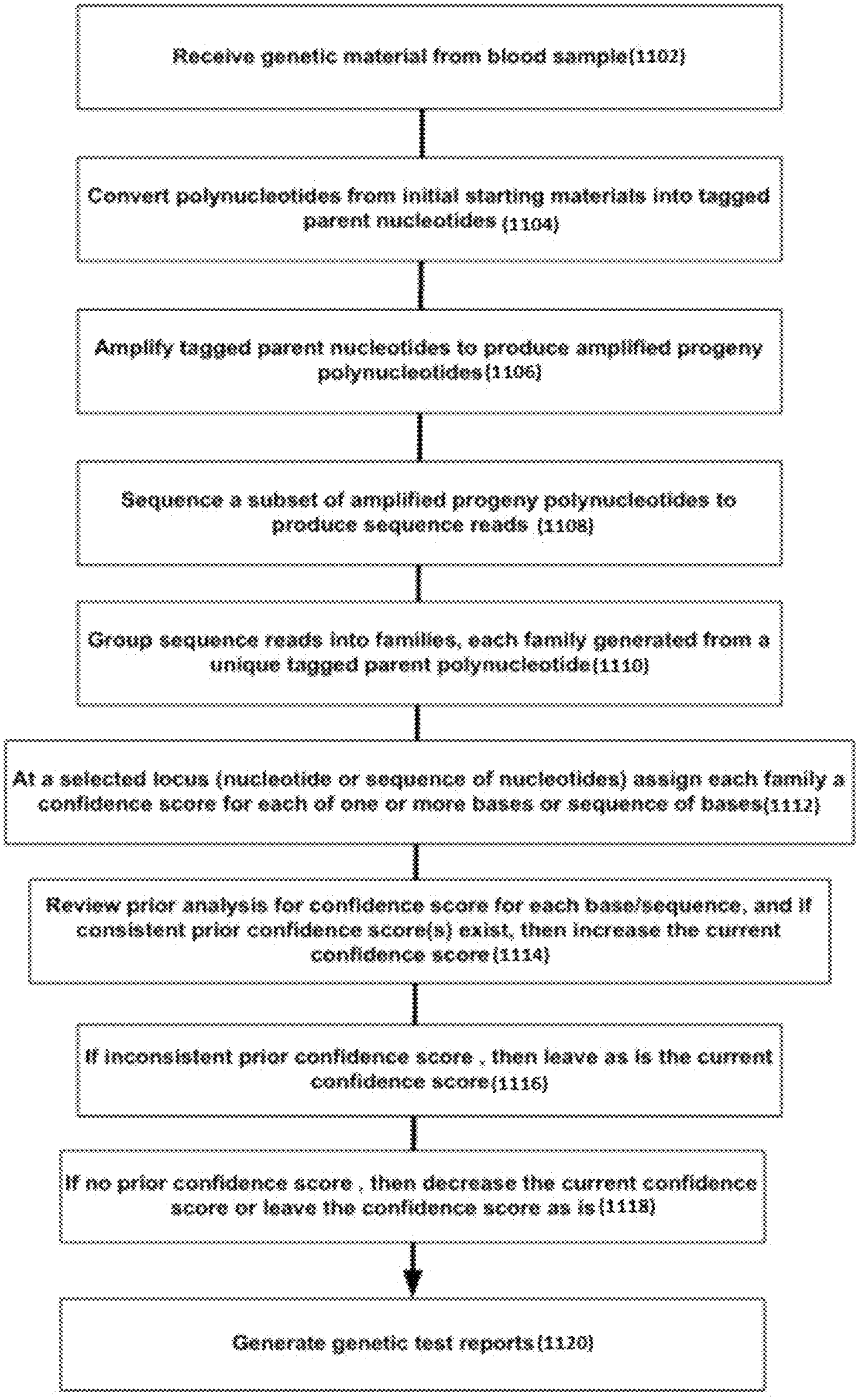
FIG. 11A-11B shows exemplary processes for detecting mutation and reporting test results to users.

Next, details of exemplary gene testing processes are disclosed. Turning now to FIG. 11A, an exemplary process receives genetic materials from blood sample or other body samples (1102). The process can comprise converting the polynucleotides from the genetic materials into tagged parent nucleotides (1104). The tagged parent nucleotides are amplified to produce amplified progeny polynucleotides (1106). A subset of the amplified polynucleotides is sequenced to produce sequence reads (1108), which are grouped into families, each generated from a unique tagged parent nucleotide (1110). At a selected locus, the process can comprise assigning each family a confidence score for each family (1112). Next, a consensus is determined using prior readings. This is done by reviewing prior confidence score for each family, and if consistent prior confidence scores exists, then the current confidence score is increased (1114). If there are prior confidence scores, but they are inconsistent, the current confidence score is not modified in one embodiment (1116). In other embodiments, the confidence score is adjusted in a predetermined manner for inconsistent prior confidence scores. If this is a first time the family is detected, the current confidence score can be reduced as it may be a false reading (1118). The process can comprise inferring the frequency of the family at the locus in the set of tagged parent polynucleotides based on the confidence score. Then genetic test reports are generated as discussed above (1120).

Figure 11B:
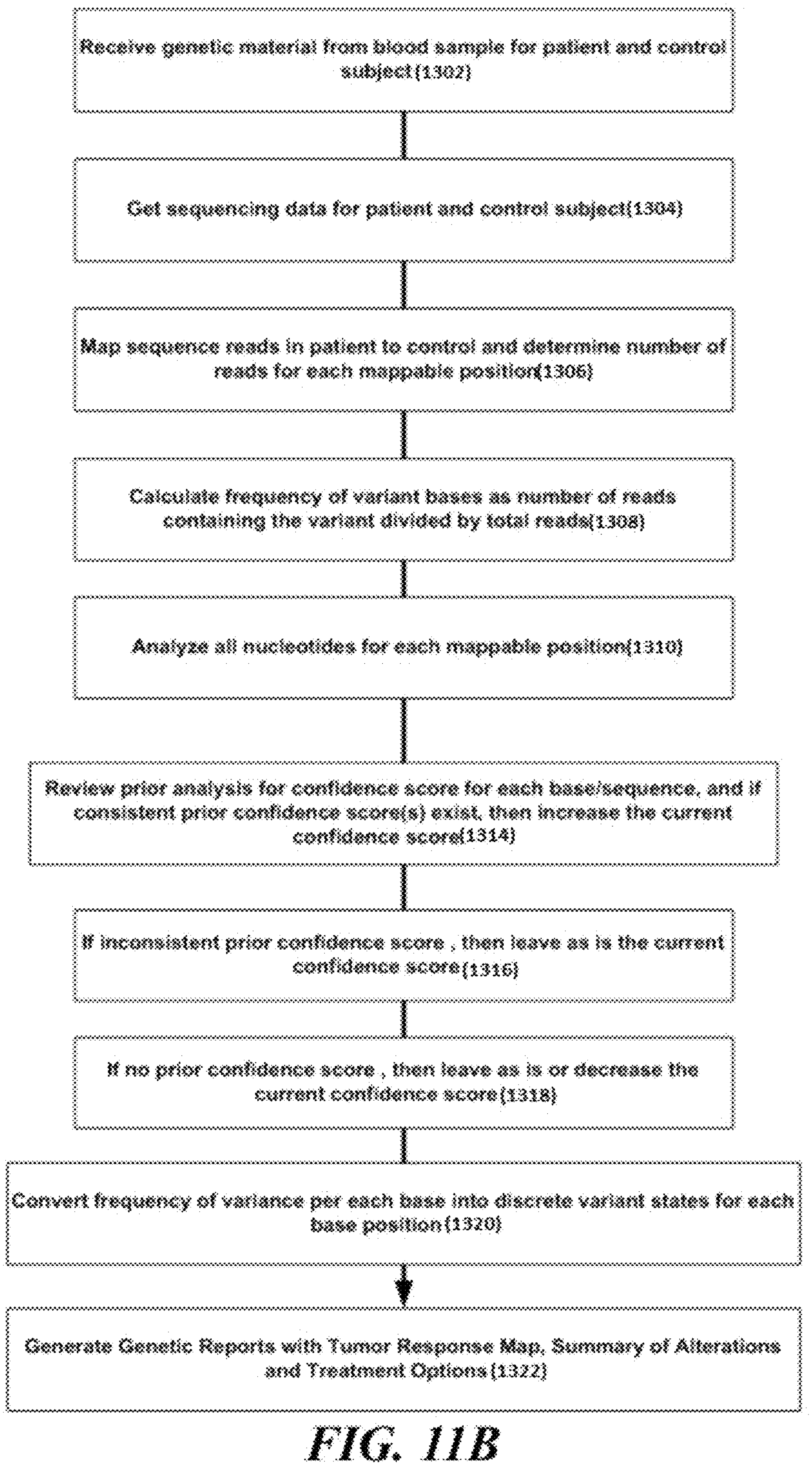

While temporal information has been used in FIGS. 11A-11B to enhance the information for mutation or copy number variation detection, other consensus methods can be applied. In other embodiments, the historical comparison can be used in conjunction with other consensus sequences mapping to a particular reference sequence to detect instances of genetic variation. Consensus sequences mapping to particular reference sequences can be measured and normalized against control samples. Measures of molecules mapping to reference sequences can be compared across a genome to identify areas in the genome in which copy number varies, or heterozygosity is lost. Consensus methods include, for example, linear or non-linear methods of building consensus sequences (e.g., voting, averaging, statistical, maximum a posteriori or maximum likelihood detection, dynamic programming, Bayesian, hidden Markov or support vector machine methods, etc.) derived from digital communication theory, information theory, or bioinformatics. After the sequence read coverage has been determined, a stochastic modeling algorithm is applied to convert the normalized nucleic acid sequence read coverage for each window region to the discrete copy number states. In some cases, this algorithm may comprise one or more of the following: Hidden Markov Model, dynamic programming, support vector machine, Bayesian network, trellis decoding, Viterbi decoding, expectation maximization, Kalman filtering methodologies and neural networks.

As depicted in FIG. 11B, a comparison of sequence coverage to a control sample or reference sequence may aid in normalization across windows. In this embodiment, cell free DNAs are extracted and isolated from a readily accessible bodily fluid such as blood, sweat, saliva, urine, etc. For example, cell free DNAs can be extracted using a variety of methods known in the art, including but not limited to isopropanol precipitation and/or silica based purification. Cell free DNAs may be extracted from any number of subjects, such as subjects without cancer, subjects at risk for cancer, or subjects known to have cancer (e.g. through other means).

Following the isolation/extraction step, any of a number of different sequencing operations may be performed on the cell free polynucleotide sample. Samples may be processed before sequencing with one or more reagents (e.g., enzymes, unique identifiers (e.g., barcodes), probes, etc.). In some cases if the sample is processed with a unique identifier such as a barcode, the samples or fragments of samples may be tagged individually or in subgroups with the unique identifier. The tagged sample may then be used in a downstream application such as a sequencing reaction and individual molecules may be tracked to parent molecules.

The cell free polynucleotides can be tagged or tracked in order to permit subsequent identification and origin of the particular polynucleotide. The assignment of an identifier to individual or subgroups of polynucleotides may allow for a unique identity to be assigned to individual sequences or fragments of sequences. This may allow acquisition of data from individual samples and is not limited to averages of samples. In some examples, nucleic acids or other molecules derived from a single strand may share a common tag or identifier and therefore may be later identified as being derived from that strand. Similarly, all of the fragments from a single strand of nucleic acid may be tagged with the same identifier or tag, thereby permitting subsequent identification of fragments from the parent strand. In other cases, gene expression products (e.g., mRNA) may be tagged in order to quantify expression. A barcode or barcode in combination with sequence to which it is attached can be counted. In still other cases, the systems and methods can be used as a PCR amplification control. In such cases, multiple amplification products from a PCR reaction can be tagged with the same tag or identifier. If the products are later sequenced and demonstrate sequence differences, differences among products with the same identifier can then be attributed to PCR error. Additionally, individual sequences may be identified based upon characteristics of sequence data for the read themselves. For example, the detection of unique sequence data at the beginning (start) and end (stop) portions of individual sequencing reads may be used, alone or in combination, with the length, or number of base pairs of each sequence read to assign unique identities to individual molecules. Fragments from a single strand of nucleic acid, having been assigned a unique identity, may thereby permit subsequent identification of fragments from the parent strand. This can be used in conjunction with bottlenecking the initial starting genetic material to limit diversity.

Further, using unique sequence data at the beginning (start) and end (stop) portions of individual sequencing reads and sequencing read length may be used, alone or combination, with the use of barcodes. In some cases, the barcodes may be unique as described herein. In other cases, the barcodes themselves may not be unique. In this case, the use of non-unique barcodes, in combination with sequence data at the beginning (start) and end (stop) portions of individual sequencing reads and sequencing read length may allow for the assignment of a unique identity to individual sequences. Similarly, fragments from a single strand of nucleic acid having been assigned a unique identity may thereby permit subsequent identification of fragments from the parent strand.

Generally, the methods and systems provided herein are useful for preparation of cell free polynucleotide sequences to a down-stream application sequencing reaction. Often, a sequencing method is classic Sanger sequencing. Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxim-Gilbert sequencing, primer walking, and any other sequencing methods known in the art.

Sequencing methods typically involve sample preparation, sequencing of polynucleotides in the prepared sample to produce sequence reads and bioinformatic manipulation of the sequence reads to produce quantitative and/or qualitative genetic information about the sample. Sample preparation typically involves converting polynucleotides in a sample into a form compatible with the sequencing platform used. This conversion can involve tagging polynucleotides. In certain embodiments of this invention the tags comprise polynucleotide sequence tags. Conversion methodologies used in sequencing may not be 100% efficient. For example, it is not uncommon to convert polynucleotides in a sample with a conversion efficiency of about 1-5%, that is, about 1-5% of the polynucleotides in a sample are converted into tagged polynucleotides. Polynucleotides that are not converted into tagged molecules are not represented in a tagged library for sequencing. Accordingly, polynucleotides having genetic variants represented at low frequency in the initial genetic material may not be represented in the tagged library and, therefore may not be sequenced or detected. By increasing conversion efficiency, the probability that a polynucleotide in the initial genetic material will be represented in the tagged library and, consequently, detected by sequencing is increased. Furthermore, rather than directly address the low conversion efficiency issue of library preparation, most protocols to date call for greater than 1 microgram of DNA as input material. However, when input sample material is limited or detection of polynucleotides with low representation is desired, high conversion efficiency can efficiently sequence the sample and/or to adequately detect such polynucleotides.

Generally, mutation detection may be performed on selectively enriched regions of the genome or transcriptome purified and isolated (1302). As described herein, specific regions, which may include but are not limited to genes, oncogenes, tumor suppressor genes, promoters, regulatory sequence elements, non-coding regions, miRNAs, snRNAs and the like may be selectively amplified from a total population of cell free polynucleotides. This may be performed as herein described. In one example, multiplex sequencing may be used, with or without barcode labels for individual polynucleotide sequences. In other examples, sequencing may be performed using any nucleic acid sequencing platforms known in the art. This step generates a plurality of genomic fragment sequence reads (1304). Additionally, a reference sequence is obtained from a control sample, taken from another subject. In some cases, the control subject may be a subject known to not have known genetic aberrations or disease. In some cases, these sequence reads may contain barcode information. In other examples, barcodes are not utilized.

After sequencing, reads can be assigned a quality score. A quality score may be a representation of reads that indicates whether those reads may be useful in subsequent analysis based on a threshold. In some cases, some reads are not of sufficient quality or length to perform the subsequent mapping step. Sequencing reads with a quality score at least 90%, 95%, 99%, 99.9%, 99.99% or 99.999% may be filtered out of the data set. In other cases, sequencing reads assigned a quality scored at least 90%, 95%, 99%, 99.9%, 99.99% or 99.999% may be filtered out of the data set. In step 1306, the genomic fragment reads that meet a specified quality score threshold are mapped to a reference genome, or a reference sequence that is known not to contain mutations. After mapping alignment, sequence reads are assigned a mapping score. A mapping score may be a representation or reads mapped back to the reference sequence indicating whether each position is or is not uniquely mappable. In some instances, reads may be sequences unrelated to mutation analysis. For example, some sequence reads may originate from contaminant polynucleotides. Sequencing reads with a mapping score at least 90%, 95%, 99%, 99.9%, 99.99% or 99.999% may be filtered out of the data set. In other cases, sequencing reads assigned a mapping scored less than 90%, 95%, 99%, 99.9%, 99.99% or 99.999% may be filtered out of the data set.

For each mappable base, bases that do not meet the minimum threshold for mappability, or low quality bases, may be replaced by the corresponding bases as found in the reference sequence.

The frequency of variant bases may be calculated as the number of reads containing the variant divided by the total number of reads 1308 after ascertaining read coverage and identifying variant bases relative to the control sequence in each read. This may be expressed as a ratio for each mappable position in the genome.

For each base position, the frequencies of all four nucleotides, cytosine, guanine, thymine, adenine can be analyzed in comparison to the reference sequence. A stochastic or statistical modeling algorithm can be applied to convert the normalized ratios for each mappable position to reflect frequency states for each base variant. In some cases, this algorithm may comprise one or more of the following: Hidden Markov Model, dynamic programming, support vector machine, Bayesian or probabilistic modeling, trellis decoding, Viterbi decoding, expectation maximization, Kalman filtering methodologies, and neural networks.

The discrete mutation states of each base position can be utilized to identify a base variant with high frequency of variance as compared to the baseline of the reference sequence. In some cases, the baseline might represent a frequency of at least 0.0001%, 0.001%, 0.01%, 0.1%, 1.0%, 2.0%, 3.0%, 4.0% 5.0%, 10%, or 25%. In other cases the baseline might represent a frequency of at least 0.0001%, 0.001%, 0.01%, 0.1%, 1.0%, 2.0%, 3.0%, 4.0% 5.0%, 10%, or 25%. In some cases, all adjacent base positions with the base variant or mutation can be merged into a segment to report the presence or absence of a mutation. In some cases, various positions can be filtered before they are merged with other segments.

After calculation of frequencies of variance for each base position, the variant with largest deviation for a specific position in the sequence derived from the subject as compared to the reference sequence can be identified as a mutation. In some cases, a mutation may be a cancer mutation. In other cases, a mutation might be correlated with a disease state.

A mutation or variant may comprise a genetic aberration that includes, but is not limited to a single base substitution, or small indels, transversions, translocations, inversion, deletions, truncations or gene truncations. In some cases, a mutation may be at most 1, 2, 3, 4, 5, 6, 7, 8, 9, 10, 15 or 20 nucleotides in length. On other cases a mutation may be at least 1, 2, 3, 4, 5, 6, 7, 8, 9, 10, 15 or 20 nucleotides in length.

Next, a consensus is determined using prior readings. This is done by reviewing prior confidence score for the corresponding bases, and if consistent prior confidence scores exists, then the current confidence score is increased (1314). If there are prior confidence scores, but they are inconsistent, the current confidence score is not modified in one embodiment (1316). In other embodiments, the confidence score is adjusted in a predetermined manner for inconsistent prior confidence scores. If this is a first time the family is detected, the current confidence score can be reduced as it may be a false reading (1318). The process can comprise then converting the frequency of variance per each base into discrete variant states for each base position (1320).

Numerous cancers may be detected using the methods and systems described herein. Cancers cells, as most cells, can be characterized by a rate of turnover, in which old cells die and are replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic aberrations such as copy number variation as well as mutations. This phenomenon may be used to detect the presence or absence of cancers individuals using the methods and systems described herein.

For example, blood from subjects at risk for cancer may be drawn and prepared as described herein to generate a population of cell free polynucleotides. In one example, this might be cell free DNA. The systems and methods of the disclosure may be employed to detect mutations or copy number variations that may exist in certain cancers present. The method may help detect the presence of cancerous cells in the body, despite the absence of symptoms or other hallmarks of disease.

The types and number of cancers that may be detected may include but are not limited to blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like.

The system and methods may be used to detect any number of genetic aberrations that may cause or result from cancers. These may include but are not limited to mutations, mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer.

Additionally, the systems and methods described herein may also be used to help characterize certain cancers. Genetic data produced from the system and methods of this disclosure may allow practitioners to help better characterize a specific form of cancer. Often times, cancers are heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer.

The systems and methods provided herein may be used to monitor already known cancers, or other diseases in a particular subject. This may allow either a subject or practitioner to adapt treatment options in accord with the progress of the disease. In this example, the systems and methods described herein may be used to construct genetic profiles of a particular subject of the course of the disease. In some instances, cancers can progress, becoming more aggressive and genetically unstable. In other examples, cancers may remain benign, inactive or dormant. The system and methods of this disclosure may be useful in determining disease progression.

Further, the systems and methods described herein may be useful in determining the efficacy of a particular treatment option. In one example, successful treatment options may actually increase the amount of copy number variation or mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy. Additionally, if a cancer is observed to be in remission after treatment, the systems and methods described herein may be useful in monitoring residual disease or recurrence of disease.

The methods and systems described herein may not be limited to detection of mutations and copy number variations associated with only cancers. Various other diseases and infections may result in other types of conditions that may be suitable for early detection and monitoring. For example, in certain cases, genetic disorders or infectious diseases may cause a certain genetic mosaicism within a subject. This genetic mosaicism may cause copy number variation and mutations that could be observed. In another example, the system and methods of the disclosure may also be used to monitor the genomes of immune cells within the body. Immune cells, such as B cells, may undergo rapid clonal expansion upon the presence certain diseases. Clonal expansions may be monitored using copy number variation detection and certain immune states may be monitored. In this example, copy number variation analysis may be performed over time to produce a profile of how a particular disease may be progressing.

Further, the systems and methods of this disclosure may also be used to monitor systemic infections themselves, as may be caused by a pathogen such as a bacteria or virus. Copy number variation or even mutation detection may be used to determine how a population of pathogens are changing during the course of infection. This may be particularly important during chronic infections, such as HIV/AIDs or Hepatitis infections, whereby viruses may change life cycle state and/or mutate into more virulent forms during the course of infection.

Yet another example that the system and methods of this disclosure may be used for is the monitoring of transplant subjects. Generally, transplanted tissue undergoes a certain degree of rejection by the body upon transplantation. The methods of this disclosure may be used to determine or profile rejection activities of the host body, as immune cells attempt to destroy transplanted tissue. This may be useful in monitoring the status of transplanted tissue as well as altering the course of treatment or prevention of rejection.

Further, the methods of the disclosure may be used to characterize the heterogeneity of an abnormal condition in a subject, the method comprising generating a genetic profile of extracellular polynucleotides in the subject, wherein the genetic profile comprises a plurality of data resulting from copy number variation and mutation analyses. In some cases, including but not limited to cancer, a disease may be heterogeneous. Disease cells may not be identical. In the example of cancer, some tumors are known to comprise different types of tumor cells, some cells in different stages of the cancer. In other examples, heterogeneity may comprise multiple foci of disease. Again, in the example of cancer, there may be multiple tumor foci, perhaps where one or more foci are the result of metastases that have spread from a primary site.

The methods of this disclosure may be used to generate or profile, fingerprint or set of data that is a summation of genetic information derived from different cells in a heterogeneous disease. This set of data may comprise copy number variation and mutation analyses alone or in combination.

Additionally, the systems and methods of the disclosure may be used to diagnose, prognose, monitor or observe cancers or other diseases of fetal origin. That is, these methodologies may be employed in a pregnant subject to diagnose, prognose, monitor or observe cancers or other diseases in a unborn subject whose DNA and other polynucleotides may co-circulate with maternal molecules.

Further, these reports are submitted and accessed electronically via the internet. Analysis of sequence data occurs at a site other than the location of the subject. The report is generated and transmitted to the subject's location. Via an internet enabled computer, the subject accesses the reports reflecting his tumor burden.

The annotated information can be used by a health care provider to select other drug treatment options and/or provide information about drug treatment options to an insurance company. The method can include annotating the drug treatment options for a condition in, for example, the NCCN Clinical Practice Guidelines in Oncology™ or the American Society of Clinical Oncology (ASCO) clinical practice guidelines.

The drug treatment options that are stratified in a report can be annotated in the report by listing additional drug treatment options. An additional drug treatment can be an FDA-approved drug for an off-label use. A provision in the 1993 Omnibus Budget Reconciliation Act (OBRA) requires Medicare to cover off-label uses of anticancer drugs that are included in standard medical compendia. The drugs used for annotating lists can be found in CMS approved compendia, including the National Comprehensive Cancer Network (NCCN) Drugs and Biologics Compendium™, Thomson Micromedex DrugDex®, Elsevier Gold Standard's Clinical Pharmacology compendium, and American Hospital Formulary Service—Drug Information Compendium®.

The drug treatment options can be annotated by listing an experimental drug that may be useful in treating a cancer with one or more molecular markers of a particular status. The experimental drug can be a drug for which in vitro data, in vivo data, animal model data, pre-clinical trial data, or clinical-trial data are available. The data can be published in peer-reviewed medical literature found in journals listed in the CMS Medicare Benefit Policy Manual, including, for example, American Journal of Medicine, Annals of Internal Medicine, Annals of Oncology, Annals of Surgical Oncology, Biology of Blood and Marrow Transplantation, Blood, Bone Marrow Transplantation, British Journal of Cancer, British Journal of Hematology, British Medical Journal, Cancer, Clinical Cancer Research, Drugs, European Journal of Cancer (formerly the European Journal of Cancer and Clinical Oncology), Gynecologic Oncology, International Journal of Radiation, Oncology, Biology, and Physics, The Journal of the American Medical Association, Journal of Clinical Oncology, Journal of the National Cancer Institute, Journal of the National Comprehensive Cancer Network (NCCN), Journal of Urology, Lancet, Lancet Oncology, Leukemia, The New England Journal of Medicine, and Radiation Oncology.

The drug treatment options can be annotated by providing a link on an electronic based report connecting a listed drug to scientific information regarding the drug. For example, a link can be provided to information regarding a clinical trial for a drug (clinicaltrials.gov). If the report is provided via a computer or computer website, the link can be a footnote, a hyperlink to a website, a pop-up box, or a fly-over box with information, etc. The report and the annotated information can be provided on a printed form, and the annotations can be, for example, a footnote to a reference.

The information for annotating one or more drug treatment options in a report can be provided by a commercial entity that stores scientific information. A health care provider can treat a subject, such as a cancer patient, with an experimental drug listed in the annotated information, and the health care provider can access the annotated drug treatment option, retrieve the scientific information (e.g., print a medical journal article) and submit it (e.g., a printed journal article) to an insurance company along with a request for reimbursement for providing the drug treatment. Physicians can use any of a variety of Diagnosis-related group (DRG) codes to enable reimbursement.

A drug treatment option in a report can also be annotated with information regarding other molecular components in a pathway that a drug affects (e.g., information on a drug that targets a kinase downstream of a cell-surface receptor that is a drug target). The drug treatment option can be annotated with information on drugs that target one or more other molecular pathway components. The identification and/or annotation of information related to pathways can be outsourced or subcontracted to another company.

The annotated information can be, for example, a drug name (e.g., an FDA approved drug for off-label use; a drug found in a CMS approved compendium, and/or a drug described in a scientific (medical) journal article), scientific information concerning one or more drug treatment options, one or more links to scientific information regarding one or more drugs, clinical trial information regarding one or more drugs (e.g., information from clinicaltrials.gov/), one or more links to citations for scientific information regarding drugs, etc.

The annotated information can be inserted into any location in a report. Annotated information can be inserted in multiple locations on a report. Annotated information can be inserted in a report near a section on stratified drug treatment options. Annotated information can be inserted into a report on a separate page from stratified drug treatment options. A report that does not contain stratified drug treatment options can be annotated with information.

The system can also include reports on the effects of drugs on sample (e.g. tumor cells) isolated from a subject (e.g. cancer patient). An in vitro culture using a tumor from a cancer patient can be established using techniques known to those skilled in the art. The system can also include high-throughput screening of FDA approved off-label drugs or experimental drugs using said in vitro culture and/or xenograft model. The system can also include monitoring tumor antigen for recurrence detection.

The system can provide internet enabled access of reports of a subject with cancer. The system can use a handheld DNA sequencer or a desktop DNA sequencer. The DNA sequencer is a scientific instrument used to automate the DNA sequencing process. Given a sample of DNA, a DNA sequencer is used to determine the order of the four bases: adenine, guanine, cytosine, and thymine. The order of the DNA bases is reported as a text string, called a read. Some DNA sequencers can be also considered optical instruments as they analyze light signals originating from fluorochromes attached to nucleotides.

The data is sent by the DNA sequencers over a direct connection or over the internet to a computer for processing. The data processing aspects of the system can be implemented in digital electronic circuitry, or in computer hardware, firmware, software, or in combinations of them. Data processing apparatus of the invention can be implemented in a computer program product tangibly embodied in a machine-readable storage device for execution by a programmable processor; and data processing method steps of the invention can be performed by a programmable processor executing a program of instructions to perform functions of the invention by operating on input data and generating output. The data processing aspects of the invention can be implemented advantageously in one or more computer programs that are executable on a programmable system including at least one programmable processor coupled to receive data and instructions from and to transmit data and instructions to a data storage system, at least one input device, and at least one output device. Each computer program can be implemented in a high-level procedural or object-oriented programming language, or in assembly or machine language, if desired; and, in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented using a computer system having a display device such as a monitor or LCD (liquid crystal display) screen for displaying information to the user and input devices by which the user can provide input to the computer system such as a keyboard, a two-dimensional pointing device such as a mouse or a trackball, or a three-dimensional pointing device such as a data glove or a gyroscopic mouse. The computer system can be programmed to provide a graphical user interface through which computer programs interact with users. The computer system can be programmed to provide a virtual reality, three-dimensional display interface.

Therapeutic Intervention

The methods of this disclosure allow one to provide therapeutic interventions more precisely directed to the form of a disease in a subject, and to calibrate these therapeutic interventions over time. This precision reflects, in part, the precision by which one is able to profile the whole body tumor status of a subject as reflected in tumor heterogeneity. Thus, the therapeutic intervention is more effective against cancers with this profile than against cancers with any single one of these variants.

A therapeutic intervention is an intervention that produces a therapeutic effect, (e.g., is therapeutically effective). Therapeutically effective interventions prevent, slow the progression of, improve the condition of (e.g., causes remission of), or cure a disease, such as a cancer. A therapeutic intervention can include, for example, administration of a treatment, such as chemotherapy, radiation therapy, surgery, immunotherapy, administration of a pharmaceutical or a nutraceutical, or, a change in behavior, such as diet. One measure of therapeutic effectiveness is effectiveness for at least 90% of subjects undergoing the intervention over at least 100 subjects.

Drug targets in cancer and drugs efficacious against these targets are set forth in Tables 1 and 2 (taken from Bailey et al., Discovery Medicine, v. 18 #92, 2/7/14).

TABLE 1

Selected Examples of Commercially Available Diagnostic Tests, Associated Therapy Implication, and Relevant Cancer Type.

| Therapy Implications | Test | Cancer Type | Drug-Biomarker Clinical Association |
|---|---|---|---|
| | | IHC Assays | |
| Cetuximab; Panitumumab | EGFR | CRC | Established |
| Imatinib | C-KIT | GIST | Established |
| Trastuzumab | HER2 | Breast Cancer; Gastric Cancer | Established |
| Resistance to PI3K, AKT, and MEK inhibitors | LKB1 | NSCLC | Investigational (Mahoney et al., 2009) |
| Crizotinib | C-MET | NSCLC | Investigational (Sadiq & Salgia, 2013) |
| Akt/mTOR Inhibitors; resistance to anti- EGFR therapies | PTEN | CRC, NSCLC | Investigational (Di Nicolantonio et al., 2010; Sos et al., 2009; Wang et al., 2012) |
| | | In Situ Hybridization Assays | |
| Crizotinib | ALK Fusion FISH | NSCLC | Established |
| Trastuzumab; Pertuzumab | HER2 FISH | Breast Cancer, Gastric Cancer | Established |
| Trastuzumab | HER2 CISH | Breast Cancer | Established |
| Trastuzumab | HER2 ISH | Breast Cancer | Established |
| | | Mutation Assays | |
| Cetuximab, Panitumumab | KRAS | CRC, NSCLC, Pancreatic Cancer | Established |
| Erlotinib, Gefitinib | EGFR | NSCLC, CRC | Established |
| Vemurafenib, Trametenib, Dabrafenib, Resistance to Anti-EGFR therapies | BRAF | CRC, Thyroid Cancer, Melanoma | Established |
| Imatinib; 2nd Generation TKIs | BCR-ABL | CML, Ph+ AML | Established |
| Crizotinib | ALK | NSCLC | Established |
| RAF and MEK inhibitors, resistance to anti-EGFR therapies | NRAS | Melanoma, CRC, NSCLC | Investigational (Ascierto et al., 2013; De Mattos-Arruda et al., 2011; De Roock et al., 2010; Huang et al., 2013 ) |
| Imatinib | PDGFRA | GIST | Established |
| PI3K/mTOR Inhibitors | PIK3CA | Breast Cancer, CRC, Lung Cancer | Investigational (Di Nicolantonio et al., 2010; Janku et al., 2013) |
| Akt/mTOR Inhibitors; resistance to anti- EGFR therapies | PTEN | CRC, NSCLC, Breast | Investigational (Di Nicolantonio et al., 2010, Jerusalem et al., 2013; Sos et al., 2009; Wang et al., 2012) |

TABLE 1-continued

| Selected Examples of Commercially Available Diagnostic Tests, Associated Therapy Implication, and Relevant Cancer Type. | | | |
|---|---|---|---|
| Therapy Implications | Test | Cancer Type | Drug-Biomarker Clinical Association |
| Resistance to PI3K, AKT, and MEK inhibitors | LKB1 | NSCLC | Investigational (Averette-Byers et al., 2012) |
| | | Other | |
| Imatinib | BCR-ABL1 Quantitative Transcript Analysis | CML, Ph+ AML | Established |
| Resistance to Imatinib | BCR-ABL1 Copy Number | CML, Ph+ AML | Investigational (Hochhaus et al., 2002) |
| PI3K Inhibitors | PIK3CA Amplification | Multiple Cancer Types | Investigational (Rodon et al., 2013) |
| Erlotinib; Getfitnib; Cetuximab; Panitumumab | EGFR Amplification | NSCLC, CRC | Investigational (Gupta et al., 2009) |

Note:
The drug-biomarker clinical associations denoted 'Established' reflect well known drug FDA indications.
The ones denoted 'Investigational' are associations that are hypothesized and demonstrated by scientific literature.

TABLE 2

| US FDA Approved Targeted Therapies and Indications. | | | | |
|---|---|---|---|---|
| Agent | Trade Name | Target(s) | FDA-approved Indication(s) | Company |
| | | Monoclonal Antibodies | | |
| Ado-trastuzumab emtansine (T-DM1)* | Kadcyla | HER2 | Breast cancer (HER2+)* | Genentech |
| Bevacizumab | Avastin | VEGF | CRC<br>GBM<br>NCLC<br>RCC | Genentech |
| Cetuximab* | Erbitux | EGFR | CRC (KRAS wild-type)*<br>HNSCC | Eli Lilly |
| Ipilimumab | Yervoy | CTLA-4 | Melanoma | Bristol-Myers Squibb |
| Obinutuzumab | Gazyva | CD-20 | CLL | Genentech |
| Panitumumab* | Vectibix | EGFR | CRC (KRAS wild-type)* | Amgen |
| Pertuzumab | Perjeta | HER2 | Breast Cancer (HER2+)* | Genentech |
| Trastuzumab* | Herceptin | HER2 | Breast cancer (HER2+)*<br>Gastric cancer (HER2+)* | Genentech |
| | | Small Molecule Inhibitors | | |
| Afatinib* | Gilotrif | EGFR, HER2 | NSCLC (with EGFR exon 19 deletions or L858R substitution)* | Boehringer Ingelheim |
| Axitinib | Inlyta | KIT, PDGFRβ, VEGFR1/2/3 | RCC | Pfizer |
| Bosutinib* | Bosulif | ABL | CML (Philadelphia chromosome positive)* | Pfizer |
| Cabozantinib | Cometriq | FLT3, KIT, MET, RET, VEGFR2 | Medullary thyroid cancer | Exelixis |
| Crizotinib* | Xalkori | ALK, MET | NSCLC (with ALK fusion)* | Pfizer |
| Dabrafenib* | Tafinlar | BRAF | Melanoma (with BRAF V600E mutation)* | GlaxoStnithKline |
| Dasatinib* | Sprycel | ABL | CML (Philadelphia chromosome positive)*<br>ALL (Philadelphia chromosome positive)* | Bristol-Myers Squibb |
| Denosumab | Xgeva | RANKL | Giant cell tumor of bone | Amgen |
| Erlotinib* | Tarceva | EGFR | NSCLC (with exon 19 deletions or L858R substitutions)*<br>Pancreatic cancer | Genentech & OSI |

TABLE 2-continued

US FDA Approved Targeted Therapies and Indications.

| Agent | Trade Name | Target(s) | FDA-approved Indication(s) | Company |
|---|---|---|---|---|
| Everolimus* | Afinitor | mTOR | Pancreatic neuroendocrine tumor<br>RCC<br>Breast cancer (ER/PR+) in combination with exemestane*<br>Nonresectable subependymal giant cell astrocytoma associated with tuberous sclerosis | Novartis |
| Gefitinib | Iressa | EGFR | NSCLC with known prior benefit from gefitinib (limited approval) | AstraZeneca |
| Ibrutininb | Imbruvica | BTK | Mantle cell lymphoma | Pharmacyclics |
| Imatinib* | Gleevec | KIT, PDGFR, ABL | GI stromal tumor<br>Dermatofibrosarcoma protuberans<br>Multiple hematologic malignancies including Philadelphia chromosome-positive ALL and CML* | Novartis |
| Lapatinib* | Tykerb | HER2, EGFR | Breast cancer (HER2+)* | GlaxoSmithKline |
| Nilotinib* | Tasigna | ABL | CML (Philadelphia chromosome positive)* | Novartis |
| Pazopanib | Votrient | VEGFR, PDGFR, KIT | RCC<br>Soft tissue sarcoma | GlaxoSmithKline |
| Regorafenib | Stivarga | KIT, PDGFRβ, RAF, RET, VEGFR1/2/3 | CRC<br>Gastrointestinal stromal tumors | Bayer |
| Ruxolitinib | Jakafi | JAK1/2 | Myelofibrosis | Incyte |
| Sorafenib | Nexavar | VEGFR, PDGFR, KIT, RAF | Hepatocellular carcinoma<br>RCC | Bayer |
| Sunitinib | Sutent | VEGFR, PDGFR, KIT, RET | GIST<br>Pancreatic neuroendocrine tumor<br>RCC | Pfizer |
| Temsirolimus | Torisel | mTOR | RCC | Wyeth |
| Trametinib* | Mekinist | MEK | Melanoma (with BRAF V600E or V600K mutations)* | GlaxoSmithKline |
| Vandetanib | Caprelsa | EGFR RET, VEGFR2 | Medullary thyroid cancer | AstraZeneca |
| Vemurafenib* | Zelboraf | BRAF | Melanoma (with BRAF V600 mutation)* | Roche |

Note:
ALL, acute lymphoblastic leukemia; CML, chronic myeloid leukemia; GIST, gastrointestinal stromal tumor; ER, estrogen receptor; PR, progesterone receptor; NSCLC, non-small cell lung cancer; CRC, colorectal cancer; GBM, glioblastoma; RCC, renal cell carcinoma; HNSCC, head and neck squamous cell carcinoma; CLL, chronic lymphoblastic leukemia; BTK, Bruton's tyrosine kinase.
*Targeted therapy that is associated with a molecular-specific cancer subtype alteration. There are approximately 17 targeted therapies that are associated with 10 molecular-specific subtypes of cancer.

In one embodiment, based on the profile of disease heterogeneity, a therapeutic intervention is determined that takes into account both the type of genetic variants found in the disease cells and their relative amounts (e.g., proportion). The therapeutic intervention can treat the subject as if each clonal variant were a different cancer to be treated independently. In some cases, when one or more genetic variants are detected at less than sub-clinical amounts, e.g., at least 5× lower, at least 10× lower, or at least 100× lower than the dominant detected clones, these variants may be left out of the therapeutic intervention until they rise to a clinical threshold or significant relative frequency (e.g., greater than the threshold stated above).

When a plurality of different genetic variants is found in different quantities, e.g., different numbers or different relative amounts, a therapeutic intervention can include treatments effective against diseases with each of the genetic variants. For example, in the case of cancer, genetic variants, such as mutant forms of a gene or gene amplification, may be detected in several genes (e.g., a major clone and a minor clone). Each of these forms may be actionable, that is, a treatment may be known for which cancers with the particular variant are responsive. However, the profile of tumor heterogeneity may indicate that one of the variants is present in the polynucleotides at, for example, five times the level of each of the other two variants. A therapeutic intervention can be determined that involves delivering three different drugs to the subject, each drug relatively more effective against cancers bearing each of the variants. The drugs can be delivered as a cocktail, or sequentially.

In a further embodiment, the drugs can be administered in doses stratified to reflect the relative amounts of the variants in the DNA. For example, a drug effective against the most common variant can be administered in greater amount than drugs effective against the two less common variants.

Alternatively, the profile of tumor heterogeneity can show the presence of a sub-population of cancer cells bearing a genetic variant that is resistant to a drug to which the disease typically responds. In this case, the therapeutic intervention can involve including both a first drug effective against tumor cells without the resistance variant and a second drug effective against tumor cells with the resistant variant. Again, doses can be stratified to reflect relative amounts of each variant detected in the profile.

In another embodiment, changes in the profile of tumor heterogeneity are examined over time, and therapeutic interventions are developed to treat the changing tumor. For example, disease heterogeneity can be determined at a plurality of different times. Using the profiling methods of this disclosure, more precise inferences can be made about tumor evolution. This allows the practitioner to monitor the evolution of the disease, in particular as new clonal subpopulations emerge after remission effected by a first wave of therapy. In this case, therapeutic interventions can be calibrated over time to treat the changing tumor. For example, a profile may show that a cancer has a form that is responsive to a certain treatment. The treatment is delivered and the tumor burden is seen to decrease over time. At some point, a genetic variant is found in the tumor indicating the presence of a population of cancer cells that is not responsive to the treatment. A new therapeutic intervention is determined that targets the cells bearing the marker of non-responsiveness.

In response to chemotherapy, a dominant tumor form can eventually give way through Darwinian selection to cancer cells carrying mutants that render the cancer unresponsive to the therapy regimen. Appearance of these resistance mutants can be delayed through methods of this disclosure. In one embodiment of this method, a subject is subjected to one or more pulsed therapy cycles, each pulsed therapy cycle comprising a first period during which a drug is administered at a first amount and a second cycle during which the drug is administered at a second, reduced amount. The first period is characterized by a tumor burden detected above a first clinical level. The second period is characterized by a tumor burden detected below a second clinical level. First and second clinical levels can be different in different pulsed therapy cycles. So, for example, the first clinical level can be lower in succeeding cycles. A plurality of cycles can include at least 2, 3, 4, 5, 6, 7, 8 or more cycles. For example, the BRAF mutant V600E may be detected in disease cell polynucleotides at an amount indicating a tumor burden of 5% in cfDNA. Chemotherapy can commence with dabrafenib. Subsequent testing can show that the amount of the BRAF mutant in the cfDNA falls below 0.5% or to undetectable levels. At this point, dabrafenib therapy can stop or be significantly curtailed. Further subsequent testing may find that DNA bearing the BRAF mutation has risen to 2.5% of polynucleotides in cfDNA. At this point, dabrafenib therapy is re-started, e.g., at the same level as the initial treatment. Subsequent testing may find that DNA bearing the BRAF mutation has decreased to 0.5% of polynucleotides in cfDNA. Again, dabrafenib therapy is stopped or reduced. The cycle can be repeated a number of times.

Figure 7:
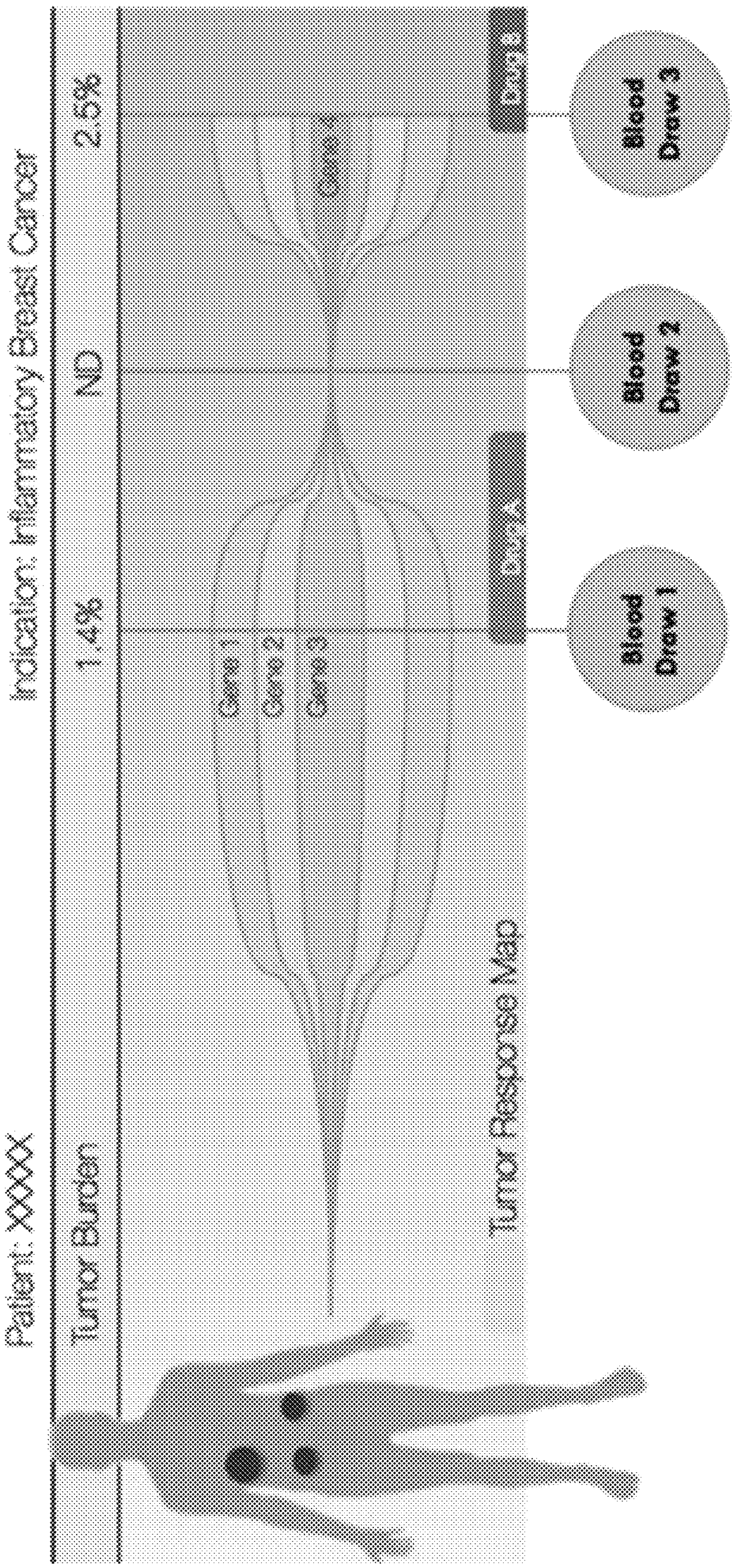
FIG. 7 shows an exemplary course of monitoring and treatment of disease in a subject.

FIG. 7 shows an exemplary course of monitoring and treatment of disease in a subject. A subject tested at the time of blood draw 1 has a tumor burden of 1.4% and presents with genetic alterations in genes 1, 2 and 3. The subject is treated with Drug A. After a time, treatment is discontinued. At a second later time, a second blood draw shows the cancer in remission. At a third later time, a third blood draw indicates that the cancer has recurred, in this instance, presenting with a genetic variant in Gene 4. The subject is now put on a course of Drug B, to which cancers having this variant are responsive.

In another embodiment, a therapeutic intervention can be changed upon detection of the rise of a mutant form resistant to an original drug. For example, cancers with the EGFR mutation L858R respond to therapy with erlotinib. However, cancers with the EGFR mutation T790M are resistant to erlotinib. However, they are responsive to ruxolitinib. A method of this disclosure involves monitoring changes in tumor profile and changing a therapeutic intervention when a genetic variant associated with drug resistance rises to a predetermined clinical level.

Database

In another embodiment, a database is built in which genetic information from serial samples collected from cancer patients is recorded. This database may also contain intervening treatment and other clinically relevant information, such as, weight, adverse effects, histological testing, blood testing, radiographic information, prior treatments, cancer type, etc. Serial test results can be used to infer efficacy of treatment, especially when used with blood samples, which can give a more unbiased estimate of tumor burden than self-reporting or radiographic reporting by a medical practitioner. Treatment efficacy can be clustered by those with similar genomic profiles and vice versa. Genomic profiles can be organized around, for example, primary genetic alteration, secondary genetic alteration(s), relative amounts of these genetic alterations, and tumor load. This database can be used for decision support for subsequent patients. Both germline and somatic alterations can be used for determining treatment efficacy as well. Acquired resistance alterations that can also be inferred from the database when treatments that were effective initially begin to fail. This failure can be detected through radiographic, blood or other means. The primary data used for inference of acquired resistance mechanisms are genomic tumor profiles collected after treatment per patient. This data can also be used to place quantitative bounds on likely treatment response as well as predict time to treatment failure. Based on likely acquired resistance alterations for a given treatment and tumor genomic profile, a treatment regimen can be modified to suppress acquisition of most likely resistance alterations.

Computer Systems

Figure 5:
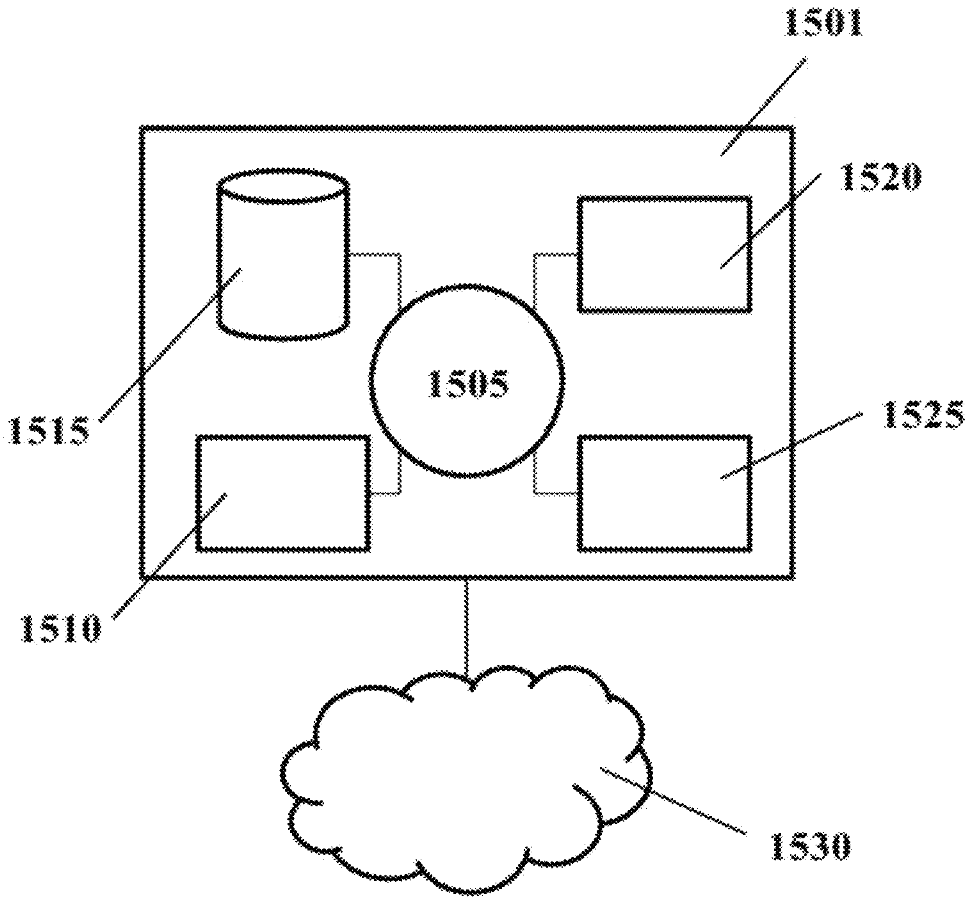
FIG. 5 shows an exemplary computer system.
Figure 6:
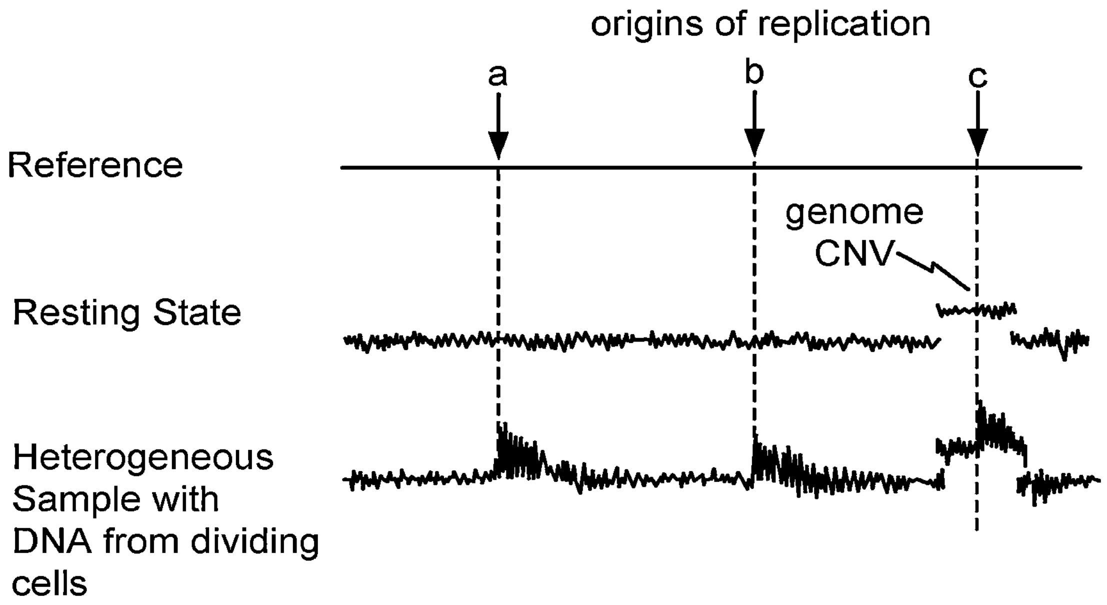
FIG. 6 shows an exemplary scan of CNV across a region of a genome from samples containing cells in a resting state and in a state of cell division. No genomic CNV is seen in loci a and b, but locus c shows gene duplication. In the resting state cells, copy number is relatively equal in all intervals in the region, except those intervals overlapping the locus of gene duplication. In the sample containing DNA from tumor cells, which are undergoing cell division, copy number appears to increase immediately after origins of replication, providing variance in CNV over the region. Deviation is particularly dramatic at a locus exhibiting CNV at an origin of replication (c).

Methods of the present disclosure can be implemented using, or with the aid of, computer systems. FIG. 5 shows a computer system 1501 that is programmed or otherwise configured to implement the methods of the present disclosure. The computer system 1501 includes a central processing unit (CPU, also "processor" and "computer processor" herein) 1505. The computer system 1501 also includes memory or memory location 1510 (e.g., random-access memory, read-only memory, flash memory), electronic storage unit 1515 (e.g., hard disk), communication interface 1520 (e.g., network adapter) for communicating with one or more other systems, and peripheral devices 1525, such as cache, other memory, data storage and/or electronic display adapters. The memory 1510, storage unit 1515, interface 1520 and peripheral devices 1525 are in communication with the CPU 1505 through a communication bus (solid lines). The storage unit 1515 can be a data storage unit (or data repository) for storing data. The computer system 1501 can be operatively coupled to a computer network ("network") 1530 with the aid of the communication interface 1520. The network 1530 can be the Internet, an internet and/or extranet, or an intranet and/or extranet that is in communication with the Internet. The network 1530 in some cases is a telecommunication and/or data network. The network 1530 can include one or more computer servers, which can enable distributed computing, such as cloud computing. The CPU 1505 can execute a sequence of machine-readable instructions, which can be embodied in a program or software. The instructions may be stored in a memory location, such as the memory 1510. The storage unit 1515 can store files, such as drivers, libraries and saved programs. The computer system 1501 can communicate with one or more remote computer systems through the network 1530. Methods as described herein can be implemented by way of machine (e.g., computer processor) executable code stored on an electronic storage location of the computer system 1501, such as, for example, on the memory 1510 or electronic storage unit 1515. The machine executable or machine readable code can be provided in the form of software. Aspects of the systems and methods provided herein, such as the computer system 1501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. The computer system 1501 can include or be in communication with an electronic display that comprises a user interface (UI) for providing, for example, one or more results of sample analysis.

EXAMPLES

Nucleotide positions (e.g., loci) in the genome can be designated by number, as depicted in FIG. 2. Positions at which about 100% of the base calls are identical to the reference sequence or at which about 100% of the base calls are different than the reference sequence are inferred to represent homozygosity of the cfDNA (presumed normal). Positions at which about 50% of the base calls are identical to the reference sequence are inferred to represent heterozygosity of the cfDNA (also presumed normal). Positions at which the percentage of base calls at a locus are substantially below 50% and above the detection limit of the base calling system are inferred to represent tumor-associated genetic variants.

Example 1. Methods for Copy Number Variation Detection

Blood Collection 10-30 mL Blood samples are collected at room temperature. The samples are centrifuged to remove cells. Plasma is collected after centrifugation.

cfDNA Extraction

The sample is subjected to proteinase K digestion. DNA is precipitated with isopropanol. DNA is captured on a DNA purification column (e.g., a QIAamp DNA Blood Mini Kit) and eluted in 100 μl solution. DNAs below 500 bp are selected with Ampure SPRI magnetic bead capture (PEG/salt). The resulting production is suspended in 30 μl $H_2O$. Size distribution is checked (major peak=166 nucleotides; minor peak=330 nucleotides) and quantified. 5 ng of extracted DNA contain approximately 1700 haploid genome equivalents ("HGE"). The general correlation between the amount of DNA and HGE is as follow: 3 pg DNA=1 HGE; 3 ng DNA=1K HGE; 3 μg DNA=1M HGE; 10 pg DNA=3 HGE; 10 ng DNA=3K HGE; 10 μg DNA=3M HGE.

"Single Molecule" Library Prep

High-efficiency DNA tagging (>80%) is performed by end repair, A-tailing and sticky-end ligation with 2 different octomers (i.e., 4 combinations) with overloaded hairpin adaptors. 2.5 ng DNA (i.e. approximately 800 HGE) is used as the starting material. Each hairpin adaptor comprises a random sequence on its non-complementary portion. Both ends of each DNA fragment are attached with hairpin adaptors. Each tagged fragment can be identified by a combination of the octomer sequence on the hairpin adaptors and endogenous portions of the insert sequence.

Tagged DNA is amplified by 12 cycles of PCR to produce about 1-7 μg DNA that contain approximately 500 copies of each of the 800 HGE in the starting material.

Buffer optimization, polymerase optimization and cycle reduction may be performed to optimize the PCR reactions. Amplification bias, e.g., non-specific bias, GC bias, and/or size bias are also reduced by optimization. Noise(s) (e.g., polymerase-introduced errors) are reduced by using high-fidelity polymerases.

Sequences may be enriched as follow: DNAs with regions of interest (ROI) are captured using biotin-labeled bead with probe to ROIs. The ROIs are amplified with 12 cycles of PCR to generate a 2000 times amplification.

Massively Parallel Sequencing 0.1 to 1% of the sample (approximately 100 pg) are used for sequencing. The resulting DNA is then denatured and diluted to 8 pM and loaded into an Illumina sequencer.

Digital Bioinformatics

Sequence reads are grouped into families, with about 10 sequence reads in each family. Families are collapsed into consensus sequences by voting (e.g., biased voting) each position in a family. A base is called for consensus sequence if 8 or 9 members agree. A base is not called for consensus sequence if no more than 60% of the members agree.

The resulting consensus sequences are mapped to a reference genome, such as hg19. Each base in a consensus sequence is covered by about 3000 different families. A quality score for each sequence is calculated and sequences are filtered based on their quality scores. Base calls at each position in a consensus sequence are compared with the HG-19 reference sequence. At each position at which a base call differs from the reference sequence, the identity of the different base or bases, and their percentage as a function of total base calls at the locus is determined and reported.

Sequence variation is detected by counting distribution of bases at each locus. If 98% of the reads have the same base (homozygous) and 2% have a different base, the locus is likely to have a sequence variant, presumably from cancer DNA.

CNV is detected by counting the total number of sequences (bases) mapping to a locus and comparing with a control locus. To increase CNV detection, CNV analysis is performed specific regions, including regions on ALK, APC, BRAF, CDKN2A, EGFR, ERBB2, FBXW7, KRAS, MYC, NOTCH1, NRAS, PIK3CA, PTEN, RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET, SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, or NTRK1 genes.

Example 2. Method for Correcting Base Calling by Determining the Total Number Unseen Molecules in a Sample After fragments are amplified and the sequences of amplified fragments are read and aligned, the fragments are subjected to base calling. Variations in the number of amplified fragments and unseen amplified fragments can introduce errors in base calling. These variations are corrected by calculating the number of unseen amplified fragments.

When base calling for locus A (an arbitrary locus), it is first assumed that there are N amplified fragments. The sequence readouts can come from two types of fragments: double-strand fragments and single-strand fragments. The following is a theoretical example of calculating the total number of unseen molecules in a sample.

N is the total number of molecules in the sample.

Assuming 1000 is the number of duplexes detected.

Assuming 500 is the number of single-stranded molecule detected.

P is the probability of seeing a strand.

Q is the probability of not detecting a strand.

Since $Q=1-P.$ $1000=NP(2).$ $500=N2PQ.$ $1000/P(2)=N.$ $500\div 2PQ=N.$ $1000/P(2)=500\div 2PQ.$ $1000*2PQ=500P(2).$ $2000PQ=500P(2).$ $2000Q=500P.$ $2000(1-P)=500P$ $2000-2000P=500P.$ $2000=500P+2000P.$ $2000=2500P.$ $2000\div 2500=P.$ $0.8=P.$ $1000/P(2)=N.$ $1000\div 0.64=N.$ $1562=N.$ Number of unseen fragments=62.

Example 3. Identification of Genetic Variants in Cancer-Associated Somatic Variants in a Patient An assay is used to analyze a panel of genes to identify genetic variants in cancer-associated somatic variants with high sensitivity.

Cell-free DNA is extracted from plasma of a patient and amplified by PCR. Genetic variants are analyzed by massively parallel sequencing of the amplified target genes. For one set of genes, all exons are sequenced as such sequencing coverage had shown to have clinically utility (Table 3). For another set of genes, sequencing coverage included those exons with a previously reported somatic mutation (Table 4). The minimum detectable mutant allele (limit of detection) is dependent on the patient's sample cell-free DNA concentration, which varied from less than 10 to over 1,000 genomic equivalents per mL of peripheral blood. Amplification may not be detected in samples with lower amounts of cell-free DNA and/or low-level gene copy amplification. Certain sample or variant characteristics resulted in reduced analytic sensitivity, such as low sample quality or improper collection.

The percentage of genetic variants found in cell-free DNA circulating in blood is related to the unique tumor biology of this patient. Factors that affected the amount/percentages of detected genetic variants in circulating cell-free DNA in blood include tumor growth, turnover, size, heterogeneity, vascularization, disease progression or treatment. Table 5 annotates the percentage, or allele frequency, of altered circulating cell-free DNA (% cfDNA) detected in this patient. Some of the detected genetic variants are listed in descending order by % cfDNA.

Genetic variants are detected in the circulating cell-free DNA isolated from this patient's blood specimen. These genetic variants are cancer-associated somatic variants, some of which have been associated with either increased or reduced clinical response to specific treatment. "Minor Alterations" are defined as those alterations detected at less than 10% the allele frequency of "Major Alterations". A Major Alteration is the predominant alteration at a locus. The detected allele frequencies of these alterations (Table 5) and associated treatments for this patient are annotated.

All genes listed in Tables 3 and 4 are analyzed as part of the test. Amplification is not detected for ERBB2, EGFR, or MET in the circulating cell-free DNA isolated from this patient's blood specimen.

Patient test results comprising the genetic variants are listed in Table 6.

Referring to Table 4, at 13 positions, a nucleotide detected at at least 98.8% frequency in the sample is different than a nucleotide in the reference sequence, indicating homozygosity at these loci. For example, in the KRAS gene, at position 25346462, T was detected rather than reference nucleotide C in 100% of cases.

At 35 positions, a nucleotide detected at between 41.4% and 55% frequency in the sample is different than a nucleotide in the reference sequence, indicating heterozygosity at these loci. For example, in the ALK gene, at position 29455267, G was detected rather than reference nucleotide A in 50% of cases.

At 3 positions a nucleotide detected at less than 9% frequency is different than a nucleotide in the reference sequence. These include variants in BRAF (140453136 A>T, 8.9%), NRAS (115256530 G>T 2.6%) and JAK2 (5073770 G>T 1.5%). They are presumed to be somatic mutations from cancer DNA.

The relative amounts of tumor-associated genetic variants are calculated. The ratio of amounts of BRAF:NRAS:JAK2 is 8.9:2.6:1.5, or 1:0.29:0.17. From this result one can infer the presence of tumor heterogeneity. For example, one possible interpretation is that 100% of tumor cells contain a variant in BRAF, 83% contain variants in BRAF and NRAS, and 17% contain variants in BRAF, NRAS and JAK2. However, analysis of CNV may show amplification of BRAF, in which case 100% of tumor cells may have variants in both BRAF and NRAS.

TABLE 3

| Genes in which all exons are sequenced<br>GENES IN WHICH ALL EXONS ARE SEQUENCED | | | |
|---|---|---|---|
| Gene | LOD | Gene | LOD |
| ALK | <0.1% | APC | <0.1% |
| AR | <0.1% | BRAF | <0.1% |
| CDKN2A | <0.1% | EGFR | <0.1% |
| ERBB2 | <0.1% | FBXW7 | <0.1% |
| KRAS | <0.1% | MET | <0.1% |
| MYC | <0.1% | NOTCH1 | <0.1% |
| NRAS | <0.1% | PIK3CA | <0.1% |
| PTEN | <0.1% | PROC | <0.1% |
| RB1 | <0.1% | TP53 | <0.1% |

LOD: Limit of Detection. The minimum detectable mutant allele frequency for this specimen in which 80% of somatic variants is detected.

TABLE 4

| Genes in which exons with a previously reported somatic mutation are sequenced<br>GENES IN WHICH EXONS WITH A PREVIOUSLY REPORTED SOMATIC MUTATION ARE SEQUENCED | | | |
|---|---|---|---|
| Gene | LOD | Gene | LOD |
| ABL1 | <0.1% | AKT1 | <0.1% |
| ATM | <0.1% | CDH1 | <0.1% |
| CSF1R | <0.1% | CTNNB1 | <0.1% |
| ERBB4 | <0.1% | EZH2 | <0.1% |
| FGFR1 | <0.1% | FGFR2 | <0.1% |
| FGFR3 | <0.1% | FLT3 | <0.1% |
| GNA11 | <0.1% | GNAQ | <0.1% |

TABLE 4-continued

| Genes in which exons with a previously reported somatic mutation are sequenced<br>GENES IN WHICH EXONS WITH A PREVIOUSLY REPORTED SOMATIC MUTATION ARE SEQUENCED | | | |
|---|---|---|---|
| Gene | LOD | Gene | LOD |
| GNAS | <0.1% | HNF1A | <0.1% |
| HRAS | <0.1% | IDH1 | <0.1% |
| IDH2 | <0.1% | JAK2 | <0.1% |
| JAK3 | <0.1% | KDR | <0.1% |
| KIT | <0.1% | MLH1 | <0.1% |
| MPL | <0.1% | NPM1 | <0.1% |
| PDGFRA | <0.1% | PTPN11 | <0.1% |
| RET | <0.1% | SMAD4 | <0.1% |
| SMARCB1 | <0.1% | SMO | <0.1% |
| SRC | <0.1% | STK11 | <0.1% |
| TERT | <0.1% | VHL | <0.1% |

LOD: Limit of Detection. The minimum detectable mutant allele frequency for this specimen in which 80% of somatic variants is detected.

TABLE 5

| Allele frequency of altered circulating cell-free DNA detected in this patient | | |
|---|---|---|
| Gene | cfDNA with alterations (%) | cfDNA without alterations (%) |
| BRAF V600E | 8.9 | 91.1 |
| NRAS Q61K | 6.2 | 93.8 |
| JAK V617F | 1.5 | 98.6 |

TABLE 6

| Genomic alterations detected in selected genes<br>Detected: 51 Genomic Alterations | | | | | | | |
|---|---|---|---|---|---|---|---|
| Gene | Chromosome | Position | Mutation (nt) | Mutation (AA) | Percentage | Cosmic ID | DBSNP ID |
| KRAS | 12 | 25368462 | C > T | | 100.0% | | rs4362222 |
| ALK | 2 | 29416572 | T > C | I1461V | 100.0% | | rs1670283 |
| ALK | 2 | 29444095 | C > T | | 100.0% | | rs1569156 |
| ALK | 2 | 29543663 | T > C | Q500Q | 100.0% | | rs2293564 |
| ALK | 2 | 29940529 | A > T | P234P | 100.0% | | rs2246745 |
| APC | 5 | 112176756 | T > A | V1822D | 100.0% | | rs459552 |
| CDKN2A | 9 | 21968199 | C > G | | 100.0% | COSM14251 | rs11515 |
| FGFR3 | 4 | 1807894 | G > A | T651T | 100.0% | | rs7688609 |
| NOTCH1 | 9 | 139410424 | A > G | | 100.0% | | rs3125006 |
| PDGFRA | 4 | 55141055 | A > G | P567P | 100.0% | | rs1873778 |
| HRAS | 11 | 534242 | A > G | H27H | 100.0% | COSM249860 | rs12628 |
| EGFR | 7 | 55214348 | C > T | N158N | 99.9% | COSM42978 | rs2072454 |
| TP53 | 17 | 7579472 | G > C | P72R | 99.8% | | rs1042522 |
| APC | 5 | 112162854 | T > C | Y486Y | 55.0% | | rs2229992 |
| APC | 5 | 112177171 | G > A | P1960P | 53.8% | | rs465899 |
| EGFR | 7 | 55266417 | T > C | T903T | 53.6% | | rs1140475 |
| APC | 5 | 112176325 | G > A | G1678G | 53.2% | | rs42427 |
| APC | 5 | 112176559 | T > G | S1756S | 53.0% | | rs866006 |
| EGFR | 7 | 55229255 | G > A | R521K | 53.0% | | |
| MET | 7 | 116397572 | A > G | Q648Q | 52.7% | | |
| APC | 5 | 112175770 | G > A | T1493T | 52.7% | | rs41115 |
| EGFR | 7 | 55249063 | G > A | Q787Q | 52.6% | | rs1050171 |
| NOTCH1 | 9 | 139411714 | T > C | | 52.4% | | rs11145767 |
| EGFR | 7 | 55238874 | T > A | T629T | 52.0% | | rs2227984 |
| ERBB2 | 17 | 37879588 | A > G | I655V | 51.6% | | rs1136201 |
| NOTCH1 | 9 | 139397707 | G > A | D1698D | 51.3% | COSM33747 | rs10521 |
| ALK | 2 | 30143499 | G > C | L9L | 51.0% | | rs4358080 |
| APC | 5 | 112164561 | G > A | A545A | 51.0% | | rs351771 |
| FLT3 | 13 | 28610183 | A > G | | 50.8% | | rs2491231 |
| NOTCH1 | 9 | 139418260 | A > G | N104N | 50.5% | | rs4489420 |
| ALK | 2 | 29444076 | G > T | | 50.4% | | rs1534545 |
| PIK3CA | 3 | 178917005 | A > G | | 50.3% | | rs3729674 |
| NOTCH1 | 9 | 139412197 | G > A | | 50.2% | | rs9411208 |
| ALK | 2 | 29455267 | A > G | G845G | 50.0% | COSM148825 | rs2256740 |
| KIT | 4 | 55593464 | A > C | M541L | 49.9% | COSM28026 | |

TABLE 6-continued

Genomic alterations detected in selected genes
Detected: 51 Genomic Alterations

| Gene | Chromosome | Position | Mutation (nt) | Mutation (AA) | Percentage | Cosmic ID | DBSNP ID |
|---|---|---|---|---|---|---|---|
| NOTCH1 | 9 | 139391636 | G > A | D2185D | 48.9% | | rs2229974 |
| PDGFRA | 4 | 55152040 | C > T | V824V | 48.9% | COSM22413 | rs2228230 |
| ALK | 2 | 29416481 | T > C | K1491R | 48.9% | COSM1130802 | rs1881420 |
| ALK | 2 | 29445458 | G > T | G1125G | 48.6% | | rs3795850 |
| NOTCH1 | 9 | 139410177 | T > C | | 48.5% | | rs3124603 |
| RET | 10 | 43613843 | G > T | L769L | 48.2% | | rs1800861 |
| EGFR | 7 | 55214443 | G > A | | 48.0% | | rs7801956 |
| ALK | 2 | 29416366 | G > C | D1529E | 47.2% | | rs1881421 |
| EGFR | 7 | 55238087 | C > T | | 45.5% | | rs10258429 |
| RET | 10 | 43615633 | C > G | S904S | 44.8% | | rs1800863 |
| BRAF | 7 | 140453136 | A > T | V600E | 8.9% | COSM476 | |
| NRAS | 1 | 115256530 | G > T | Q61K | 6.2% | COSM580 | rs121913254 |
| JAK2 | 9 | 5073770 | G > T | V617F | 1.5% | COSM12600 | rs77375493 |

Example 4. Determining Patient-Specific Limits of Detection for Genes Analyzed by Assays Using the method of Example 3, Genetic alterations in cell-free DNA of a patient are detected. The sequence reads of these genes include exon and/or intron sequences.

Example 5. Correcting Sequence Errors Comparing Watson and Crick Sequences

Double-stranded cell-free DNA is isolated from the plasma of a patient. The cell-free DNA fragments are tagged using 16 different bubble-containing adaptors, each of which comprises a distinctive barcode. The bubble-containing adaptors are attached to both ends of each cell-free DNA fragment by ligation. After ligation, each of the cell-free DNA fragment can be distinctly identified by the sequence of the distinct barcodes and two 20 bp endogenous sequences at each end of the cell-free DNA fragment.

The tagged cell-free DNA fragments are amplified by PCR. The amplified fragments are enriched using beads comprising oligonucleotide probes that specifically bind to a group of cancer-associated genes. Therefore, cell-free DNA fragments from the group of cancer-associated genes are selectively enriched.

Sequencing adaptors, each of which comprises a sequencing primer binding site, a sample barcode, and a cell-flow sequence, are attached to the enriched DNA molecules. The resulting molecules are amplified by PCR.

Both strands of the amplified fragments are sequenced. Because each bubble-containing adaptor comprises a non-complementary portion (e.g., the bubble), the sequence of the one strand of the bubble-containing adaptor is different from the sequence of the other strand (complement). Therefore, the sequence reads of amplicons derived from the Watson strand of an original cell-free DNA can be distinguished from amplicons from the Crick strand of the original cell-free DNA by the attached bubble-containing adaptor sequences.

The sequence reads from a strand of an original cell-free DNA fragment are compared to the sequence reads from the other strand of the original cell-free DNA fragment. If a variant occurs in only the sequence reads from one strand, but not other strand, of the original cell-free DNA fragment, this variant will be identified as an error (e.g., resulted from PCR and/or amplification), rather than a true genetic variant.

The sequence reads are grouped into families. Errors in the sequence reads are corrected. The consensus sequence of each family is generated by collapsing.

Example 6. Therapeutic Intervention

A therapeutic intervention is determined to treat the cancer. Cancers with BRAF mutants respond to treatment with vemurafenib, regorafenib, trametinib and dabrafenib. Cancers with NRAS mutants respond to treatment with trametinib. Cancers with JAK2 mutants respond to treatment with ruxolitinib. A therapeutic intervention including administration of trametinib and ruxolitinib is determined to be more effective against this cancer than treatment with any one of the aforementioned drugs alone. The subject is treated with a combination of trametinib and ruxolitinib at a dose ratio of 5:1.

After several rounds of treatment, the cfDNA from the subject is tested again for the presence of tumor heterogeneity. Results show that the ratio of the BRAF:NRAS:JAK2 is now about 4:2:1.5. This indicates that the therapeutic intervention has reduced the number of cells with the BRAF and NRAS mutants, and has halted growth of cells with JAK2 mutants. A second therapeutic intervention is determined in which trametinib and ruxolitinib are determined to be effective in a dose ratio of 1:1. The subject is given a course of chemotherapy at amounts at this ratio. Subsequent testing shows that BRAF, NRAS and JAK2 mutants are present in cfDNA at amounts below 1%.

Example 7. Therapeutic Intervention

A blood sample is collected from an individual with melanoma pre-treatment and the patient is determined to have a BRAF V600E mutation at a concentration of 2.8% and no detectable NRAS mutations using cell-free DNA analysis. The patient is put on an anti-BRAF therapy (dabrafenib). After 3 weeks, another blood sample is collected and tested. The BRAF V600E level is determined to have dropped to 0.1%. The therapy is stopped and the test repeated every 2 weeks. The BRAF V600E level rises again and therapy is reinitiated when the BRAF V600E level rises to 1.5%. Therapy is again stopped when the level drops down to 0.1% again. This cycle is repeated.

Example 8. Correcting CNV Based on ROCNV Measurements

Copy number variations in a patient sample are determined. Methods for determining can include molecular tracking and upsampling, as described above. A hidden-markov model based on expected locations of origins of replication is used to remove the effect of replication origin proximity from the estimated copy number variations in the patient sample. The standard deviation of copy-number variations for each gene is subsequently reduced by 40%. The replication origin proximity model is also used to infer cell-free tumor burden in the patient.

In many cases, the level of cell-free tumor derived may be low or below the detection limit of a particular technology. This can be the case when the number of human genome equivalents of tumor derived DNA in plasma is below 1 copy per 5 mL. Radiation and chemotherapies have been shown to affect rapidly dividing cells more than stable, healthy cells, hence their efficacy in treating advanced cancer patients. Hence, a procedure with minimal adverse effects is administered to a patient pre-blood collection to preferentially increase the fraction of tumor-derived DNA collected. For example, a low dose of chemotherapy could be administered to the patient and a blood sample could be collected within 24 hours, 48 hours, 72 hours or less than 1 week. For effective chemotherapies, this blood sample contains higher concentrations of cell-free tumor-derived DNA due to potentially higher rates of cell-death of cancer cells. Alternatively, low-dose radiation therapy is applied via a whole-body radiographic instrument or locally to the affected regions instead of low-dose chemotherapy. Other procedures are envisioned, including subjecting a patient to ultrasound, sound waves, exercise, stress, etc.

All publications, patents, and patent applications mentioned in this specification are herein incorporated by reference to the same extent as if each individual publication, patent, or patent application was specifically and individually indicated to be incorporated by reference.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of identifying efficacy of a given intervention for a cancer in a patient, comprising:

a) accessing a database comprising data for a plurality of subjects having the same type of cancer as the patient, wherein the data comprises for each of the plurality of subjects:
   i. two or more tumor genomic profiles collected at two or more time intervals using serial biopsy of cell-free DNA, wherein the cell-free DNA was tagged or tracked with molecular barcodes to permit subsequent identification of a particular polynucleotide and, wherein the molecular barcodes track back to single original cell-free nucleic acid molecules,
   ii. data associated with one or more therapeutic interventions administered at one or more times, and
   iii. data associated with efficacy of the one or more therapeutic interventions;

b) applying a machine learning algorithm to a feature vector that comprises the patient's somatic alterations and a temporal change metric for each alteration equal to a difference in its relative variant frequency between at least a first and a second cfDNA biopsy of the patient, wherein the machine learning algorithm comprises a support vector machine that has been trained, using the data associated with the one or more therapeutic interventions and the data associated with the efficacy of the one or more therapeutic interventions from the database, to infer efficacy of a given therapeutic intervention in the patient and to predict tumor genomic evolution or acquired resistance mechanisms; and c) generating a report comprising the inferred efficacy of the given therapeutic intervention for the patient to predict tumor genomic evolution or acquired resistance mechanisms.

2. The method of claim 1, wherein the plurality of subjects is at least 5,000 subjects.

3. The method of claim 1, wherein weight, adverse treatment effects, histological testing, blood testing, radiographic information, prior treatments, and/or cancer type is used to classify treatment efficacy.

4. The method of claim 1, wherein treatment response per subject is collected and classified quantitatively through additional testing, wherein the additional testing is blood or urine based testing.

5. The method of claim 1, further comprising administering the one or more effective therapeutic interventions to the cancer patient based on the report.

6. The method of claim 1, wherein applying the machine learning algorithm further comprises normalizing the patient's temporal change metric using a scaling factor derived from sequencing platform calibration data or control samples.

7. A method of identifying one or more effective therapeutic interventions for a cancer in a patient comprising:

a) obtaining a sample from the patient;

b) accessing a database comprising data for a plurality of subjects having the same type of cancer as the patient, wherein the data comprises for each of the plurality of subjects:
   i. two or more tumor genomic profiles collected at two or more time intervals per subject using serial biopsy of cell-free DNA, wherein the cell-free DNA was tagged or tracked with molecular barcodes to permit subsequent identification of the particular polynucleotide and, wherein the molecule barcodes track back to single original cell-free nucleic acid molecules,
   ii. data associated with one or more therapeutic interventions administered to each of the subjects at one or more times, and
   iii. data associated with efficacy of the one or more therapeutic interventions;

c) applying a machine learning algorithm to a feature vector that comprises the patient's somatic alterations and a temporal change metric for each alteration equal to a difference in its relative variant frequency between at least a first and a second cfDNA biopsy of the patient, wherein the machine learning algorithm comprises a support vector machine, to infer efficacy of one or more effective therapeutic interventions for the patient and to predict tumor genomic evolution or acquired resistance mechanisms.

8. The method of claim 7, wherein identified therapeutic interventions are stratified by efficacy.

9. The method of claim 7, wherein quantitative bounds on predicted therapeutic interventions efficacy or lack thereof are reported.

10. The method of claim 7, wherein the plurality of subjects is at least 5,000 subjects.

11. The method of claim 7, wherein weight, adverse treatment effects, histological testing, blood testing, radiographic information, prior treatments, and/or cancer type is used to help classify treatment efficacy.

12. The method of claim 7, wherein treatment response per subject is collected and classified quantitatively through additional testing, wherein the additional testing is blood or urine based testing.

13. The method of claim 7, wherein support vector machine has been trained, using the data associated with the one or more therapeutic interventions and the data associated with the efficacy of the one or more therapeutic interventions from the database.

14. The method of claim 7, wherein both germline and somatic alterations are used to determine treatment efficacy.

15. The method of claim 7, wherein acquired resistance alterations are inferred from the database when treatments that were effective in the plurality of subjects began to fail.

16. The method of claim 7, wherein the tumor genomic testing profiles comprise DNA sequencing data which includes polynucleotides mapping to specific loci of the genome that are the subject of interest, and have been isolated for sequencing by sequence capture or site-specific amplification.

17. The method of claim 7, wherein the one or more therapeutic interventions are experimental drugs.

18. The method of claim 7, comprising grouping information from the molecular barcodes.

19. The method of claim 18, wherein the molecular barcodes are non-unique.

20. The method of claim 7, further comprising administering the one or more effective therapeutic interventions to a subject afflicted with the cancer.

* * * * *